United States Patent
Mir

(10) Patent No.: US 10,982,260 B2
(45) Date of Patent: Apr. 20, 2021

(54) SEQUENCING BY EMERGENCE

(71) Applicant: XGenomes Corp., Boston, MA (US)

(72) Inventor: Kalim Mir, Boston, MA (US)

(73) Assignee: XGENOMES CORP., Cambridge, MA (US)

( * ) Notice: Subject to any disclaimer, the term of this patent is extended or adjusted under 35 U.S.C. 154(b) by 0 days.

(21) Appl. No.: 16/205,155

(22) Filed: Nov. 29, 2018

(65) Prior Publication Data

US 2019/0233880 A1 Aug. 1, 2019

Related U.S. Application Data

(60) Provisional application No. 62/591,850, filed on Nov. 29, 2017.

(51) Int. Cl.
  *C12Q 1/68* (2018.01)
  *C12Q 1/6809* (2018.01)
  (Continued)

(52) U.S. Cl.
  CPC .......... *C12Q 1/6809* (2013.01); *C12N 15/10* (2013.01); *C12Q 1/6874* (2013.01);
  (Continued)

(58) Field of Classification Search
  USPC .......... 435/6.1, 6.11, 6.12, 91.1, 91.2, 283.1, 435/287.1, 287.2; 436/94, 501;
  (Continued)

(56) References Cited

U.S. PATENT DOCUMENTS 6,221,592 B1 4/2001 Schwartz et al.
2004/0058349 A1 3/2004 Van Nes et al.
(Continued)

FOREIGN PATENT DOCUMENTS

WO WO 2004/070005 A2 8/2004
WO WO 2012/055415 A1 5/2012
WO WO 2012/056192 A1 5/2012

OTHER PUBLICATIONS

Wang et al., Dried gel hybridization in place of Southern hybridization for detection of Listeria monocytogenes DNA fragments. Lett. Appl. Microbiol., 12, 224-227, 1991.*
(Continued)

*Primary Examiner* — Frank W Lu

(57) ABSTRACT

Systems and methods for nucleic acid sequencing are provided. Nucleic acid is fixed in double-stranded linearized stretched form on a test substrate before being denatured into to single stranded form on the substrate to obtain adjacent fixed first and second strands of the nucleic acid. The strands are exposed to a respective pool of a respective oligonucleotide probe in a set of probes under conditions allowing for probes to form a heteroduplex with a corresponding complementary portion of the fixed first or second strand thereby giving rise to a respective instance of optical activity. An imager measures a location and duration of this optical activity. The exposing and measuring is repeated for probes in the set of probes thereby obtaining a plurality of sets of positions. The nucleic acid sequence is determined from the plurality of sets of positions through compilation of the positions in the sets.

16 Claims, 26 Drawing Sheets

Specification includes a Sequence Listing.

(51) Int. Cl.
| | |
|---|---|
| G01N 33/53 | (2006.01) |
| C12N 15/10 | (2006.01) |
| G16B 30/00 | (2019.01) |
| G16B 40/20 | (2019.01) |
| C12Q 1/6874 | (2018.01) |
| C12Q 1/6876 | (2018.01) |

(52) U.S. Cl.
 CPC ....... *C12Q 1/6876* (2013.01); *G01N 33/5308* (2013.01); *G16B 30/00* (2019.02); *G16B 40/20* (2019.02)

(58) Field of Classification Search
 USPC .......................... 536/23.1, 24.3, 24.33, 25.3
 See application file for complete search history.

(56) References Cited

U.S. PATENT DOCUMENTS

| | | |
|---|---|---|
| 2005/0214842 A1 | 9/2005 | Palanisamy et al. |
| 2018/0327829 A1 | 11/2018 | Mir |

OTHER PUBLICATIONS

Ramesh et al., Rapid denaturation improves chromosome morphology and permits multiple hybridizations during fluorescence in situ hybridization. Biotech. Histochem., 72, 141-143, 1997.*
Babcock, Hazen P., et al., "Analyzing Single Molecule Localization Microscopy Data Using Cubic Splines", Scientific Reports, 7: 552 | DOI:10.1038/s41598-017-00622-w, pubd. Online Apr. 3, 2017.
Beliveau, Brian J., et al., "Single-molecule super-resolution imaging of chromosomes and in situ haplotype visualization using Oligopaint FISH probes", Nature Communications | 6:7147 | DOI: 10.1038/ncomms8147 |www.nature.com/naturecommunications, pubd. May 12, 2015.
Bentley, David R. et al., "Accurate whole human genome sequencing using reversible terminator chemistry", Nature, v. 456, n. 6, p. 53-59 (Nov. 2008).
Boyd, Nicholas et al. "Deep Loco: Fast 3D Localization Microscopy Using Neural Networks", bioRxiv preprint first posted online Feb. 16, 2018; doi; http://dx.doi.org/10.1101/267096.
Chen, Zitian et al., "Highly accurate fluorogenic DNA sequencing with information theory-based error correction", Nature Biotechnology, v. 35, n. 12, p. 1170, 2017.
Deiana, Marco, et al., "Photochromic switching of the DNA helicity induced by azobenzene derivative", Scientific Reports, 6:28605 | DOI: 10.1038/srep28605, Pubd. Jun 24, 2016.
Freitag, C., et al., "Visualizing the entire DNA from a chromosome in a single frame", Biomicrofluidics, Biomicrofluidics v. 9, issue 4, 044114 (2015); https://doi.org/10.1063/1.4923262, pubd. Aug. 5, 2015.
Geertsema, Hylkje J. "Single-Molecule Imaging at High Fluorophore Concentrations by Local Activation of Dye", Biophysical J., v. 108, p. 949-956, Feb. 2015.
Laver, T. et al., "Assessing the performance of the Oxford Nanopore Technologies MinION", Biomol. Det. And Quant., n. 3, p. 1-8 (2015).
Karimi-Busheri, Feridoun et al., "Repair of DNA Strand Gaps and Nicks containing 3'-phosphate and 5'-hydroxyl termini by purified mammalian enzymes", Nucleic Acids Research, v. 26, n. 19, p. 4395-4400 (1998).
Kaykov, Atanas, et al., "Molecular Combing of Single DNA Molecules on the 10 Megabase Scale", Scientific Reports, Scientific Reports | 6:19636 | DOI: 10.1038/srep19636, Published: Jan. 19, 2016.
Kchouk, Mehdi, et al., "Generations of Sequencing Technologies: From First to Next Generation", Biology and Medicine, v. 9, n. 3 p. 1-8 (2017).
Kulkarni, Pranav, et al, "Challenges in the Setup of Large-scale Next-Generation Sequencing Analysis Workflows", Comp. and Struc. Biot. J., n. 15, p. 471-477 (2017).
Kunkel, Thomas A., et al., "Deoxynucleoside [1-thio] triphosphates prevent proofreading during in vitro DNA synthesis", Proc. Natl. Acad. Sci. USA, v. 78, n. 11, p. 6734-3738, Nov. 1981.
Levesque, Marshall J., et al., "Visualizing SNVs to quantify allele-specific expression in single cells", Nat Methods, 10(9); 865-867, Sep. 2013.
Lin, Chenxiang, et al., "Sub-micrometer Geometrically Encoded Fluorescent Barcodes Self-Assembled from DNA", Nat Chem. 4(10); 832-839, Oct. 2012.
Lundquist, Paul M., et al., "Parallel confocal detection of single molecules in real time", Optics Letters, v. 33, n. 9, p. 1026, May 1, 2008.
Marie, Rodolphe, et al., "Integrated view of genome structure and sequence of a single DNA molecule in a nanofluidic device", PNAS, V. 110, N. 13, p. 4893-4898, Mar. 26, 2013.
Mertz, Jerome, et al., "Scanning light-sheet microscopy in the whole mouse brain with HiLo background rejection", J. of Biom. Optics, 15(1), 016027-1-016027-7, Jan./Feb. 2010.
Metzker, Michael, "Termination of DNA synthesis by novel 3'-modified deoxyribonucleoside 5'-triphosphates", Nucleic Acids Research, v. 22, n. 20, p. 4259-4267 (1994).
Mir, Kalim U., "Sequencing Genomes: From Individuals to Populations", Briefings in Functional Genomics and Proteomics, v. 8, n. 5, p. 367-378 (2009).
Nehme, Elias et al., "Deep-STORM: super-resolution single-molecule microscopy by deep learning", Optica, v. 5, n. 4, p. 458-464 (Apr. 2018).
Ovesný, Martin, et al., "ThunderSTORM: a comprehensive ImageJ plug-in for PALM and STORM data analysis and super-resolution imaging", Bionformatics, v. 30, n. 16, p. 2389-2390 (2014).
Roloff, Tim C., et al., "Comparative study of methyl-CpG-binding domain proteins", BMC Genomics, 2003, 4:1, available from: http:biomedcentral.com/1471-2164/4/1.
Song, Kyung-Mi, et al., "Aptamers and Their Biological Applications", Sensors, n. 12, p. 612-631 (2012).
Toseland, Christopher P., "Fluorescent labeling and modification of proteins", J. Chem Biol (2013) 6:85-95.
Woo, Sungwook et al., "Self-assembly of two-dimensional DNA origami lattices using cation-controlled surface diffusion", Nature Communications | 5:4889 | DOI: 10.1038/ncomms5889 |nature. com/naturecommunications, Published Sep. 10, 2014.
Ansorge, W.J., "Next-Generation DNA Sequencing Techniques", New Biotechnology, v. 25, n. 4, Apr. 2009.
International Search Report, I.A. No. PCT/US2018/063162, dated Mar. 13, 2019.
Colomb, et al. "Estimation of microscopy drift using fluorescent nanodiamonds as fiducial marker," J. Microscopy, vol. 266, Issue 3, 2017, pp. 298-306.
Dertinger, T., et al. "Fast, background-free, 3D super-resolution optical fluctuation imaging (SOFI)," PNAS, Dec. 29, 2009, vol. 106, No. 52, pp. 22287-22292.
Henriques, Ricardo, et al. "PALM and STORM: Unlocking Live-Cell Super-Resolution," Biopolymers, vol. 95, No. 5, pp. 322-331.
Hollich, Volker, et al. "Creation of a minimal tiling path of genomic clones for *Drosophila*: provision of a common resource," Microarray Technologies, BioTechniques, vol. 37, No. 2, 2004, pp. 282-284.
Kirshner, H. et al., "3-D PSF fitting for fluorescence microscopy: implementation and localization application," J. Microscopy, vol. 249(1), 2013, pp. 13-25.
Ma, Hongqiang, et al. "A Simple Marker-Assisted 3D Nanometer Drift Correction Method for Superresolution Microscopy," Biophysical Journal, 112, May 23, 2017, pp. 2196-2208.
Schnitzbauer, Joerg, et al. "Super-resolution microscopy with DNA-PAINT," Nat. Protocols 12, No. 6, 2017, pp. 1198-1228.
Vicidomini, Giuseppe, et al. "STED super-resolved microscopy," Nat Methods, vol. 15, Mar. 2018, pp. 173-182.
Wei, Feifei, et al. "Wide Field Super-Resolution Surface Imaging through Plasmonic Structured Illumination Microscopy", Nano Letters, ACS Publications, 2014, 14, pp. 4634-4639.

(56) References Cited

OTHER PUBLICATIONS

Zamboni, Javier Eduardo Diaz, et al. "Estimation Methods of the Point Spread Function Axial Position: A Comparative Computational Study," Journal of Imaging, 2017, 3, 7; www.mdpi.com/journal/jimaging, pp. 26.
Levy-Sakin, M. et al., *"Beyond sequencing: optical mapping of DNA in the age of nanotechnology and nanoscopy"*, Current Opinion in Biotechnology, 24(4), p. 690-698 (Feb. 18, 2013).
Neely, R. K., et al. *"DNA Fluorocode: A single molecule, optical map of DNA with nanometre resolution"*, .Chemical Science, 1(4), p. 453-460 (Aug. 11, 2020).
Rhoads, A., et al., "PacBio sequencing and its applications", Genomics, Proteomics & Bioinformatics, 13(5), p. 278-289 (Nov. 2, 2015).
International Search Report, Application No. PCT/US2019/063551, dated Mar. 16, 2020.
Bertone, P. et al., "Design Optimization Methods for Genomic DNA Tiling Arrays", Gen Res 16, 271-281 (2006).
Chou, et al. 2004 "PICKY: oligo microarray design for large genomes" Bioninform. 20(17), 2893-2902.
Dufour, Y.S., et al., "chipD: A Web Tool to Design Oligonucleotide Probes for High-Density Tiling Arrays", Nucleic Acids Res., v. 38, p. W321-W325 (2010).
Li, X., et al. "Selection of Optimal Oligonucleotide Probes for Microarrays Using Multiple Criteria, Global Alignment and Parameter Estimation", Nucleic Acids Res. v. 33, n. 19, p. 6114-6123 (2005).
Lipson, et al., "Optimization of probe coverage for high-resolution oligonucleotide aCGH" *Bioinform*, v. 23, n. 2 p. e77-e83 (2006).
Pihlak, A., et al., "Rapid Genome Sequencing with Short Universal Tiling Probes", Nature Biotech., v. 26, n. 6. p. 676-684 (Jun. 2008).
Rouillard, et al., "OligoArray 2.0: design of oligonucleotide probes for DNA microarrays using a thermodynamic approach" Nuc Acids Res 31(12), 3057-3062 (2003).
Ryder et al., "MAMMOT—a set of tools for the design, management and visualization of genomic tiling arrays", Bioninform, Genome Analy. 22(7), 883-884 (2006).
Urban, A.E., et al. "High-Resolution Mapping of DNA Copy Alterations in Human Chromosome 22 Using High-Density Tiling Oligonucleotide Arrays", PNAS, v. 103, n. 12, p. 4534-4539 (Mar. 21, 2006).
Wernersson, et al., "OligoWiz 2.0—intergrating sequence feature annotation into the design of microarray probes", Nuc Acids Res, V. 33, W611-W615.

\* cited by examiner (202) A method of sequencing a nucleic acid is provided in which the nucleic acid in double stranded linearized stretched form on a test substrate thereby forming a fixed stretched double stranded nucleic acid.

(206) Denature the fixed stretched double stranded nucleic acid to single stranded form on the test substrate thereby obtaining a fixed first strand and a fixed second strand of the nucleic acid, wherein respective bases of the fixed second strand lie adjacent to corresponding complementary bases of the fixed first strand.

(208) Expose the fixed first strand and the fixed second strand to a respective pool of a respective oligonucleotide probe in a set of oligonucleotide probes. Each oligonucleotide probe in the set of oligonucleotide probes is of a predetermined sequence and length. The exposing occurs under conditions that allow for individual probes of the respective pool of the respective oligonucleotide probe to bind and form a respective heteroduplex with each portion of the fixed first strand or the fixed second strand that is complementary to the respective oligonucleotide probe thereby giving rise to a respective instance of optical activity > (210) The exposing occurs under conditions that allow for individual probes of the respective pool of the respective oligonucleotide probe to transiently and reversibly bind and form the respective heteroduplex with each portion of the fixed first strand or the fixed second strand that is complementary to the individual probes thereby giving rise to an instance of optical activity > (212) Each oligonucleotide probe in the set of oligonucleotide probes is bound with a label

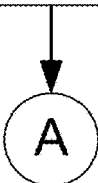

Fig. 2A

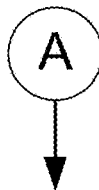

(214) Measure a location on the test substrate and a duration of each respective instance of optical activity occurring during the exposing using a two-dimensional imager.

(216) The measuring the location on the test substrate comprises inputting a frame of data measured by the two-dimensional imager into a trained convolutional neural network. The frame of data comprises the respective instance of optical activity among a plurality of instances of optical activity. Each instance of optical activity in the plurality of instances of optical activity corresponds to an individual probe binding to a portion of the fixed first strand or the fixed second strand, and. Responsive to the inputting, the trained convolutional neural network identifies a position on the test substrate of each of one or more instances of optical activity in the plurality of instances of optical activity.

(218) Repeat the exposing and measuring for respective oligonucleotide probes in the set of oligonucleotide probes, thereby obtaining a plurality of sets of positions on the test substrate, each respective set of positions on the test substrate corresponding to an oligonucleotide probe in the set of oligonucleotide probes (200) The set of oligonucleotide probes comprises a plurality of subsets of the oligonucleotide probes and where repeating the exposing and measuring is performed for each respective subset of oligonucleotide probes in the plurality of subsets of oligonucleotide probes (202) Determine the sequence of at least a portion of the nucleic acid from the plurality of sets of positions on the test substrate by compiling the positions on the test substrate represented by the plurality of sets of positions.

Fig. 2B (302 - 304) A method of sequencing a nucleic acid is provided in which the nucleic acid is fixed in linearized stretched form on a test substrate thereby forming a fixed stretched nucleic acid.

> (306) The nucleic acid is double stranded nucleic acid and the method further comprises denaturing the fixed double stranded nucleic acid to single stranded form on the test substrate thereby obtaining a fixed first strand and a fixed second strand of the nucleic acid, wherein the fixed second strand is complementary to the fixed first strand.

> (308) The nucleic acid is single stranded RNA (310) Expose the fixed stretched nucleic acid to a respective pool of a respective oligonucleotide probe in a set of oligonucleotide probes, wherein each oligonucleotide probe in the set of oligonucleotide probes is of a predetermined sequence and length, the exposing (b) occurring under conditions that allow for individual probes of the respective pool of the respective oligonucleotide probe to transiently and reversibly to each portion of the fixed nucleic acid that is complementary to the respective oligonucleotide probe thereby giving rise to a respective instance of optical activity (312) Measure a location on the test substrate and a duration of each respective instance of optical activity occurring during the exposing using a two-dimensional imager (314) Repeat the exposing and measuring for respective oligonucleotide probes in the set of oligonucleotide probes, thereby obtaining a plurality of sets of positions on the test substrate, each respective set of positions on the test substrate corresponding to an oligonucleotide probe in the set of oligonucleotide probes.

(316) Determine the sequence of at least a portion of the nucleic acid from the plurality of sets of positions on the test substrate by compiling the positions on the test substrate represented by the plurality of sets of positions.

Fig. 3

(402 - 404) A method of analyzing a nucleic acid is provided in which the nucleic acid is fixed in double stranded form on a test substrate thereby forming a fixed double stranded nucleic acid

(406) Denature the fixed double stranded nucleic acid to single stranded form on the test substrate thereby obtaining a fixed first strand and a fixed second strand of the nucleic acid, wherein the fixed second strand is complementary to the fixed first strand

(408) Expose the fixed first strand and the fixed second strand to one or more oligonucleotide probes and determining whether the one or more oligonucleotide probes binds to the fixed first strand or the fixed second strand.

Fig. 4 accggttgtactagaggattcggatagctaaaatcgtaaatgtccccctcag (SEQ ID NO. 3)

Fig. 6A accggttgtactagaggatgccccaatagctggatgcgtaaaaatgcggattataatgtccccctcag (SEQ ID NO. 4)

Fig. 6B

Fig. 7A 702 acaaattgtactagagga|ttcgga|tagctaaaatcgt|aaaatgcgga|ttaatgtcccccctcag (SEQ ID NO. 5)
         704     704       704        706    704   706     710
         cct     cct       cct        att    cct   att
         708     708       708               708

712 aac
    acaaattgt|actagagga|ttcgga|tagctaaaatcgt|aaaatgcgga|ttaatgtcccccctcag (SEQ ID NO. 5)
714    704      704      704       704    706      710
       cct      cct      cct       cct    att
       708      708      708       708    708

Fig. 7B 702 acaaattgtactagagga|ttcgga|tagctaaaatcgt|aaaatgcgga|ttataatgtccccctcag (SEQ ID NO. 5)
         704     704       704         704       708
         cct     cct       cct         cct
         708     708       708

716-1 ttt                                716-2 ttt           716-3 ttt
                                              ttt                 ttt
                                              ttt                 ttt
718 adaaattgt|actagagga|ttcgga|tagcta|aaaatcgt|aaaatgcgga|ttataatgtccccctcag
    702  704    704      704    720     704    708   720      708
         cct    cct      cct           cct
         708    708      708

Fig. 7C

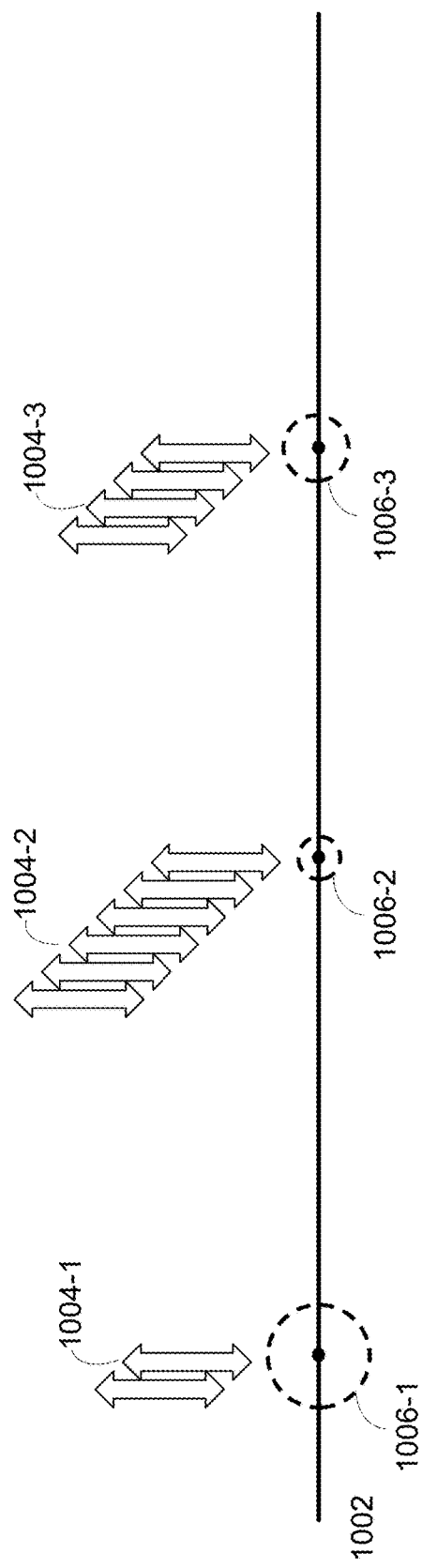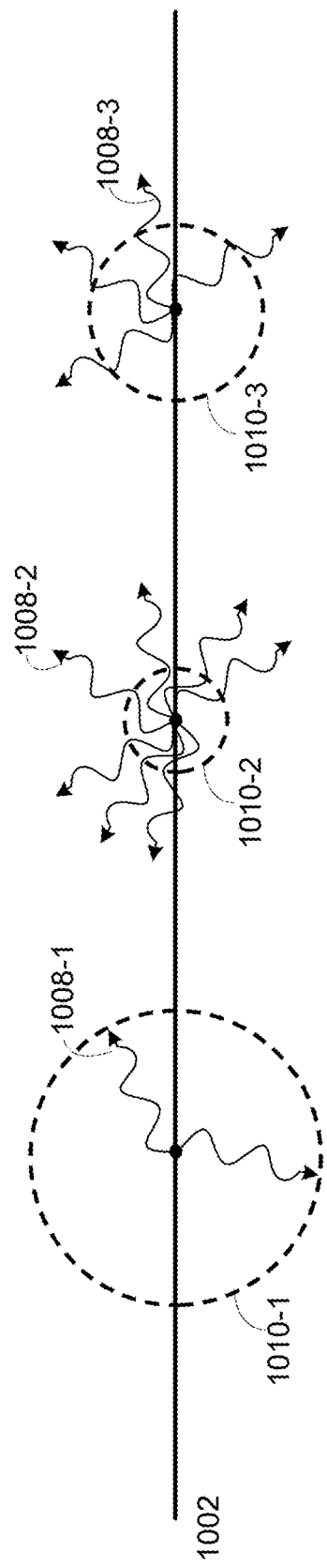

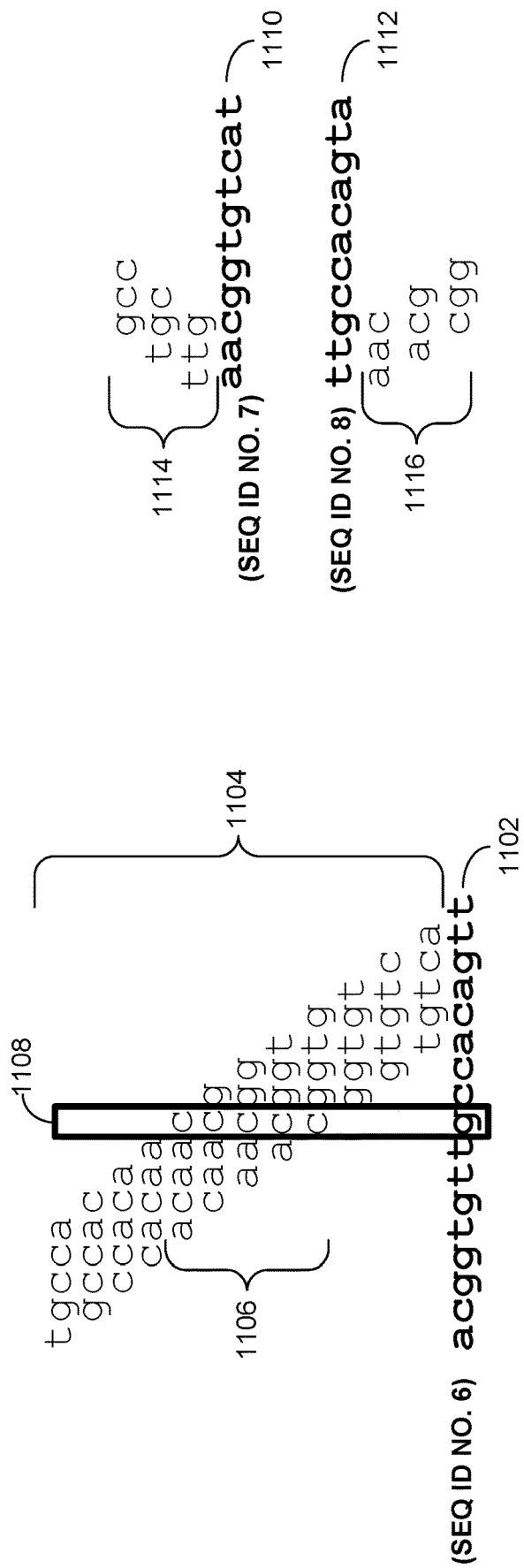

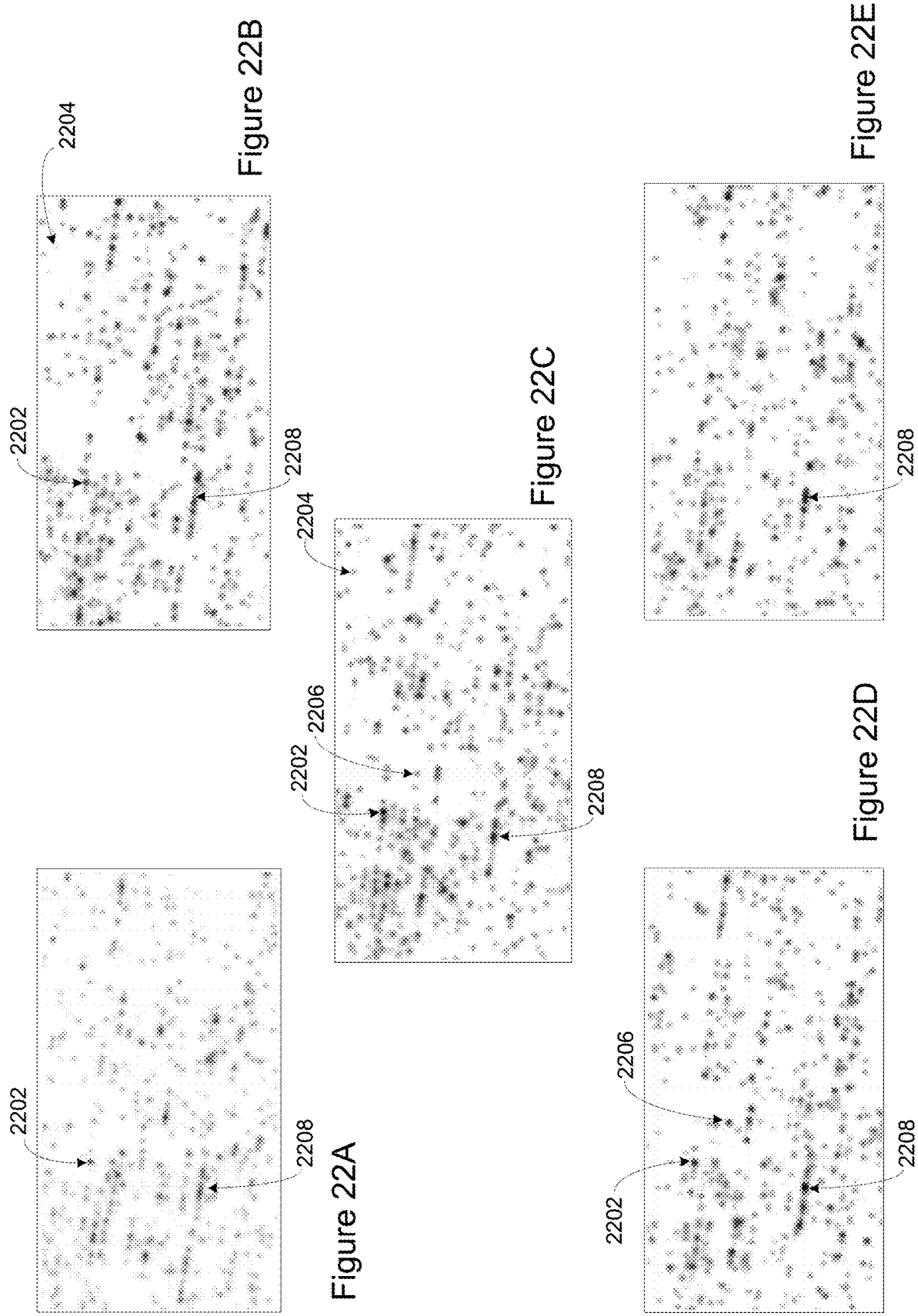

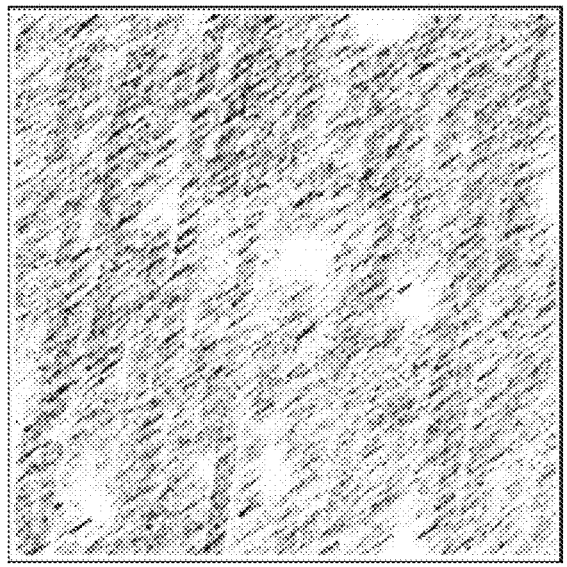
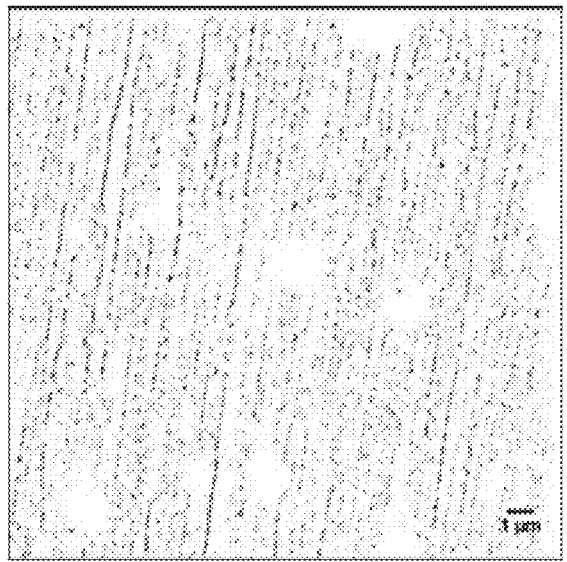
Figure 23A
Figure 23B
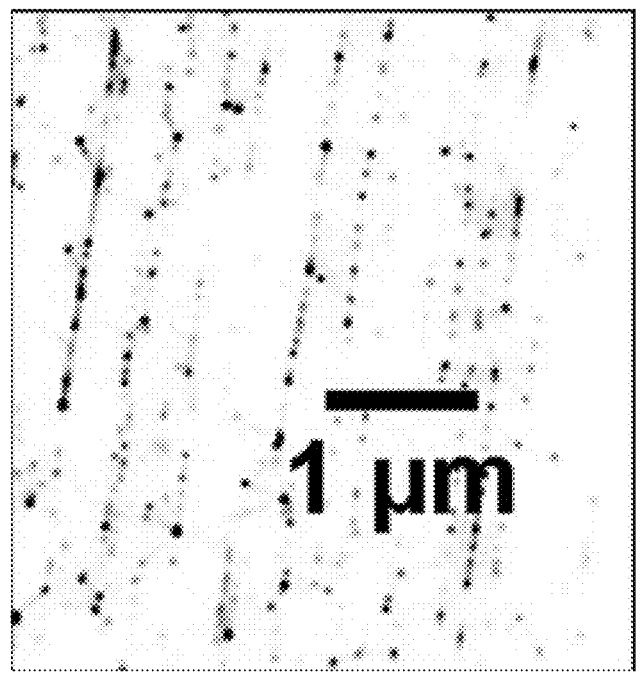
Figure 23C

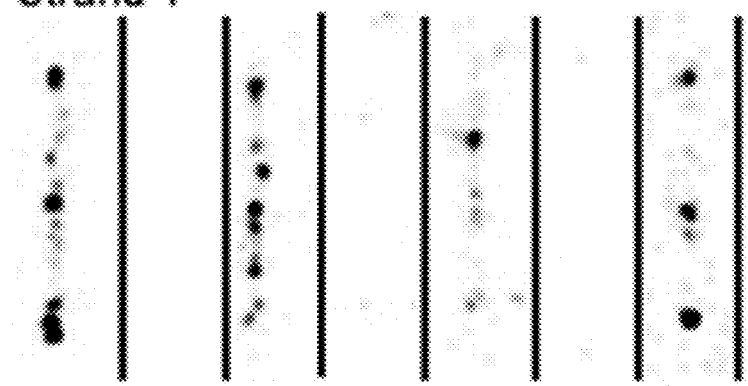
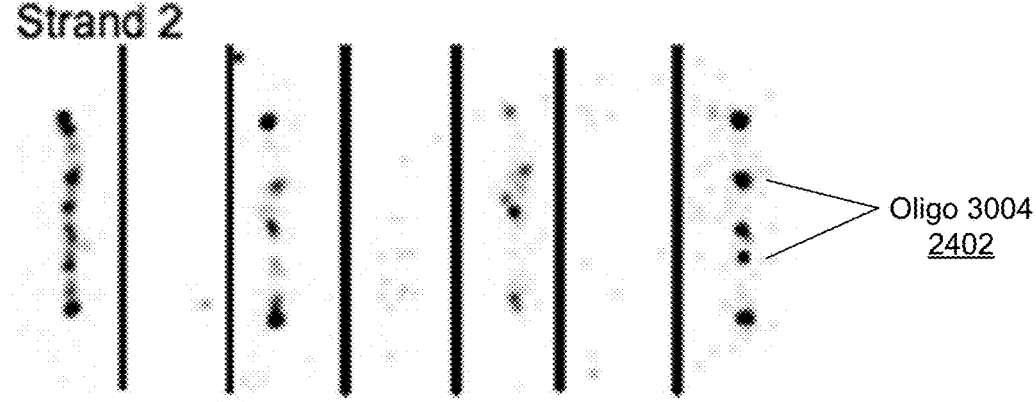
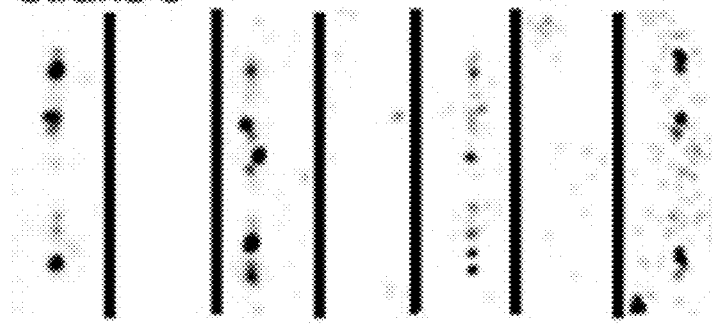
Figure 24

SEQUENCING BY EMERGENCE

CROSS REFERENCE TO RELATED APPLICATION

This application claims priority to U.S. Patent Application No. 62/591,850 entitled "Sequencing by Emergence," filed Nov. 29, 2017, which is hereby incorporated by reference.

REFERENCE TO SEQUENCE LISTING

The Sequence Listing text copy submitted herewith via EFS-Web was created on Apr. 2, 2019, is entitled 1184965005US_ST25.txt, is 6 kilobytes in size and is herein incorporated by reference in its entirety.

TECHNICAL FIELD

The present disclosure relates generally to systems and methods for sequencing nucleic acids via transitory binding of probes to one or more polynucleotides.

BACKGROUND

DNA sequencing first became a reality with gel electrophoresis-based methods: the dideoxy chain termination method (e.g., Sanger et al., Proc. Natl. Acad. Sci. 74:5463-5467, 1977), and the chemical degradation method (e.g., Maxam et al., Proc. Natl. Acad. Sci. 74:560-564, 1977). These methods of sequencing nucleotides were both time-consuming and expensive. Nevertheless, the former led to the sequencing the human genome for the first time, despite taking more than ten years and hundreds of millions of dollars.

As the dream of personalized medical care comes ever nearer to fruition, there is an increasing need for inexpensive, large-scale methods for sequencing individual human genomes (Mir, Sequencing Genomes: From Individuals to Populations, Briefings in Functional Genomics and Proteomics, 8: 367-378, 2009). Several sequencing methods that avoid gel electrophoresis (and which are subsequently less expensive) were developed as "next generation sequencing." One such method of sequencing, using reversible terminators (as practiced by Illumina Inc.), is dominant. The detection methods used in the most evolved form of Sanger sequencing and the currently dominant Illumina technology involve fluorescence. Other possible means of detecting single nucleotide insertions include detection using a proton release (e.g., via a field effect transistor, an ionic current through a nanopore and electron microscopy. Illumina's chemistry involves cyclical addition of nucleotides using reversible terminators (Canard et al., Metzker Nucleic Acids Research 22:4259-4267, 1994), which bear fluorescent labels (Bentley et al., Nature 456:53-59, 2008). Illumina sequencing starts with clonally amplifying single genomic molecules, and substantial upfront sample processing is needed to convert the target genome into a library that is then clonally amplified as clusters.

However, two methods have since reached the market that circumvent the need for amplification prior to sequencing. Both new methods conduct fluorescent Sequencing by Synthesis (SbS) on single molecules of DNA. The first method, from HelicosBio (now SeqLL), conducts stepwise SbS with reversible termination (Harris et al., Science, 320:106-9, 2008). The second method, SMRT Sequencing from Pacific Biosciences uses labels on a terminal phosphate, a natural leaving group of the reaction incorporating a nucleotide, which allows sequencing to be conducted continuously and without the need for exchanging reagents. One of the downsides of this approach is that throughput is low as the detector needs to remain fixed on one field of view (e.g., Levene et al., Science 299:682-686, 2003 and Eid et al., Science, 323:133-8, 2009). A somewhat similar approach to Pacific Bioscience sequencing is the method being developed by Genia (now part of Roche) by detecting SbS via a nanopore, rather than via optical methods.

The most commonly used sequencing methods are limited in read length, which increases both the cost of sequencing and the difficulty of assembling the resulting reads. The read lengths obtained by Sanger sequencing are in the 1000 base range (e.g., Kchouk et al., Biol. Med. 9:395, 2017). Roche 454 sequencing and Ion Torrent both have read lengths in the hundreds of bases range. Illumina sequencing, which initially started with a read of about 25 bases, is now typically 150-300 base pair reads. However, as fresh reagents need to be supplied for each base of the read length, sequencing 250 bases rather than 25 requires 10× more time and 10× more of the costly reagents. Recently, the standard read-lengths of Illumina instruments have been decreased to around 150 bases, presumably due to their technology being subject to phasing (molecules within clusters getting out of synchronization) that introduces error as the reads get longer.

The longest read lengths possible in commercial systems are obtained by nanopores strand sequencing from Oxford Nanopores Technology (ONT) and Pacific Bioscience (PacBio) sequencing (e.g., Kchouk et al., Biol. Med. 9:395, 2017). The latter routinely has reads that average about 10,000 bases in length, while the former on very rare occasions is able to get reads that are several hundreds of kilobases in length (e.g., Laver et al., Biomol. Det. Quant. 3:1-8, 2015). While these longer read lengths are desirable in terms of alignments, they come at the cost of accuracy. Accuracy is often so poor that for most human sequencing applications these methods can only be used as a supplement to Illumina sequencing, not as a stand-alone sequencing technology. Moreover, the throughput of existing long-read technologies is too low for routine human genome scale sequencing.

Beside ONT and PacBio sequencing, a number of approaches exist that are not sequencing technologies per se, but are sample preparation approaches that supplement Illumina short read sequencing technology to provide a scaffold for building longer reads. Of these, one is the droplet based technology developed by 10× Genomics, which isolates 100-200 kb fragments (e.g., the average length range of fragments after extraction) within droplets and processes them into libraries of shorter length fragments each of which contains a sequence identifiers tag specific for the 100-200 kb from which they originate, which upon sequencing of the genome from a multiplicity of droplets can be deconvolved into ~50-200 Kb buckets (Goodwin et al., Nat. Rev. Genetics 17:333-351, 2016). Another approach has been developed by Bionano Genomics that stretches and induces nicks in DNA via exposure to a nicking endonuclease. The method fluorescently detects points of nicking to provide a map or scaffold of the molecule. This method at present has not been developed to have a high enough density to help assemble genomes, but it nevertheless provides a direct visualization of the genome and is able to detect large structural variations and determine long-range haplotypes.

Despite the different sequencing methods developed and the general trend in decreasing sequencing cost, the size of the human genome continues to lead to high sequencing costs for patients. An individual human genome is organized into 46 chromosomes, of which the shortest is about 50 megabases and the longest 250 megabases. NGS sequencing methods still have many issues that affect performance, including the reliance on reference genomes that can substantially increase the time required for analysis (e.g., as discussed in Kulkarni et al., Comput Struct Biotechnol J. 15:471-477, 2017).

Given the above background, what is needed in the art are devices, systems and methods for providing a stand-alone sequencing technology that is efficient in the use of reagents and time and that provides long, haplotype-resolved reads without loss of accuracy.

The information disclosed in this Background section is only for enhancement of understanding of the general background and should not be taken as an acknowledgment or any form of suggestion that this information forms the prior art already known to a person skilled in the art.

SUMMARY

The present disclosure addresses the need in the art for devices, systems and methods for providing improved nucleic acid sequencing techniques. In one broad aspect, the present disclosure comprises a method of identifying at least one unit of a multi-unit molecule by binding molecular probes to one or more units of the molecule. The present disclosure is based on the detection of single molecule interactions of one or more species of molecular probe with the molecule. In some embodiments the probes bind transiently to at least one unit of the molecule. In some embodiments the probes bind repetitively to at least one unit of the molecule. In some embodiments the molecular entities are localized on a macromolecule, surface or matrix to a nanometric accuracy.

In one aspect, disclosed herein is a method of sequencing a nucleic acid. The method comprises (a) fixing the nucleic acid in double-stranded linearized stretched form on a test substrate thereby forming a fixed stretched double-stranded nucleic acid. The method further comprises (b) denaturing the fixed stretched double-stranded nucleic acid to single stranded form on the test substrate thereby obtaining a fixed first strand and a fixed second strand of the nucleic acid, where respective bases of the fixed second strand lie adjacent to corresponding complementary bases of the fixed first strand. The method continues by (c) exposing the fixed first strand and the fixed second strand to a respective pool of a respective oligonucleotide probe in a set of oligonucleotide probes, where each oligonucleotide probe in the set of oligonucleotide probes is of a predetermined sequence and length. The exposing (c) occurs under conditions that allow for individual probes of the respective pool of the respective oligonucleotide probe to bind and form a respective heteroduplex with each portion of the fixed first strand or the fixed second strand that is complementary to the respective oligonucleotide probe thereby giving rise to a respective instance of optical activity. The method continues with (d) measuring a location on the test substrate and a duration of each respective instance of optical activity occurring during the exposing (c) using a two-dimensional imager. Then, the method proceeds by (e) repeating the exposing (c) and measuring (d) for respective oligonucleotide probes in the set of oligonucleotide probes, thereby obtaining a plurality of sets of positions on the test substrate. Each respective set of positions on the test substrate corresponding to an oligonucleotide probe in the set of oligonucleotide probes. The method further includes (f) determining the sequence of at least a portion of the nucleic acid from the plurality of sets of positions on the test substrate by compiling the positions on the test substrate represented by the plurality of sets of positions.

In some embodiments, the exposing (c) occurs under conditions that allow for individual probes of the respective pool of the respective oligonucleotide probe to transiently and reversibly bind and form the respective heteroduplex with each portion of the fixed first strand or the fixed second strand that is complementary to the individual probes thereby giving rise to an instance of optical activity. In some embodiments, the exposing (c) occurs under conditions that allow for individual probes of the respective pool of the respective oligonucleotide probe to repeatedly transiently and reversibly bind and form the respective heteroduplex with each portion of the fixed first strand or the fixed second strand that is complementary to the individual probes thereby repeatedly giving rise to the respective instance of optical activity. In some such embodiments, each oligonucleotide probe in the set of oligonucleotide probes is bound with a label (e.g., a dye, a fluorescent nanoparticle, or a light-scattering particle).

In some embodiments, The method of claim 1, the exposing is in the presence of a first label in the form of an intercalating dye, each oligonucleotide probe in the set of oligonucleotide probes is bound with a second label, the first label and the second label have overlapping donor emission and acceptor excitation spectra that causes one of the first label and the second label to fluoresce when the first label and the second label are in close proximity to each other, and the respective instance of optical activity is from a proximity of the intercalating dye, intercalating the respective heteroduplex between the oligonucleotide and the fixed first strand or the fixed second strand, to the second label.

In some embodiments, the exposing is in the presence of a first label in the form of an intercalating dye, each oligonucleotide probe in the set of oligonucleotide probes is bound with a second label, the first label causes the second label to fluoresce when the first label and the second label are in close proximity to each other, and the respective instance of optical activity is from a proximity of the intercalating dye, intercalating the respective heteroduplex between the oligonucleotide and the fixed first strand or the fixed second strand, to the second label.

In some embodiments, the exposing is in the presence of a first label in the form of an intercalating dye, each oligonucleotide probe in the set of oligonucleotide probes is bound with a second label, the second label causes the first label to fluoresce when the first label and the second label are in close proximity to each other, and the respective instance of optical activity is from a proximity of the intercalating dye, intercalating the respective heteroduplex between the oligonucleotide and the fixed first strand or the fixed second strand, to the second label.

In some embodiments, the exposing is in the presence of an intercalating dye, and the respective instance of optical activity is from a fluorescence of the intercalating dye intercalating the respective heteroduplex between the oligonucleotide and the fixed first strand or the fixed second strand. In such embodiments, the respective instance of optical activity is greater than a fluorescence of the intercalating dye before it intercalates the respective heteroduplex.

In some embodiments, more than one oligonucleotide probe in the set of oligonucleotide probes is exposed to the fixed first strand and the fixed second strand during a single instance of the exposing (c), and each different oligonucleotide probe in the set of oligonucleotide probes that is exposed to the fixed first strand and the fixed second strand during the single instance of the exposing (c) is associated with a different label. In some such embodiments, a first pool of a first oligonucleotide probe in the set of oligonucleotide probes, the first oligonucleotide probe being associated with a first label, is exposed to the fixed first strand and the fixed second strand during the single instance of the exposing (c), a second pool of a second oligonucleotide probe in the set of oligonucleotide probes, the second oligonucleotide probe being associated with a second label, is exposed to the fixed first strand and the fixed second strand during the single instance of the exposing (c), and the first label and the second label are different. Alternatively, a first pool of a first oligonucleotide probe in the set of oligonucleotide probes, the first oligonucleotide probe being associated with a first label, is exposed to the fixed first strand and the fixed second strand during the single instance of the exposing (c), a second pool of a second oligonucleotide probe in the set of oligonucleotide probes, the second oligonucleotide probe being associated with a second label, is exposed to the fixed first strand and the fixed second strand during the single instance of the exposing (c), a third pool of a third oligonucleotide probe in the set of oligonucleotide probes, the third oligonucleotide probe being associated with a third label, is exposed to the fixed first strand and the fixed second strand during the single instance of the exposing (c), and the first label, the second label, and the third label are each different.

In some embodiments, the repeating (e), the exposing (c), and the measuring (d) are each performed for each single oligonucleotide probe in the set of oligonucleotide probes.

In some embodiments, the exposing (c) is done for a first oligonucleotide probe in the set of oligonucleotide probes at a first temperature and the repeating (e), the exposing (c), and the measuring (d) includes performing the exposing (c) and the measuring (d) for the first oligonucleotide at a second temperature.

In some embodiments, the exposing (c) is done for a first oligonucleotide probe in the set of oligonucleotide probes at a first temperature, instances of the (e) repeating the exposing (c) and measuring (d) include performing the exposing (c) and the measuring (d) for the first oligonucleotide at each of a plurality of different temperatures, and the method further comprises constructing a melting curve for the first oligonucleotide probe using the measured locations and durations of optical activity recorded by the measuring (d) for the first temperature and each temperature in the plurality of different temperatures.

In some embodiments, the set of oligonucleotide probes comprises a plurality of subsets of the oligonucleotide probes and the repeating (e), the exposing (c), and the measuring (d) is performed for each respective subset of oligonucleotide probes in the plurality of subsets of oligonucleotide probes. In some such embodiments, each respective subset of oligonucleotide probes comprises two or more different probes from the set of oligonucleotide probes. Alternatively, each respective subset of oligonucleotide probes comprises four or more different probes from the set of oligonucleotide probes. In some such embodiments, the set of oligonucleotide probes consists of four subsets of oligonucleotide probes. In some embodiments, the method further comprises dividing the set of oligonucleotide probes into the plurality of subsets of oligonucleotide probes based on a calculated or experimentally derived melting temperature of each oligonucleotide probe, where oligonucleotide probes with similar melting temperature are placed in the same subset of oligonucleotide probes by the dividing and where a temperature or a duration of an instance of the exposing (c) is determined by an average melting temperature of the oligonucleotide probes in the corresponding subset of oligonucleotide probes. Further still, in some embodiments, the method further comprises dividing the set of oligonucleotide probes into the plurality of subsets of oligonucleotide probes based on a sequence of each oligonucleotide probe, where oligonucleotide probes with overlapping sequences are placed in different subsets.

In some embodiments, the measuring the location on the test substrate comprises identifying and fitting the respective instance of optical activity with a fitting function to identify and fit a center of the respective instance of optical activity in a frame of data obtained by the two-dimensional imager, and the center of the respective instance of optical activity is deemed to be the position of the respective instance of optical activity on the test substrate. In some such embodiments, the fitting function is a Gaussian function, a first moment function, a gradient-based approach, or a Fourier Transform.

In some embodiments, the respective instance of optical activity persists across a plurality of frames measured by the two-dimensional imager, the measuring the location on the test substrate comprises identifying and fitting the respective instance of optical activity with a fitting function across the plurality of frames to identify a center of the respective instance of optical activity across the plurality of frames, and the center of the respective instance of optical activity is deemed to be the position of the respective instance of optical activity on the test substrate across the plurality of frames. In some such embodiments, the fitting function is a Gaussian function, a first moment function, a gradient-based approach, or a Fourier Transform.

In some embodiments, the measuring the location on the test substrate comprises inputting a frame of data measured by the two-dimensional imager into a trained convolutional neural network, the frame of data comprises the respective instance of optical activity among a plurality of instances of optical activity, each instance of optical activity in the plurality of instances of optical activity corresponds to an individual probe binding to a portion of the fixed first strand or the fixed second strand, and responsive to the inputting, the trained convolutional neural network identifies a position on the test substrate of each of one or more instances of optical activity in the plurality of instances of optical activity.

In some embodiments, the measuring resolves the center of the respective instance of optical activity to a position on the test substrate with a localization precision of at least 20 nm, at least 2 nm, at least 60 nm, or at least 6 nm.

In some embodiments, the measuring resolves the center of the respective instance of optical activity to a position on the test substrate, where the position is a sub-diffraction limited position.

In some embodiments, the measuring (d) the location on the test substrate and the duration of the respective instance of optical activity measures more than 5000 photons at the location, more than 50,000 photons at the location, or more than 200,000 photons at the location.

In some embodiments, the respective instance of optical activity is more than a predetermined number of standard deviations (e.g., more than 3, 4, 5, 6, 7, 8, 9, or 10 standard deviations) over a background observed for the test substrate.

In some embodiments, each respective oligonucleotide probe in the plurality of oligonucleotide probes comprises a unique N-mer sequence, where N is an integer in the set {1, 2, 3, 4, 5, 6, 7, 8, and 9} and where all unique N-mer sequences of length N are represented by the plurality of oligonucleotide probes. In some such embodiments, the unique N-mer sequence comprises one or more nucleotide positions occupied by one or more degenerate nucleotides. In some such embodiments, each degenerate nucleotide position in the one or more nucleotide positions is occupied by a universal base (e.g., 2'-Deoxyinosine). In some such embodiments, the unique N-mer sequence is 5' flanked by a single degenerate nucleotide position and 3' flanked by a single degenerate nucleotide position. Alternatively, the 5' single degenerate nucleotide and the 3' single degenerate nucleotide are each 2'-Deoxyinosine.

In some embodiments, the nucleic acid is at least 140 bases in length and the determining (f) determines a coverage of the sequence of the nucleic acid sequence of greater than 70%. In some embodiments, the nucleic acid is at least 140 bases in length and the determining (f) determines a coverage of the sequence of the nucleic acid sequence of greater than 90%. In some embodiments, the nucleic acid is at least 140 bases in length and the determining (f) determines a coverage of the sequence of the nucleic acid sequence of greater than 99%. In some embodiments, the determining (f) determines a coverage of the sequence of the nucleic acid sequence of greater than 99%.

In some embodiments, the nucleic acid is at least 10,000 bases in length or at least 1,000,000 bases in length.

In some embodiments, the test substrate is washed prior to repeating the exposing (c) and measuring (d), thereby removing a respective oligonucleotide probe from the test substrate prior to exposing the test substrate to another oligonucleotide probe in the set of oligonucleotide probes.

In some embodiments, the fixing (a) comprises applying the nucleic acid to the test substrate by molecular combing (receding meniscus), flow stretching nanoconfinement, or electro-stretching.

In some embodiments, each respective instance of optical activity has an observation metric that satisfies a predetermined threshold. In some such embodiments, the observation metric comprises a duration, a signal to noise, a photon count, or an intensity. In some embodiments, the predetermined threshold distinguishes between (i) a first form of binding in which each residue of the unique N-mer sequence binds to a complementary base in the fixed first strand or the fixed second strand of the nucleic acid, and (ii) a second form of binding in which there is at least one mismatch between the unique N-mer sequence and a sequence in the fixed first strand or the fixed second strand of the nucleic acid that the respective oligonucleotide probe has bound to form the respective instance of optical activity.

In some embodiments, each respective oligonucleotide probe in the set of oligonucleotide probes has its own corresponding predetermined threshold. In some such embodiments, the predetermined threshold for each respective oligonucleotide probe in the set of oligonucleotide probes is derived from a training dataset. For instance, in some embodiments, the predetermined threshold for each respective oligonucleotide probe in the set of oligonucleotide probes is derived from the training dataset, and the training set comprises, for each respective oligonucleotide probe in the set of oligonucleotide probes, a measure of the observation metric for the respective oligonucleotide probe upon binding to a reference sequence such that each residue of the unique N-mer sequence of the respective oligonucleotide probe binds to a complementary base in the reference sequence. In some such embodiments, the reference sequence is fixed on a reference substrate. Alternatively, the reference sequence is included with the nucleic acid and fixed on the test substrate. In some embodiments, the reference sequence comprises all or a portion of the genome of, PhiX174, M13, lambda phage, T7 phage, or *Escherichia coli, Saccharomyces cerevisiae*, or *Saccharomyces pombe*. In some embodiments, the reference sequence is a synthetic construct of known sequence. In some embodiments, the reference sequence comprises all or a portion of rabbit globin RNA.

In some embodiments, a respective oligonucleotide probe in the set of oligonucleotide probes yields a first instance of optical activity by binding to a complementary portion of the fixed first strand, and a second instance of optical activity by binding to a complementary portion of the fixed second strand.

In some embodiments, a respective oligonucleotide probe in the set of oligonucleotide probes yields two or more first instances of optical activity by binding to two or more complementary portions of the fixed first strand, and two or more second instances of optical activity by binding two or more complementary portions of the fixed second strand.

In some embodiments, the respective oligonucleotide probe binds to a portion of the fixed first strand or the fixed second strand that is complementary to the respective oligonucleotide probe three or more times during the exposing (c) thereby resulting in three or more instances of optical activity, each instance of optical activity representing a binding event in the plurality of binding events.

In some embodiments, the respective oligonucleotide probe binds to a portion of the fixed first strand or the fixed second strand that is complementary to the respective oligonucleotide probe five or more times during the exposing (c) thereby resulting in five or more instances of optical activity, each instance of optical activity representing a binding event in the plurality of binding events.

In some embodiments, the respective oligonucleotide probe binds to a portion of the fixed first strand or the fixed second strand that is complementary to the respective oligonucleotide probe ten or more times during the exposing (c) thereby resulting in ten or more instances of optical activity, each instance of optical activity representing a binding event in the plurality of binding events.

In some embodiments, the exposing (c) occurs for five minutes or less, for two minutes or less, or for one minute or less.

In some embodiments, the exposing (c) occurs across one or more frames of the two-dimensional imager, two or more frames of the two-dimensional imager, 500 or more frames of the two-dimensional imager or across 5,000 or more frames of the two-dimensional imager.

In some embodiments, the exposing (c) is done for a first oligonucleotide probe in the set of oligonucleotide probes for a first period of time, the repeating (e), the exposing (c) and the measuring (d) includes performing the exposing (c) for a second oligonucleotide for a second period of time, and the first period of time is greater than the second period of time.

In some embodiments, the exposing (c) is done for a first oligonucleotide probe in the set of oligonucleotide probes for a first number of frames of the two-dimensional imager, the repeating (e), the exposing (c) and the measuring (d) includes performing the exposing (c) for a second oligonucleotide for a second number of frames of the two-dimensional imager, and the first number of frames is greater than the second number of frames.

In some embodiments, each oligonucleotide probe in the set of oligonucleotide probes is of the same length.

In some embodiments each oligonucleotide probe in the set of oligonucleotide probes is of the same length M, M is a positive integer of 2 or greater (e.g., M is 2, 3, 4, 5, 6, 7, 8, 9, 10, or greater than 10), and the determining (f) the sequence of at least a portion of the nucleic acid from the plurality of sets of positions on the test substrate further uses the overlapping sequences of the oligonucleotide probes represented by the plurality of sets of positions. In some such embodiments, each oligonucleotide probe in the set of oligonucleotide probes shares M−1 sequence homology with another oligonucleotide probe in the set of oligonucleotide probes. In some such embodiments, the determining the sequence of at least a portion of the nucleic acid from the plurality of sets of positions on the test substrate comprises determining a first tiling path corresponding to the fixed first strand and a second tiling path corresponding to the fixed second strand. In some such embodiments, a break in the first tiling path is resolved using a corresponding portion of the second tiling path. Alternatively, a break in the first tiling path or the second tiling path is resolved using a reference sequence. Alternatively, a break in the first tiling path or the second tiling path is resolved using corresponding portions of a third tiling path or a fourth tiling path obtained from another instance of the nucleic acid. In some such embodiments, a confidence in sequence assignment of the sequence is increased using corresponding portions of the first tiling path and the second tiling path. Alternatively, a confidence in sequence assignment of the sequence is increased using corresponding portions of a third tiling path or a fourth tiling path obtained from another instance of the nucleic acid.

In some embodiments, a length of time of an instance of the exposing (c) is determined by an estimated melting temperature of a respective oligonucleotide probe in the set of oligonucleotide probes used in the instance of the exposing (c).

In some embodiments, the method further comprises (f) exposing the fixed double strand or fixed first strand and the fixed second strand to an antibody, affimer, nanobody, aptamer, or methyl-binding protein to thereby determine a modification to the nucleic acid or to correlate with the sequence of the portion of the nucleic acid from the plurality of sets of positions on the test substrate.

In some embodiments, the test substrate is a two-dimensional surface. In some such embodiments, the two-dimensional surface is coated with a gel or a matrix.

In some embodiments, the test substrate is a cell, three-dimensional matrix or gel.

In some embodiments, the test substrate is bound with a sequence-specific oligonucleotide probe prior to the fixing (a) and the fixing (a) comprises capturing the nucleic acid on the test substrate using a sequence-specific oligonucleotide probe bound to the test substrate.

In some embodiments, the nucleic acid is in a solution that comprises an additional plurality of cellular components and the fixing (a) or denaturing (b) further comprises washing the test substrate after the nucleic acid has been fixed to the test substrate and prior to the exposing (c) thereby purifying the additional plurality of cellular components away from the nucleic acid.

In some embodiments, the test substrate is passivized with polyethylene glycol, bovine serum albumin-biotin-streptavidin, casein, bovine serum albumin (BSA), one or more different tRNAs, one or more different deoxyribonucleotides, one or more different ribonucleotides, salmon sperm DNA, pluronic F-127, Tween-20, hydrogen silsesquioxane (HSQ), or any combination thereof prior to the exposing (c).

In some embodiments, the test substrate is coated with a vinylsilane coating comprising 7-octenyltrichlorosilane prior to the fixing (a).

Another aspect of the present disclosure provides a method of sequencing a nucleic acid, comprising (a) fixing the nucleic acid in linearized stretched form on a test substrate thereby forming a fixed stretched nucleic acid, (b) exposing the fixed stretched nucleic acid to a respective pool of a respective oligonucleotide probe in a set of oligonucleotide probes, where each oligonucleotide probe in the set of oligonucleotide probes is of a predetermined sequence and length, the exposing (b) occurring under conditions that allow for individual probes of the respective pool of the respective oligonucleotide probe to transiently and reversibly to each portion of the fixed nucleic acid that is complementary to the respective oligonucleotide probe thereby giving rise to a respective instance of optical activity, (c) measuring a location on the test substrate and a duration of each respective instance of optical activity occurring during the exposing (b) using a two-dimensional imager, (d) repeating the exposing (b) and measuring (c) for respective oligonucleotide probes in the set of oligonucleotide probes, thereby obtaining a plurality of sets of positions on the test substrate, each respective set of positions on the test substrate corresponding to an oligonucleotide probe in the set of oligonucleotide probes, and (e) determining the sequence of at least a portion of the nucleic acid from the plurality of sets of positions on the test substrate by compiling the positions on the test substrate represented by the plurality of sets of positions. In some such embodiments, the nucleic acid is double-stranded nucleic acid and the method further comprises denaturing the fixed double-stranded nucleic acid to single stranded form on the test substrate thereby obtaining a fixed first strand and a fixed second strand of the nucleic acid, where the fixed second strand is complementary to the fixed first strand. In some embodiments, the nucleic acid is single stranded RNA.

Another aspect of the present disclosure provides a method of analyzing a nucleic acid, comprising (a) fixing the nucleic acid in double-stranded form on a test substrate thereby forming a fixed double-stranded nucleic acid, (b) denaturing the fixed double-stranded nucleic acid to single stranded form on the test substrate thereby obtaining a fixed first strand and a fixed second strand of the nucleic acid, where the fixed second strand is complementary to the fixed first strand, and (c) exposing the fixed first strand and the fixed second strand to one or more oligonucleotide probes and determining whether the one or more oligonucleotide probes binds to the fixed first strand or the fixed second strand.

BRIEF DESCRIPTION OF THE DRAWINGS

FIGS. 2A and 2B collectively provide a flow chart of processes and features of a method for determining the sequence and/or structural characteristics of a target polymer in accordance with various embodiments of the present disclosure.

FIG. 3 provides a flow chart of processes and features of an additional method for determining the sequence and/or structural characteristics of a target polymer in accordance with various embodiments of the present disclosure.

FIG. 4 provides a flow chart of processes and features of an additional method for determining the sequence and/or structural characteristics of a target polymer in accordance with various embodiments of the present disclosure.

FIGS. 6A and 6B collectively illustrate an example of probes of different k-mers in length binding to a target polynucleotide in accordance with various embodiments of the present disclosure.

FIGS. 7A, 7B, and 7C collectively illustrate an example of using a reference oligo with successive cycles of oligonucleotide sets in accordance with various embodiments of the present disclosure.

FIGS. 10A and 10B collectively illustrate an example that the number of transient binding events collected correlates with the degree of localization of probe that can be achieved in accordance with various embodiments of the present disclosure.

FIGS. 11A and 11B collectively illustrate an example of tiling probes in accordance with various embodiments of the present disclosure.

FIGS. 22A, 22B, 22C, 22D, and 22E collectively illustrate examples of fluorescence in accordance with various embodiments of the present disclosure.

FIGS. 23A, 23B, and 23C collectively illustrate examples of fluorescence in accordance with various embodiments of the present disclosure.

FIG. 24 illustrates transient binding on synthetic denatured double-stranded DNA in accordance with various embodiments of the present disclosure.

DETAILED DESCRIPTION

Figure 1A:
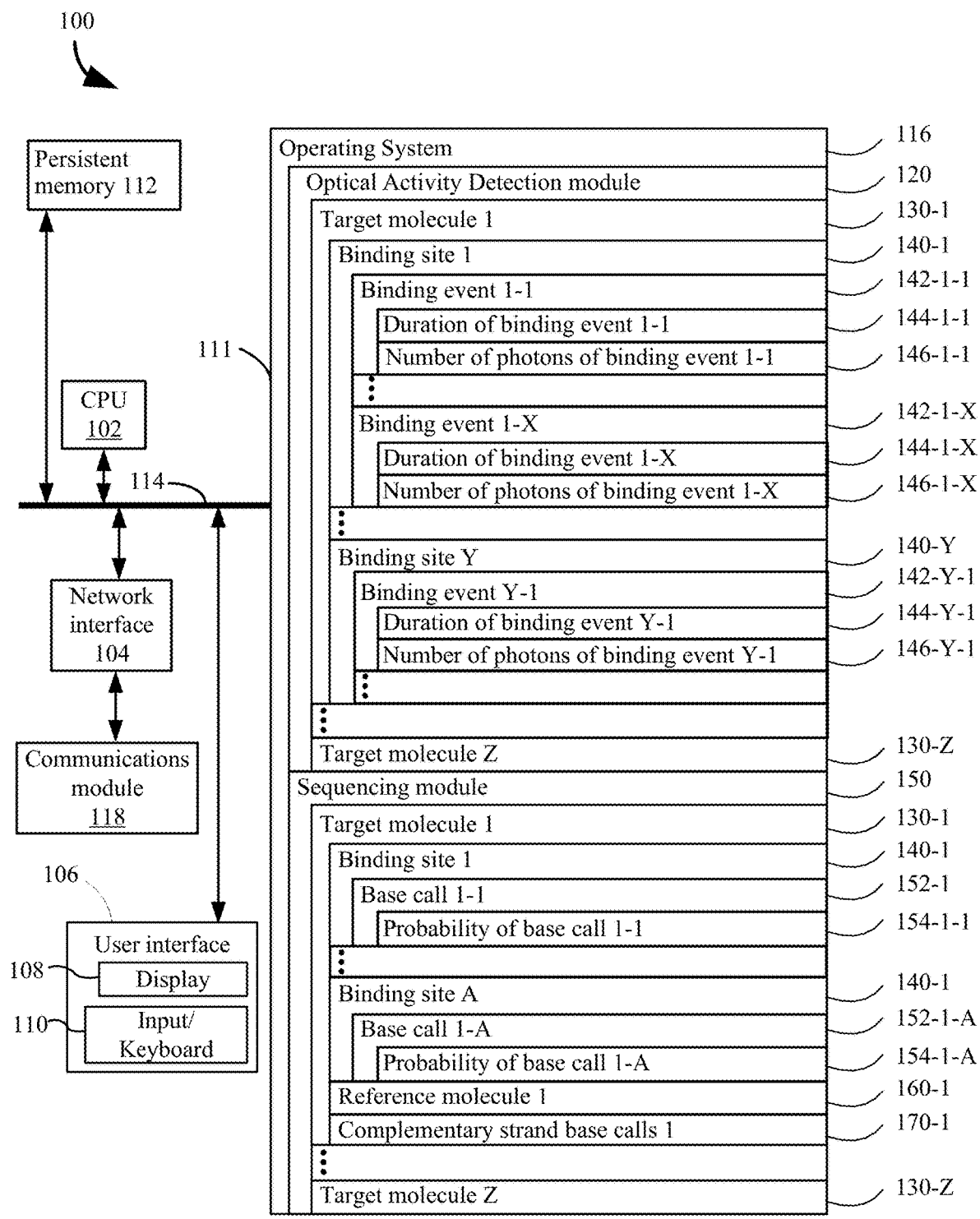
FIGS. 1A and 1B collectively illustrate an exemplary system topology that includes a polymer with multiple probes that participate in binding events, a computer storage medium to collect and store information relating to localization and sequence identification of binding events and then to further perform analysis to determine a polymer sequence in accordance with various embodiments of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Definitions

The terminology used in the present disclosure is for the purpose of describing particular embodiments only and is not intended to be limiting of the invention. As used in the description and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

As used herein, the terms "nucleic acid," "nucleic acid molecule," and "polynucleotide" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). In some instances, a nucleic acid is, or is from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample from one chromosome of a sample obtained from a diploid organism). A nucleic acid molecule can comprise the complete length of a natural polynucleotide (e.g., a long non-coding (lnc) RNA, mRNA, chromosome, mitochondrial DNA or a polynucleotide fragment). The polynucleotide fragment should be at least 200 bases in length but preferably at least several thousands of nucleotides in length. Even more preferably, in the case of genomic DNA, the polynucleotide fragment will be hundreds of kilobases to multiple megabases in length.

In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. In some embodiments, a nucleic acid is prepared using a nucleic acid obtained from a subject as a template.

As used herein the term "ending position" or "end position" (or just "end") can refer to the genomic coordinate or genomic identity or nucleotide identity of the outermost base, e.g., at the extremities, of a cell-free DNA molecule, e.g., plasma DNA molecule. The end position can correspond to either end of a DNA molecule. In this manner, if one refers to a start and end of a DNA molecule, both can correspond to an ending position. In some embodiments, one end position is the genomic coordinate or the nucleotide identity of the outermost base on one extremity of a cell-free DNA molecule that is detected or determined by an analytical method, e.g., massively parallel sequencing or next-generation sequencing, single molecule sequencing, double- or single-stranded DNA sequencing library preparation protocols, polymerase chain reaction (PCR), or microarray. In some embodiments, such in vitro techniques can alter the true in vivo physical end(s) of the cell-free DNA molecules. Thus, each detectable end can represent the biologically true end or the end is one or more nucleotides inwards or one or more nucleotides extended from the original end of the molecule e.g., 5' blunting and 3' filling of overhangs of non-blunt-ended double-stranded DNA molecules by the Klenow fragment. The genomic identity or genomic coordinate of the end position can be derived from results of alignment of sequence reads to a human reference genome, e.g., hg19. It can be derived from a catalog of indices or codes that represent the original coordinates of the human genome. It can refer to a position or nucleotide identity on a cell-free DNA molecule that is read by but not limited to target-specific probes, mini-sequencing, DNA amplification. The term "genomic position" can refer to a nucleotide position in a polynucleotide (e.g., a gene, a plasmid, a nucleic acid fragment, a viral DNA fragment). The term "genomic position" is not limited to nucleotide positions within a genome (e.g., the haploid set of chromosomes in a gamete or microorganism, or in each cell of a multicellular organism).

As used herein, the terms "mutation," "single nucleotide variant," "single nucleotide polymorphism" and "variant" refer to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation or variant generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example, of a "tissue-specific allele." For example, a tumor can have a mutation that results in an allele at a locus that does not occur in normal cells. Another example, of a "tissue-specific allele" is a fetal-specific allele that occurs in the fetal tissue, but not the maternal tissue. The term "allele" can be used interchangeably with mutation in some cases.

The term "transient binding" means that a binding reagent or probe binds reversibly to a binding site on a polynucleotide, and the probe does not usually remain attached to its binding site. This provides useful information regarding the location of binding sites during the course of analysis. Typically, one reagent or probe binds to the immobilized polymer and then detaches from the polymer after some dwell time. The same or another reagent or probe will then bind to the polymer at another site. In some embodiments, multiple binding sites along the polymer are also be bound by multiple reagents or probes at the same time. In some instances, different probes bind to overlapping binding sites. This process of reagents or probes reversibly binding to the polymer repeats many times over the course of analysis. The location, frequency, dwell time, photon emission of such binding events eventually results in a map of the chemical structure of the polymer. Indeed, the transient nature of these binding events enables the detection of an increased number of such binding events. For, if probes remained bound for long periods of time, then each probe would inhibit the binding of other probes.

The term "repetitive binding" means that the same binding site in the polymer is bound by the same binding reagent or probe or same species of binding reagent or probe multiple times during the course of an analysis. Typically, one reagent binds to the site and then dissociates, another reagent binds on and then dissociates, etc., until a map of the polymer has been developed. The repetitive binding increases the sensitivity and accuracy of the information obtained from the probes. More photons are accumulated and the multiple independent binding events increase the probability that a real signal is being detected. The sensitivity increases in cases where a signal is too low to call over background noise when only detected once. In such cases, the signal becomes callable when seen persistently (e.g., the confidence that the signal is real increases when the same signal is seen multiple times). The accuracy of binding site calls increases because multiple readings of the information confirm one reading with another.

As used herein, the term "probe" can comprise an oligonucleotide, with an optional fluorescent label attached. In some embodiments, a probe is a peptide or polypeptide, optionally labelled with fluorescent dyes or fluorescent or light scattering particles. These probes are used to determine the localization of binding sites, either to nucleic acids or to proteins.

As used herein, the terms "oligonucleotide" and "oligo" mean short nucleic acid sequences. In some instances, oligos are of defined sizes, for example, each oligo is k nucleotide bases (also referred to herein as "k-mers") in length. Typical oligo sizes are 3-mers, 4-mers, 5-mers, 6-mers, and so forth. Oligos are also referred herein as N-mers.

As used herein, the term "label" encompasses a single detectable entity (e.g. wavelength emitting entity) or multiple detectable entities. In some embodiments, a label transiently binds to nucleic acids or is bound to a probe. Different types of labels will blink in fluorescence emission, fluctuate in its photon emission, or photo-switch off and on. Different labels are used for different imaging methods. In particular, some labels are uniquely suited to different types of fluorescence microscopy. In some embodiments, fluorescent labels fluoresce at different wavelengths and also have different lifetimes. In some embodiments, background fluorescence is present in an imaging field. In some such embodiments, such background is removed from analysis by rejecting the early time window of fluorescence due to scattering. If the label is on one end of the probe (e.g., the 3' end of an oligo probe), the accuracy in localization corresponds to that end of the probe (e.g., the 3' end of the probe sequence and 5' of the target sequence). The apparent transient, fluctuating, or blinking behavior of a label can differentiate whether the attached probe is binding on and off from its binding site.

As used herein, the term "flap" refers to an entity that acts as a receptor for the binding of a second entity. The two entities can comprise molecular binding pairs. Such binding pairs can comprise nucleic acid binding pairs. In some embodiments a flap comprises a stretch of oligo- or polynucleotide sequence that binds to a labeled oligonucleotide. Such binding between a flap and an oligonucleotide should be substantially stable during the course of the process of imaging the transient binding of the part of the probe that binds the target.

The terms "elongated," "extended," "stretched," "linearized," and "straightened" can be used interchangeably. In particular, the term "elongated polynucleotide" (or "extended polynucleotide," etc.) indicates a nucleic acid molecule that has been adhered to a surface or matrix in some manner and then stretched into a linear form. Generally, these terms mean that the binding sites along the polynucleotide are separated by a physical distance more or less correlated with the number of nucleotides between them (e.g., the polynucleotide is straight). Some imprecision in the extent to which the physical distance matches the number of bases can be tolerated.

The term "imaging," as used herein, includes both two-dimensional array or two-dimensional scanning detectors. In most cases, the imaging techniques used herein will necessarily include a fluorescence activator (e.g., a laser of appropriate wavelength) and a fluorescence detector.

As used herein, the term "sequence bit" indicates one or a few bases of sequence (e.g., from 1 to 9 bases in length). In particular, in some embodiments, a sequence corresponds to the length of the oligos (or peptides) used for the transient binding. Thus, in such embodiments, a sequence refers to a region of the target polynucleotide.

As used herein, the term "haplotype" refers to a set of variations that are typically inherited in concert. This occurs because the set of variations is present in close proximity on a polynucleotide or chromosome. In some cases, a haplotype comprises one or more single nucleotide polymorphisms (SNPs). In some cases, a haplotype comprises one or more alleles.

As used herein, the term "methyl-binding proteins" refers to proteins that contain a methyl-CpG-binding domain, which comprises around 70 nucleotide residues. Such domains have low affinity for unmethylated regions of DNA, and can thus be used to identify locations in a nucleic acid that have been methylated. Some common methyl-binding proteins include MeCP2, MBD1, and MBD2. However, there are a range of different proteins that contain the methyl-CpG-binding domain (e.g., as described by Roloff et al., BMC Genomics 4:1, 2003).

As used herein, the term "nanobody" refers to a proprietary set of proteins containing heavy chain only antibody fragments. These are highly stable proteins and can be designed to have sequence homology similar to a variety of human antibodies, thus enabling specific targeting of cell type or region in the body. A review of nanobody biology can be found in Bannas et al., Frontiers in Immu. 8:1603, 2017.

As used herein, the term "affimer" refers to non-antibody binding proteins. These are highly customizable proteins, with two peptide loops and an N-terminal sequence that, in some embodiments, are randomized to provide affinity and specificity to desired protein targets. Thus, in some embodiments, affimers are used to identify sequences or structural regions of interest in proteins. In some such embodiments, affimers are used to identify many different types of protein expression, localization and interactions (e.g., as described in Tiede et al., ELife 6:e24903, 2017).

As used herein, the term "aptamer" refers to another category of highly versatile, customizable binding molecules. Aptamers comprise nucleotide and/or peptide regions. It is typical to produce a random set of possible aptamers sequences and then select for desired sequences that bind to specific target molecules of interest. Aptamers have additional characteristics beyond their stability and flexibility that make them desirable over other categories binding proteins (e.g., as described in Song et al., Sensors 12:612-631, 2012 and Dunn et al., Nat. Rev. Chem. 1:0076, 2017).

Several aspects are described below with reference to example applications for illustration. It should be understood that numerous specific details, relationships, and methods are set forth to provide a full understanding of the features described herein. One having ordinary skill in the relevant art, however, will appreciate that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Exemplary System Embodiments

Figure 1B:
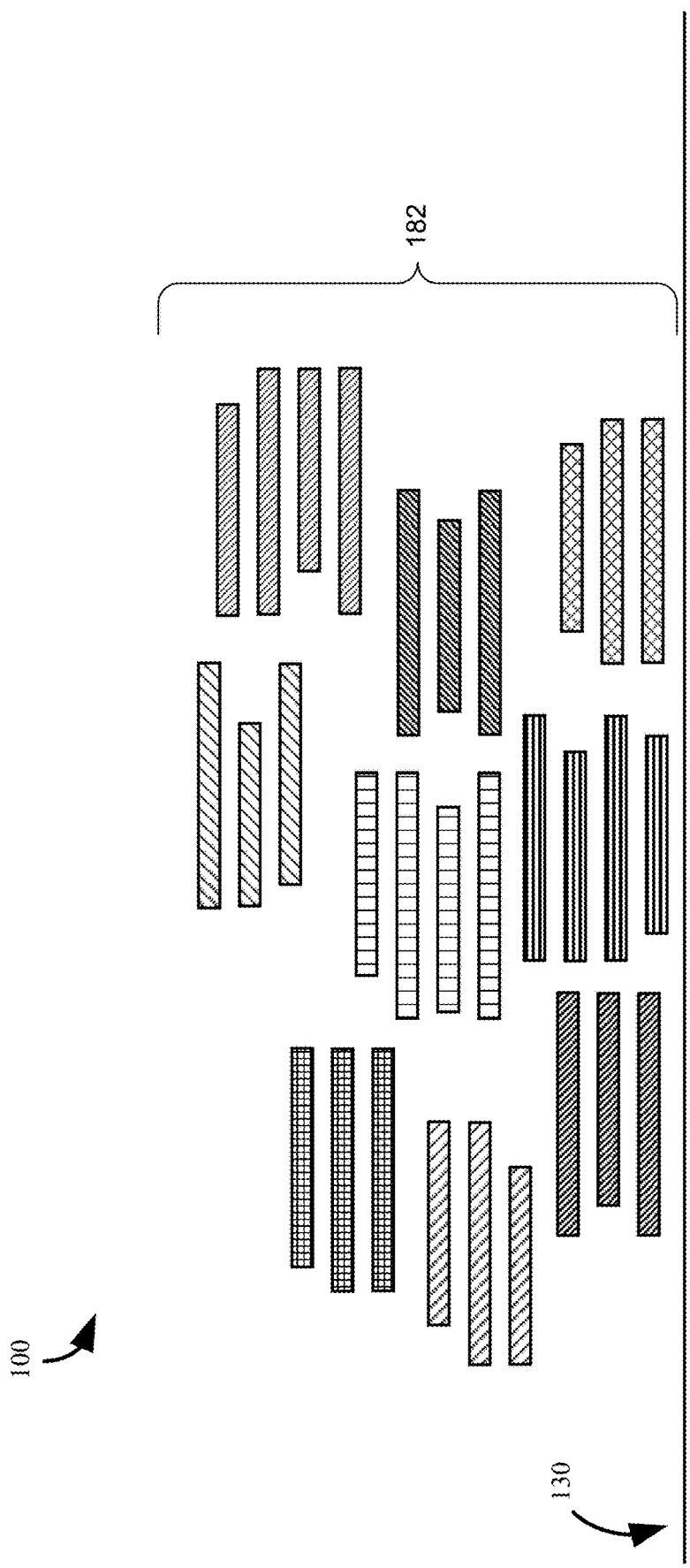

Details of an exemplary system are now described in conjunction with FIG. 1. FIG. 1 is a block diagram illustrating a system 100 in accordance with some implementations. The device 100 in some implementations includes one or more processing units (CPU(s)) 102 (also referred to as processors or processing core), one or more network interfaces 104, a user interface 106, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:

- an optional operating system 116, which includes procedures for handling various basic system services and for performing hardware dependent tasks;
- an optional network communication module (or instructions) 118 for connecting the system 100 with other devices, or a communication network;
- an optical activity detection module 120 for collecting information for each target molecule 130;
- information for each respective binding site 140 in a plurality of binding sites for each target molecule 130;
- information for each respective binding event 142 in a plurality of binding events for each binding site 140 including at least (i) the duration 144 and (ii) the number of photons emitted 146;
- a sequencing module 150 for determining a sequence of each target molecule 130;
- information for each respective binding site 140 in the plurality of binding sites for each target molecule 130 including at least (i) a base call 152 and (ii) a probability 154;
- optional information regarding a reference genome 160 for each target molecule 130; and
- optional information regarding a complementary strand 170 for each target molecule 130.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Examples of network communication modules 118 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Although FIG. 1 depicts a "system 100," the figure is intended more as functional description of the various features that may be present in computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112. Furthermore, in some embodiments the memory 111 and/or 112 stores additional modules and data structures not described above.

While a system in accordance with the present disclosure has been disclosed with reference to FIG. 1, methods in accordance with the present disclosure are now detailed with reference to FIGS. 2A, 2B, 3 and 4.

Block 202. A method of determining the chemical structure of a molecule is provided. A goal of the present disclosure is to enable single nucleotide resolution sequencing of a nucleic acid. In some embodiments, a method of characterizing interactions between one or more probes and a molecule are provided. The method includes adding one or more probe species to the molecule under conditions that cause the one or more probe species to transiently bind to the molecule. The method proceeds by continuously monitoring individual binding events on the molecule on a detector and recording each binding event over a period of time. The data from each binding event is analyzed to determine one or more characteristics of the interactions.

In some embodiments, a method of determining the identity of a polymer is provided. In some embodiments, a method of determining the identity of a cell or tissue is provided. In some embodiments, a method of determining the identity of an organism is provided. In some embodiments, a method of determining the identity of an individual is provided. In some embodiments, the methods are applied to single cell sequencing.

Target Polymers.

In some embodiments, the molecule is a nucleic acid, preferably a native polynucleotide. In various embodiments, the method further comprises extracting the single target polynucleotide molecule from a cell, organelle, chromosome, virus, exosome or body fluid as an intact target polynucleotide.

In some embodiments, the polymer is a short polynucleotide (e.g., <1 kilobases or <300 bases). In some embodiments, the short polynucleotide is 100-200 bases, 150-250 bases, 200-350 bases, or 100-500 bases in length, as is found for cell-free DNA in body fluids such as urine and blood.

In some embodiments, the nucleic acid is at least 10,000 bases in length. In some embodiments, the nucleic acid is at least 1,000,000 bases in length.

In various embodiments, the single target polynucleotide is a chromosome. In various embodiments, the single target polynucleotide is about $10^2$, $10^3$, $10^4$, $10^5$, $10^6$, $10^7$, $10^8$ or $10^9$ bases in length.

In some embodiments, the method enables analysis of amino-acid sequence on a target protein. In some embodiments, a method for analyzing amino acid sequence on a target polypeptide is provided. In some embodiments, a method for analyzing peptide modifications as well amino-acid sequence on a target polynucleotide is provided. In some embodiments the molecular entity is a polymer, comprising at least 5 units. In such embodiments the binding probes are molecular probes comprising oligonucleotides, antibodies, affimers, nanobodies, aptamers binding proteins, or small molecules, etc.

In such embodiments, each of the 20 amino acids is bound by a corresponding specific probe comprising an N-recognin, nanobody, antibody, aptamer, etc. The binding of each probe is specific to each corresponding amino acid within the polypeptide chain. In some embodiments, the order of sub-units in a polypeptide is determined. In some embodiments, the binding is to surrogates of the binding sites. In some embodiments, the surrogates are tags attached at certain amino acids or peptide sequences, and the transient binding will be to the surrogate tags.

In some embodiments, the molecule is a heterogeneous molecule. In some embodiments, the heterogeneous molecule comprises a supramolecular structure. In some embodiments, the method enables identifying and ordering the units of chemical structure for a heterogeneous polymer. Such embodiments comprise elongating the polymer and binding a plurality of probes to identify the chemical structure at a plurality of sites along the elongated polymer. Elongating the heteropolymer permits sub-diffraction level (e.g., nanometric) localization of probe binding sites.

In some embodiments, methods for sequencing polymers by the binding of probes that recognize subunits of the polymer are provided. Typically, the binding of one probe is not sufficient to sequence the polymer. For example, FIG. 1A an embodiment where the sequencing of the polymer 130 is based on measuring transient interactions with a repertoire of probes 182 (e.g., the interaction of a denatured polynucleotide with a repertoire of oligonucleotides or the interaction of a denatured polypeptide with a panel of nanobodies or affimers).

Extraction and/or Preparation of Target Polymers.

In some embodiments, it is necessary to separate cells that are of interest from others that are not before nucleic acid extraction is conducted. In one such example, circulating tumor cells or circulating fetal cells are isolated from blood (e.g., by using cellular surface markers for affinity capture). In some embodiments, it is necessary to separate microbial cells from human cells, where the interest is to detect and analyse polynucleotides from the microbial cells. In some embodiments, Opsonins are used to affinity capture a wide-range of microbes and separate them from mammalian cells. In addition, in some embodiments, differential lysis is performed. The mammalian cells are lysed first, under relatively gentle conditions. Microbial cells are typically hardier than mammalian cells, and hence they remain intact through the lysis of the mammalian cells. The lysed mammalian cell fragments are washed away. Then harsher conditions are used to lyse microbial cells. The target microbial polynucleotides are then selectively sequenced.

In some embodiments, the target nucleic acid is extracted from a cell prior to sequencing. In alternate embodiments, the sequencing (e.g., of chromosomal DNA) is conducted inside a cell where the chromosomal DNA follows a convoluted path during interphase. The stable binding of oligos in situ has been demonstrated by Beliveau et al., Nature Communications 6:7147 (2015). Such in situ binding of oligos and their nanometic localization in three-dimensional space enables the determination of the sequence and structural arrangement of a chromosomal molecule within the cell.

The target polynucleotides are often present in native folded states. In one such example, genomic DNA is highly condensed in chromosomes, while RNA forms secondary structures. In some embodiments, long lengths of polynucleotide are obtained (e.g., by preserving substantially native lengths of the polynucleotides) during extraction from a biological sample. In some embodiments, the polynucleotide is linearized such that locations along its length are traced with little or no ambiguity. Ideally, the target polynucleotide is straightened, stretched or elongated, either before or after being linearized.

The methods are particularly suited to sequence very long polymer lengths, where native lengths or a substantial proportion thereof are preserved (e.g., for DNA whole chromosomes or ~1 megabase fractions). However, common molecular biology methods result in unintended fragmentation of DNA. For instance, pipetting and vortexing causes shear forces that break DNA molecules. Nuclease contamination can cause nucleic acids to be degraded. In some embodiments, native lengths or substantial high molecular weight (HMW) fragments of native lengths are preserved before immobilization, stretching and sequencing commences.

In some embodiments, the polynucleotides are intentionally fragmented to relatively homogeneous long lengths (e.g., ~1 Mb in length) before proceeding with sequencing. In some embodiments, the polynucleotides are fragmented to relatively homogeneous long lengths after or during fixing or elongations. In some embodiments, the fragmentation is effected enzymatically. In some embodiments, the fragmentation is effected physically. In some embodiments, the physical fragmentation is via sonication. In some embodiments, the physical fragmentation is via ionic bombardment or radiation. In some embodiments, the physical fragmentation is via electromagnetic radiation. In some embodiments, the physical fragmentation is via UV illumination. In some embodiments, the dose of the UV illumination is controlled to effect fragmentation to a given length. In some embodiments, the physical fragmentation is via the combination of UV illumination and staining with a dye (e.g., YOYO-1). In some embodiments, the fragmentation process is halted by a physical action or addition of a reagent. In some embodiments, the reagent that effects a halt in the fragmentation process is a reducing agent such as beta-mercaptoethanol (BME).

Fragmenting by Dose of Radiation and Sequencing

When the field of view of the two-dimensional sensor allows the complete megabase length of DNA to be viewed in one dimension of the sensor, then it is efficient to produce genomic DNA in lengths of 1 Mb. It should also be noted that reducing the size of chromosome length fragments also minimizes the tangling of strands, and to get the maximum length of DNA in a stretched well-isolated form.

A method for sequencing long sub-fragments of a chromosome comprising the following steps:
i) Staining chromosomal double stranded DNA with a dye, said dye intercalating between base pairs of the double-strand
ii) Exposing stained chromosomal DNA to a pre-determined dose of electromagnetic radiation to create sub-fragments of the chromosomal DNA within a desired size range
iii) Elongating and fixing stained chromosomal sub-fragments DNA on surface
iv) Denaturing stained chromosomal sub-fragments to disrupt the base-pairs and thereby releasing the intercalating dye
v) Exposing the resulting de-stained, elongated, fixed, single-strands to a repertoire of oligonucleotides of a given length and sequence
vi) Determining the location of binding o along the de-stained elongated single strands of each oligonucleotide in the repertoire
vii) Compiling the locations of binding of all oligos in the repertoire to obtain a full sequencing of the chromosomal sub-fragment.

In some embodiments of the above, staining occurs when the chromosome is in a cell. In some embodiments of the above, the labelled oligonucleotide is only labeled because more stain is added and intercalates into the duplex when the duplex forms. In some embodiments of the above, optionally in addition to the denaturing, a dose of electromagnetic radiation capable of bleaching the stain is applied. In some embodiments of the above, said pre-determined dose is achieved by manipulating the strength and duration of the exposing and the stopping of the fragmenting by a chemical exposure, where said chemical exposure is a reducing agent such as beta-mercaptoethanol. In some embodiments of the above, the dose is pre-determined to produce a Poisson distribution around 1 Mb length of fragments Methods of Fixation and Immobilization.

Block 204.

The nucleic acid is fixed in a double-stranded linearized stretched form on a test substrate, thereby forming a fixed stretched double-stranded nucleic acid. Optionally, the molecule is immobilized on a surface or matrix. In some embodiments, fragmented or native polymers are fixed. In some embodiments, the fixed double-stranded linearized nucleic acid is not straight but rather follows a curvilinear or tortuous path.

In some embodiments, the fixing comprises applying the nucleic acid to the test substrate by molecular combing (receding meniscus), flow stretching, nanoconfinement, or electro-stretching. In some embodiments, the application of nucleic acid to the substrate further includes a UV cross-linking step, where the nucleic acid is covalently bonded to the substrate. In some embodiments, the application does not require UV crosslinking of the nucleic acid, and the nucleic acid is bonded to the substrate through other means (e.g., such as hydrophobic interactions, hydrogen bonding, etc.).

Immobilizing (e.g., fixing) the polynucleotide at just one end, permits the polynucleotide to stretch and contract in uncoordinated ways. Thus, whatever method of elongation is used, the degree of stretching along the length of the polymer cannot be guaranteed for any particular position in the target. In some embodiments, it is necessary that the relative positions of multiple locations along the polymer are not subject to fluctuation. In such embodiments, the elongated molecule should be immobilized or fixed to the surface by multiple points of contact along its length (e.g., as is done in the molecular combing technique of Michalet et al, Science 277:1518-1523, 1997; see also Molecular Combing of DNA: Methods and Applications, Journal of Self-Assembly and Molecular Electronics (SAME) 1:125-148) for stretching on a surface can be used (e.g. ACS Nano. 2015 Jan. 27; 9(1):809-16).).

In some embodiments, an array of polynucleotides is immobilized on the surface and in some embodiments, the polynucleotides of the array are far enough apart to be individually resolved by diffraction-limited imaging. In some embodiments, the polynucleotides are rendered on the surface in an ordered manner, so that the molecules are maximally packed within a given surface area and that they do not overlap. In some embodiments, this is done by making a patterned surface (e.g., an ordered arrangement of hydrophobic patches or strips at such locations to which the ends of a polynucleotide will bind). In some embodiments, the polynucleotides of the array are not far enough apart to be individually resolved by diffraction limited imaging and are individually resolved by super-resolution methods.

In some embodiments, the polynucleotides are organized in DNA Curtains (Greene et al., Methods Enzymol. 472: 293-315, 2010). This is particularly useful for long polynucleotides. In such embodiments, the transient binding is recorded while the DNA strands, attached at one end are elongated by flow or electrophoretic forces or after both ends of the strand have been captured. In some embodiments, where many copies of the same sequence form the plurality of polynucleotides in the DNA curtain, the sequence is assembled from the binding pattern in aggregate from the plurality of polynucleotides rather than from one polynucleotide. In some embodiments, both ends of the polynucleotide bind to pads (e.g., regions of the surface that will stick to the polynucleotide more than other sections of the surface), each end to a different pad. In such embodiments, the two pads that a single linear polynucleotide binds to hold the stretched configuration of the polynucleotide in place and allow an ordered array of equally spaced, non-overlapping or non-interacting polynucleotides to be formed. In some embodiments, only one polynucleotide occupies an individual pad. In some embodiments, where the pads are populated using a Poisson process, some pads are occupied by no polynucleotides, some by one, and some by more than one.

In some embodiments, the target molecules are captured onto an ordered supramolecular scaffold (e.g., DNA Origami structure). In some embodiments, the scaffold structure starts free in solution to take advantage of solution phase kinetics for capturing target molecules. Once they are occupied, the scaffolds settle or self-assemble onto the surface and are locked down on surface. The ordered array enables efficient sub-diffraction packing of molecules allowing higher density of molecules (high density array) per field of view. Single molecule localization methods allow the polynucleotides within the high density array to be super-resolved (e.g., to distances 40 nm or less point to point).

In some embodiments, a hairpin is ligated (optionally after polishing the end of the nucleic acid) onto the end of duplex template. In some embodiments, the hairpin contains a biotin that immobilizes the nucleic acid to the surface. In alternative embodiments, the hairpin serves to covalently link the two strands of the duplex. In some such embodiments, the other end of the nucleic acid is tailed for surface capture by olio d(T) for example. After denaturation both strands of the nucleic acid are available for interaction with oligos.

In some embodiments, the ordered array takes the form of individual scaffolds that link together to form a large DNA lattice (e.g., as described in Woo and Rothemund, Nature Communications, 5: 4889). In some such embodiments, individual small scaffolds lock on to one another by base-pairing. They then present a highly ordered nanostructured array for sequencing steps of the present disclosure. In some embodiments, capture sites are arranged at a 10 nm pitch in an ordered two-dimensional lattice. With full occupancy such a lattice has the capability of capturing on the order of one trillion molecules per square centimeter.

In some embodiments, capture sites in a lattice are arranged at a 5 nm pitch, a 10 nm pitch, a 15 nm pitch, a 30 nm pitch, or a 50 nm pitch in an ordered two-dimensional lattice. In some embodiments, capture sites in a lattice are arranged at between a 5 nm pitch and a 50 nm pitch in an ordered two-dimensional lattice.

In some embodiments, an ordered array is created using nanofluidics. In one such example, an array of nanotrenches or nanogrooves (e.g., 100 nm wide and 150 nm deep) are textured on the surface and serve to order the long polynucleotides. In such embodiments, the occurrence of one polynucleotide in a nanotrench or nanogroove excludes the entry of another polynucleotide. In another embodiment, a nanopit array is used, where segments of long polynucleotides are in the pits and intervening long segments are spread between the pits.

In some embodiments, a high density of polynucleotides still permits super-resolution imaging and precise sequencing. For example, in some embodiments, only a subset of the polynucleotide is of interest (e.g., targeted sequencing). In such embodiments, only a subset of polynucleotides from the complex sample (e.g., whole genome or transcriptome) need to be analyzed when targeted sequencing is done, and the polynucleotides deposited on the surface or matrix at a higher density than usual. In such embodiments, even when there are several polynucleotides present within a diffraction limited space, when a signal is detected, there is high probability that it is from only one of the targeted loci and that this locus is not within a diffraction limited distance of another such locus that is simultaneously bound to a probe. The required distance between each polynucleotide undergoing targeted sequencing is correlated to the percentage of the polynucleotide that is targeted. For example, if <5% of the polynucleotide is targeted, then the density of polynucleotides is twenty times greater than if the entire polynucleotide sequence is desired. In some embodiments of targeted sequencing, the imaging time is shorter than in the case where the whole genome is to be analyzed (e.g., in the example above, the targeted sequencing imaging could be 10× faster than whole genome sequencing).

In some embodiments, the test substrate is bound with a sequence-specific oligonucleotide probe prior to the fixing, and the fixing comprises capturing the nucleic acid on the test substrate using a sequence-specific oligonucleotide probe bound to the test substrate. In some embodiments, the nucleic acid is bound at the 5' end. In some embodiments, the nucleic acid is bound at the 3' end. In another embodiment, where there are two separate probes on the substrate, one probe will bind to the first end of the nucleic acid and the other probe will bind to the second end of the nucleic acid. In cases, where two probes are used, it is also necessary to have prior information on the length of the nucleic acid. In some embodiments, the nucleic acid is first cut with a predetermined endonuclease.

In various embodiments, prior to fixation, the target polynucleotide is extracted into or embedded in a gel or matrix (e.g., as described in to Shag et al., Nature Protocols 7:467-478, 2012). In one such non-limiting example, the polynucleotides are deposited in a flow channel containing a medium that undergoes a liquid to gel transition. The polynucleotides are initially elongated and distributed in the liquid phase and then fixed by changing phase to the solid/gel phase (e.g., by heating, or in the case of polyacrylamide by adding a co-factor or with time). In some embodiments, the polynucleotides are elongated in the solid/gel phase.

In some alternative embodiments, the probes themselves are immobilized on the surface or matrix. In such embodiments, one or more target molecules (e.g., the polynucleotide) are suspended in solution and bind transiently to the fixed probes. In some embodiments, a spatially addressable array of oligonucleotides is used to capture polynucleotides. In some embodiments, short polynucleotides (e.g., <300 nucleotides) such as cell-free DNA or microRNA or relatively short polynucleotides (e.g., <10,000 nucleotides) such as mRNA are immobilized randomly on a surface, by capturing a modified or non-modified end using an appropriate capture molecule. In some embodiments, short or relatively short polynucleotides make multiple interactions with the surface, and sequencing is carried out in a direction parallel to the surface. This allows splicing isoformic organization to be resolved. For example, in some isoforms, the location of exons that are repeated or shuffled are delineated.

In some embodiments, the immobilized probes contain a common sequence that anneals to the polynucleotides. Such an embodiment is particularly useful when the target polynucleotides have a common sequence, preferably at one or both ends. In some embodiments, the polynucleotide is single stranded and has a common sequence, such as a polyA tail. In one such example, native mRNA carrying polyA tails are captured on a lawn of oligo d(T) probes on a surface. In some embodiments, especially those where short DNA is analyzed, the ends of the polynucleotide are adapted for interaction with capture molecules on a surface/matrix.

In some embodiments, the polynucleotides are double stranded with sticky ends generated by a restriction enzyme. In some non-limiting examples, restriction enzymes with infrequent sites (e.g., Pmme1 or NOT1) are used to generate long fragments of the polynucleotide, each fragment containing a common end sequence. In some embodiments, the adaptation is performed using terminal transferase. In other embodiments, ligation or tagmentation is used to introduce adaptors for Illumina sequencing. This enables users to use the well-established Illumina protocols to prepare the samples, which are then captured and sequenced by the methods described herein. In such embodiments, the polynucleotides are preferably captured before amplification, which has the tendency to introduce error and bias.

Methods of Elongation

In most embodiments, a polynucleotide or other target molecule must be attached to a surface or matrix for elongation to occur. In some embodiments, elongation of the nucleic acid renders it equal to, longer or shorter than its crystallographic length (e.g., where there is a known 0.34 nm separation from one base to the next). In some embodiments, the polynucleotide is stretched beyond the crystallographic length.

In some embodiments, the polynucleotide is stretched via molecular combing (e.g., as described in Michalet et al., Science 277:1518-1523, 1997 and Deen et al., ACS Nano 9:809-816, 2015). This enables the stretching and unidirectional aligning of millions and billions of molecules in parallel. In some embodiments, molecular combing is performed by washing a solution containing the desired nucleic acid onto a substrate and then retracting the meniscus of the solution. Prior to retracting the meniscus, the nucleic acid forms covalent or other interactions with the substrate. As the solution recedes, the nucleic acid is pulled in the same direction as the meniscus (e.g., through surface retention); however, if the strength of the interactions between the nucleic acid and the substrate is sufficient to overcome the surface retention force, then the nucleic acid is stretched in a uniform manner in the direction of the receding meniscus. In some embodiments, the molecular combing is performed as described in Kaykov et al., Sci Reports. 6:19636 (2016), which is hereby incorporated by reference in its entirety. In other embodiments, the molecular combing is performed in channels (e.g., of a microfluidic device) using methods or modified versions of methods described in Petit et al. Nano Letters 3:1141-1146 (2003).

The shape of the air/water interface determines the orientation of the elongated polynucleotides that are stretched by molecular combing. In some embodiments, the polynucleotide is elongated perpendicular to the air/water interface. In some embodiments, the target polynucleotide is attached to a surface without modification of one or both of its termini. In some embodiments, where the ends of a double-stranded nucleic acid are captured by hydrophobic interactions, the stretching with a receding meniscus makes parts of the duplex denature and form further hydrophobic interactions with the surface.

In some embodiments, the polynucleotide is stretched via molecular threading (e.g., as described by Payne et al., PLoS ONE 8(7):e69058, 2013). In some embodiments the molecular threading is done after the target has been denatured into single strands (e.g., by chemical denaturants, temperature or enzymes). In some embodiments the polynucleotide is tethered at one end and then stretched in fluid flow (e.g., as illustrated in Greene et al., Methods in Enzymology, 327: 293-315).

In various embodiments, the target polynucleotide molecule is present within a microfluidic channel. In one such example, the polynucleotide is flowed into the microfluidic channel or is extracted from one or more chromosome, exosomes, nuclei, or cells into a flow channel. In some embodiments, rather than inserting polynucleotide into nanochannels via a micro- or nanofluidic flow cell, polynucleotides are inserted into open-top channels by constructing the channel in such a way that the surface on which the walls of the channel are formed, is electrically biased (e.g., see Asanov et al., Anal Chem. 1998 Mar. 15; 70(6):1156-6). In one such example, a positive bias is applied to the surface, so that the negatively charged polynucleotide is attracted into the nanochannel. Concurrently, the ridges of the channel walls do not contain a bias, so that the polynucleotide will be less likely to deposit on the ridges themselves.

In some embodiments, the extension is due to hydrodynamic drag. In one such example, the polynucleotide is stretched via a crossflow in a nanoslit (Marie et al., Proc Natl Acad Sci USA 110:4893-8, 2013). In some embodiments, the extension of the nucleic acid is due to nanoconfinement in a flow channel. Flow stretching nanoconfinement involves stretching a nucleic acid into a linear conformation via flow gradients, generally performed within a microfluidic device. The nanoconfinement portion of this stretching method typically refers to a narrow region of the microfluidic device. The use of a narrow region or channel helps overcome the issue of molecular individualism (e.g., the tendency of an individual nucleic acid or other polymer to adopt multiple conformations during stretching). One problem with flow stretching methods is that the flow is not always applied equally along a nucleic acid molecule. This can result in a nucleic acids exhibiting a wide range of extension lengths. In some embodiments, flow stretching methods involve extensional flow and/or hydrodynamic drag. In some embodiments where the polynucleotide is attracted into the nanochannel, one or more polynucleotides are nanoconfined in the channel, and thereby elongated. In some embodiments, after nanoconfinement the polynucleotide is deposited on the biased surface or on a coating or matrix atop the surface.

There are multiple methods of applying a positive or a negative bias to a surface. In one such example, the surface is made with or is coated with a material that has non-fouling characteristics, or is passivated with lipids (e.g., lipid bilayers), bovine serum albumin (BSA), casein, various PEG derivatives, etc. Passivation serves to prevent polynucleotide sequestration in any one part of a channel and thus to enable elongation. In some embodiments, the surface also comprises indium tin oxide (ITO).

In some embodiments, for the creation of lipid bilayers (LBLs) on the surface of nanofluidic channels zwitterionic POPC (1-palmitoyl-2-oleoyl-sn-glycero-3-phosphocholine) lipids with 1% Lissamine™ rhodamine B 1,2-dihexadecanoyl-sn-glycero-3-phosphoethanolamine is coated onto a surface. The addition of triethylammonium salt (rhodamine-DHPE) lipids enables observation of the LBL formation with fluorescence microscopy. Methods of lipid bilayer passivation that are used in some embodiments of the present disclosure are described by Persson et al., Nano Lett. 12:2260-2265, 2012

In some embodiments, extension of the one or more polynucleotides is performed via electrophoresis. In some embodiments, the polynucleotide is tethered at one end and then stretched by an electric field (e.g., as described by Giese et al., Nature Biotechnology 26: 317-325, 2008). Electro-stretching of nucleic acid is predicated upon the fact that nucleic acids are highly negatively charged molecules. The method of electro-stretching, for example, as described by Randall et al. 2006, Lab Chip. 6, 516-522, involves nucleic acid being drawn through a microchannel (to induce orientation of the nucleic acid molecule) by an electric current. In some embodiments, electro-stretching is conducted either within or without a gel. One benefit of using a gel is to limit the three-dimensional space available to the nucleic acid, thus helping to overcome molecular individualism. A general advantage of electro-stretching over pressure-driven stretching methods such as nanoconfinement is the lack of shear forces that break nucleic acid molecules.

In some embodiments, when a plurality of polynucleotides is present on one surface, the polynucleotides are not aligned in the same orientation or are not straight (e.g., the polynucleotides attach to the surface or have threaded through a gel in a curvilinear path). In such embodiments, there is as increased likelihood that two or more of the plurality of polynucleotides will overlap, leading to confusion regarding the localization of probes along the length of each polynucleotide. Although, the same sequencing information is obtained from curved sequences as from straight well-aligned molecules, the image processing task of processing sequencing information from curved sequences requires more computational power than that obtained from straight well-aligned molecules.

In embodiments where the one or more polynucleotides are elongated in a direction parallel to a planar surface, their lengths are imaged across an adjacent series of pixels in a two-dimensional array detector such as a CMOS or CCD camera. In some embodiments, the one or more polynucleotides are elongated in a direction perpendicular to the surface. In some embodiments, the polynucleotides are imaged via light sheet microscopy, spinning disk confocal microscopy, three-dimensional super resolution microscopy, three-dimensional single molecule localization, or laser scanning disc confocal microscopy or its variants. In some embodiments, the polynucleotide is elongated at an oblique angle to the surface. In some embodiments, the polynucleotides many be imaged via a two-dimensional detector and the images processed via a Single Molecule Localization algorithm software (e.g., the Fiji/ImageJ plug-in ThunderSTORM as described in Ovesny et al., BioInform. 30:2389-2390, 2014).

Extracting and Isolating DNA from a Single Cell Prior to Fixing and Elongation.

In some embodiments, traps for single cells are designed within microfluidic structures to hold individual cells in one place while their nucleic acid content is released (e.g., by using the device designs of WO/2012/056192 or WO/2012/055415). In some embodiments, instead of extracting and stretching the polynucleotide in nanochannels, the coverglass or foil used to seal the micro/nanofluidic structures is coated with polyvinylsilane to enable molecular combing (e.g., by movements of fluids as described by Petit et al., Nano Letters 3:1141-1146. 2003). The gentle conditions inside the fluidic chip enables extracted polynucleotides to be preserved in long lengths.

A number of different approaches are available for extracting biopolymers from single cells or nuclei (e.g., some suitable methods are reviewed in Kim et al., Integr Biol 1(10), 574-86, 2009). In some non-limiting examples, cells are treated with KCL to remove cell membranes. Cells are lysed by adding a hypotonic solution. In some embodiments, each cell is separately isolated, each cell's DNA is separately extracted, and then each set of DNA is separately sequenced in a microfluidic vessel or device. In some embodiments, the extraction occurs by treating the one or more cells with detergent and/or protease. In some embodiments, chelating agents (e.g., EDTA) are provided in the lysis solution to capture divalent cations required by nucleases (and thus decrease nuclease activity).

In some embodiments, the nuclear and extra nuclear constituents of a single cell are separately extracted by the following method. One or more cells are provided to the feeding channel of a microfluidic device. The one or more cells are then captured, where each cell is captured by one trapping structure. A first lysis buffer is added to the solution, where the first lysis buffer lyses the cellular membrane but helps preserve the integrity of the cell nuclei. Upon addition of the first lysis buffer the extra nuclear constituents of the one or more cells are released into a flow cell where the released RNA is immobilized. The one or more nuclei are then lysed by supplying a second lysis buffer. The addition of the second lysis buffer causes the release of the constituents of the one or more nuclei (e.g., genomic DNA) into a flow cell where the DNA is subsequently immobilized. The extra and intracellular components of the one or more cells is immobilized at different locations of the same flow cell or in different flow cells within the same device.

Figure 16A:
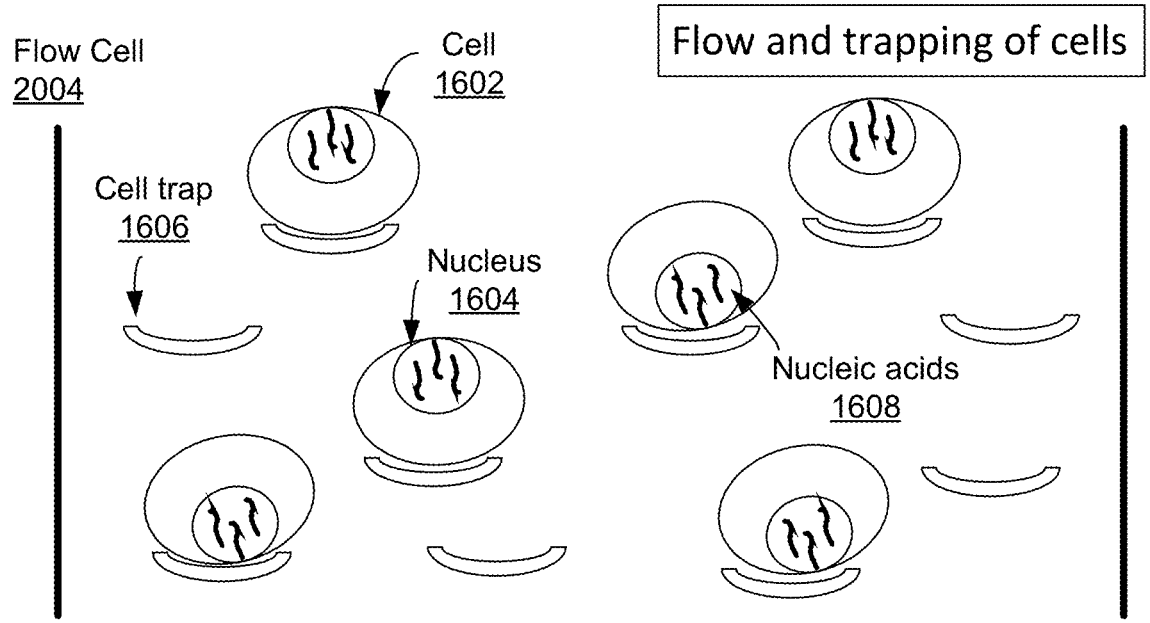
FIGS. 16A and 16B collectively illustrate an example of cell lysis and nucleic acid immobilization and elongation in accordance with various embodiments of the present disclosure.
Figure 16B:
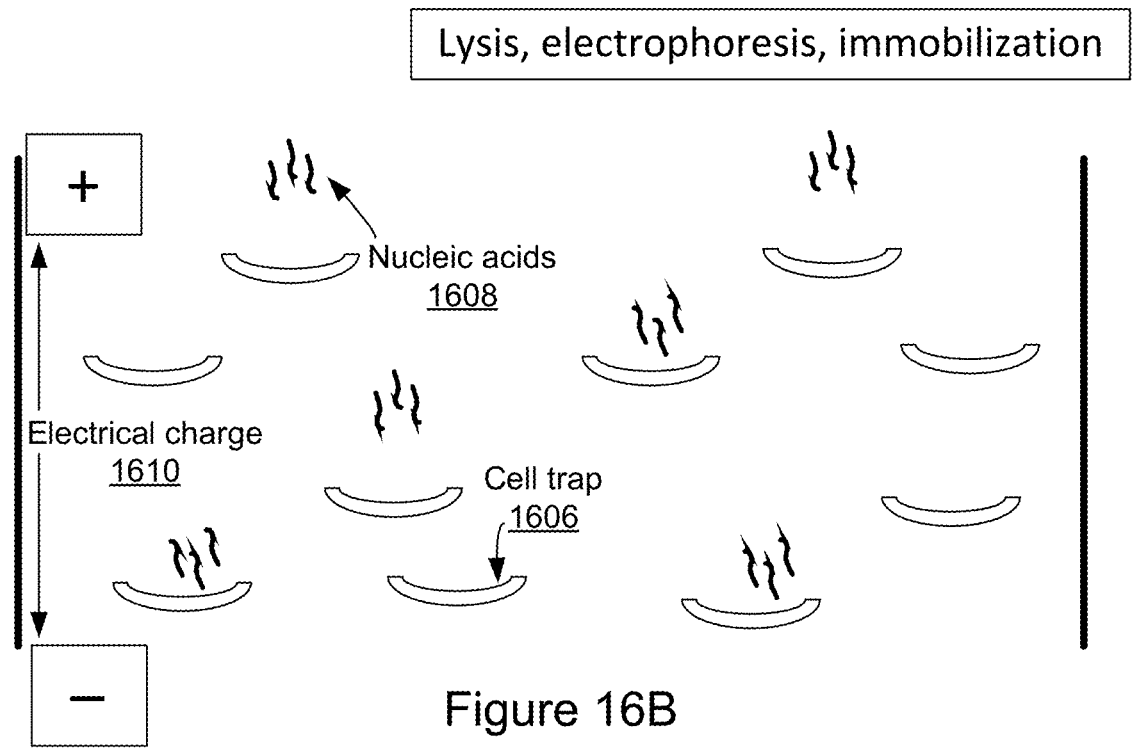

The schematic in FIGS. 16A and 16B shows a microfluidic architecture that captures and isolates multiple single cells. Cells 1602 are captured by cell traps 1606 within the flow cell 2004. In some embodiments, after the cells have been captured, lysis reagents are flowed through. After lysis, the polynucleotides are then distributed close to the capture regions, while remaining isolated from polynucleotides extracted from other cells. In some embodiments, as illustrated in FIG. 16B, electrophoretic induction is performed (e.g., by using electrical charge 1610) to maneuver nucleic acids. Lysis will release nucleic acids 1608 from the cells 1602 and the nuclei 1604. The nucleic acids 1608 remain in the position (e.g., relative to the cell traps 1606) in which they were when the cells 1602 were trapped. The traps are the dimension of single cells (e.g., from 2-10 uM). In some embodiments, the channels bringing the microdroplet and cell together are >2 uM or 10 uM. In some embodiments, the distance between the bifurcating channels and traps is 1-1000 microns.

Extracting and Elongating High Molecular Weight DNA on a Surface.

Various methods for stretching HMW polynucleotide are used in different embodiments (e.g., ACS Nano. 9(1):809-16, 2015). In one such example, elongation on a surface is conducted in a flow cell (e.g., by using the approach described by Petit and Carbeck in Nano. Lett. 3: 1141-1146, 2003). In addition to fluidic approaches, in some embodiments polynucleotides are stretched using an electric field such as disclosed in Giess et al., Nature Biotechnology 26, 317-325 (2008). Several approaches are available for elongating polynucleotides when they are not attached to a surface (e.g., Frietag et al., Biomicrofluidics, 9(4):044114 (2015); Marie et al., Proc Natl Acad Sci USA 110:4893-8, 2013).

As an alternative to using DNA in a gel plug, chromosomes suitable for loading onto the chip are prepared by the poly amine method as described by Cram et al., Methods Cell Sci., 2002, 24, 27-35, and pipetted directly into the device. In some such embodiments, the proteins binding to DNA in a chromosome are digested using a protease to release substantially naked DNA, which is then be fixed and elongated as described above.

Treating Samples for Locational Preservation of Reads.

In embodiments where very long regions or polymers are to be sequenced, any degradation of the polymer has the potential to significantly decrease the accuracy of the overall sequencing. Methods to facilitate preservation of the entire elongated polymer are presented below.

A polynucleotide has the potential to become damaged during extraction, storage or preparation. Nicks and adducts can form in a native double-stranded genomic DNA molecule. This is especially the case for when the sample polynucleotides are from FFPE material. Thus, in some embodiments, a DNA repair solution is introduced before or after DNA is immobilized. In some embodiments, this is done after DNA extraction into a gel plug. In some embodiments, the repair solution contains DNA endonuclease, kinases and other DNA modifying enzymes. In some embodiments, the repair solution comprises polymerases and ligases. In some embodiments, the repair solution is the pre-PCR kit form New England Biolabs. In some embodiments, such methods are performed largely as described in Karimi-Busheri et al., Nucleic Acids Res. October 1; 26(19): 4395-400, 1998 and Kunkel et al., Proc. Natl Acad Sci. USA, 78, 6734-6738, 1981.

In some embodiments, after the polynucleotide is elongated a gel overlay is applied. In some such embodiments, after elongation and denaturation on the surface, the polynucleotide (double-stranded or denatured) is covered with a gel layer. Alternatively, the polynucleotide is elongated while already in a gel environment (e.g., as described above). In some embodiments, after the polynucleotide is elongated it is cast in a gel. For example, in some embodiments, when the polynucleotide is attached to a surface at one end and stretched in flow stream or by electrophoretic current, the surrounding medium becomes cast into a gel. In some embodiments, this occurs by including acrylamide, ammonium persulfate and TEMED in the flow stream. Such compounds, when set, become polyacrylamide. In alternative embodiments, gel that responds to heat is applied. In some embodiments, the end of the polynucleotide is modified with acrydite that polymerizes with the acrylamide. In some such embodiments, an electric field is applied that elongates the polynucleotide towards the positive electrode, given the negative backbone of native polynucleotides.

In some embodiments, the nucleic acid is extracted from cells in a gel plug or a gel layer to preserve the integrity of the DNA and then an AC electric field is applied to stretch the DNA within the gel; when this is done in a gel layer atop a coverglass, the methods of this invention can be applied to the stretched DNA to detect transient olio binding.

In some embodiments, the sample is cross-linked to the matrix of its environment. In one example this is the cellular milieu. For example, when the sequencing is conducted in situ in a cell, the polynucleotide is cross-linked to the cellular matrix using a heterobifunctional cross linker. This is done when sequencing is applied directly inside cells using a technique such as FISSEQ (Lee et al., Science 343:1360-1363, 2014).

Much of the disruption occurs in the process of extracting the biomolecule from cells and tissues and the subsequent handling of the biomolecule before it is analyzed. In the case of DNA, aspects of its handling that lead to its loss of integrity includes pipetting, vortexing, freeze-thawing and excessive heating. In some embodiments, mechanical stress is minimized such as in the manner disclosed in ChemBioChem, 11:340-343 (2010). In addition, high concentrations of divalent cations, EDTA, EGTA or Gallic Acid (and its analogues and derivatives) inhibit degradation by nucleases. In some embodiments, a 2:1 ratio of sample to divalent cation weight is sufficient to inhibit nucleases even in samples such as stool, where there are extreme levels of nucleases.

In order to preserve the integrity of a nucleic acid (e.g., to not induce DNA damage or breakage into smaller fragments), in some embodiments it is desirable to keep a biomacromolecule such as DNA in its natural protective environment such as chromosomes, mitochondria, cells, nuclei, exosomes etc. In embodiments, where the nucleic acid is already outside its protective environment, it is desirable to encase it in a protective environment such as a gel or a microdroplet. In some embodiments the nucleic acid is released from its protective environment in close physical proximity to where it will be sequenced (e.g. the part of a fluidic system or flow cell where the sequencing data will be acquired). Thus, in some embodiments, the biomacromolecule (e.g. nucleic acid, protein) is provided in a protective entity, said protective entity preserving the biomacromolecule close to its native state (e.g. native length), bringing protective entity which comprises the biomacromolecule into close proximity with where it will be sequenced, then releasing the biomacromolecule into the area where it will be sequenced or close to the area where it will be sequenced. In some embodiments, the invention comprise providing an agarose gel comprising genomic DNA, said agarose gel preserving a substantial fraction of the genomic DNA to greater than 200 Kb in length, placing the agarose comprising the genomic DNA in proximity of the environment (e.g. surface, gel, matrix) where the DNA is to be sequenced, releasing the genomic DNA from the agarose into the environment (or close to the environment so that its further transport and handling is minimized) and carrying out the sequencing. The release into the sequencing environment may be by application of an electric field or by digestion of the gel by agarase.

Polymer Denaturation.

Block 206.

The fixed stretched double-stranded nucleic acid are subsequently denatured to single stranded form on the test substrate, thereby obtaining a fixed first strand and a fixed second strand of the nucleic acid. Respective bases of the fixed second strand lie adjacent to corresponding complementary bases of the fixed first strand. In some embodiments, the denaturation is performed by first elongating or stretching the polynucleotide and then adding a denaturation solution to separate the two strands.

In some embodiments, the denaturation is chemical denaturation comprising one or more reagents (e.g., 0.5M NaOH, DMSO, formamide, urea, etc.). In some embodiments, the denaturation is heat denaturation (e.g., by heating the sample to 85° C. or higher). In some embodiments, the denaturation is through enzymatic denaturation such as through the use of helicases, or other enzymes with helicase activity. In some embodiments, the polynucleotides are denatured through interaction with a surface or by a physical process such as stretching beyond a critical length. In some embodiments, the denaturation is full or partial.

In some embodiments, the binding of probes to modifications on the repeating units of the polymer (e.g., the nucleotides in a polynucleotide, or phosphorylation on a polypeptide) are conducted before the optional denaturation step.

In some embodiments, the optional denaturation of a double-stranded polynucleotide is not performed at all. In some such embodiments, the probes must be able to anneal to a duplex structure. For example, in some embodiments, the probes bind to the individual strands of the duplex through strand invasion (e.g., using PNA probes), by inducing excessive breathing of the duplex, by recognizing the sequence in the duplex through a modified zing-finger protein, or by using a Cas9 or similar protein that melts the duplex allowing a guide RNA to bind. In some embodiments, the guide RNA comprises an interrogation probe sequence, and a gRNA comprising each sequence of the repertoire is provided.

In some embodiments, the double-stranded target contains nicks (e.g., natural nicks or those created by DNase1 treatment). In such embodiments, under the conditions of the reaction, one strand transiently frays or peels away from the other (e.g., transiently denaturing), or natural base-pair breathing occurs. This allows the probe to transiently bind, before it is displaced by the native strand.

In some embodiments, the single double-stranded target polynucleotide is denatured, such that each of the strands of the duplex is available for binding by an oligo. In some embodiments, the single polynucleotide is damaged, either by the denaturing process or at another step in the sequencing method, and is repaired (e.g., by the addition of a suitable DNA polymerase).

In some preferred embodiments, the immobilization and linearization of double-stranded genomic DNA (in preparation for transient binding on a surface) comprises molecular combing, UV crosslinking of the DNA to a surface, optional wetting, denaturation of the double-stranded DNA through exposure to chemical denaturants (e.g., alkali solutions, DMSO, etc.), optional exposure to acidic solution after washing, and exposure to optional pre-conditioning buffers.

Annealing of Probes.

Block 208.

After the optional denaturation step, the method continues by exposing the fixed first strand and the fixed second strand to a respective pool of a respective oligonucleotide probe in a set of oligonucleotide probes, where each oligonucleotide probe in the set of oligonucleotide probes is of a predetermined sequence and length. The exposing occurs under conditions that allow for individual probes of the respective pool of the respective oligonucleotide probe to bind and form a respective heteroduplex with each portion (or portions) of the fixed first strand or the fixed second strand that is complementary to the respective oligonucleotide probe thereby giving rise to a respective instance of optical activity.

Figure 5A:
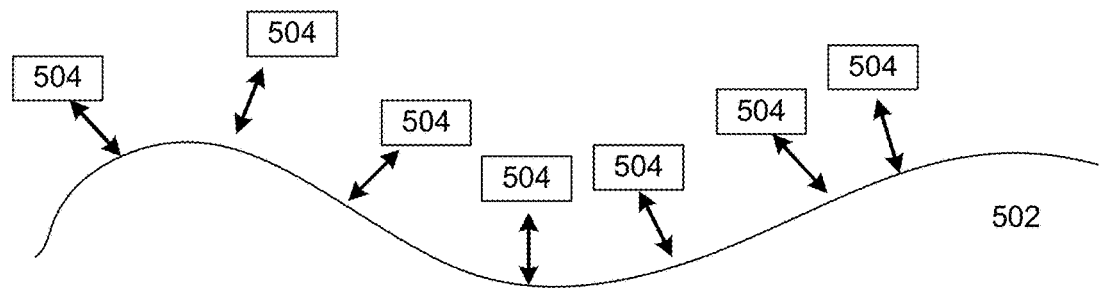
FIGS. 5A, 5B, and 5C collectively illustrate an example, of transient binding of probes to a polynucleotide in accordance with various embodiments of the present disclosure.
Figure 5B:
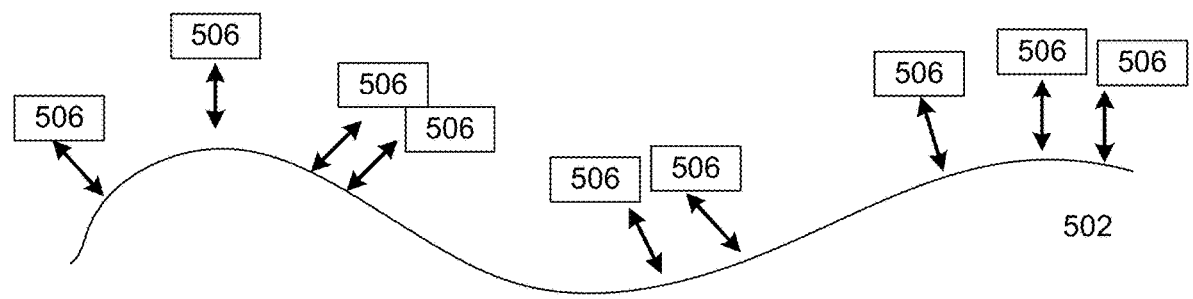
Figure 5C:
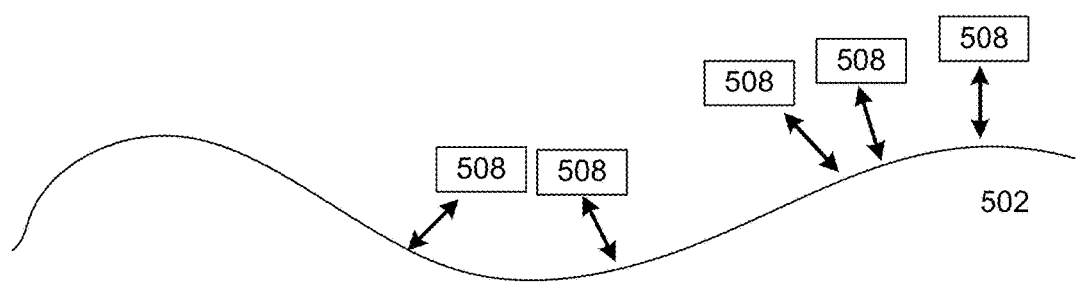

FIGS. 5A, 5B, and 5C illustrate an example of transient binding of different probes to one polymer 502. Each probe (e.g., 504, 506, and 508) comprises a specific interrogation sequence (e.g., a nucleotide or peptide sequence). After the application of probes 504 to polynucleotide 502, probes 504 are washed off of polymer 502 with one or more wash steps. Similar wash steps are used to subsequently remove probes 506 and 508.

Probe Design and Targets.

In some embodiments, probes are provided to the target polynucleotides in solution. When the solution is of sufficient volume to submerge the polynucleotides on the surface or matrix, the probes are able to make contact with the polynucleotides through diffusion and molecular collisions. In some embodiments, the solution is agitated to bring probes in contact with the one or more polynucleotides. In some embodiments, the probe containing solution is exchanged to bring fresh probes to the surface. In some embodiments, an electric field is used to attract the probes to the surface, for example, a positively biased surface attracts negatively charged oligos.

In some embodiments, the target comprises a polynucleotide sequence and the binding part of the probe comprises, for example, a 3-mer, a 4-mer, a 5-mer, or a 6-mer oligonucleotide sequence interrogation portion, optionally one or more degenerate or universal positions, and optionally a nucleotide spacer (e.g., one on more T nucleotides) or a basic or non-nucleotide portion. As illustrated in FIGS. 6A and 6B, similar binding occurs along a polynucleotide 602, regardless of the size of the oligo probes (e.g., 604 and 610) that are used. The primary difference inherent to different k-mer length oligos is that the k-mer length sets the length of the binding sites that will be bound by the respective probes (e.g., 3-mer probes 604 will primarily bind to 3-nucleotide long sites such as 606, and 5-mer probes 610 will primarily bind to 5-nucleotide long sites such as 610).

In FIG. 6A, the 3-mer oligo probes are unusually short. Normally such short sequences are not used as probes because they cannot bind stably unless very low temperatures and long incubation times are used. However, such probes do form transient bonds to a target polynucleotide, as required by the detection methods described herein. Further, the shorter the oligonucleotide probe sequence, the fewer oligonucleotides are present in the repertoire. For example, only 64 oligonucleotide sequences are required for a complete repertoire of 3-mer oligos, while 256 oligonucleotide sequences are required for a complete 4-mer repertoire. Further, ultra-short probes are modified in some embodiments to increase melting temperature and, in some embodiments, include degenerate (e.g., N) nucleotides. For example, four N nucleotides would increase the stability of a 3-mer oligo to the stability of a 7-mer.

In FIG. 6B, the schematic illustrates the binding of a 5-mer to its perfect match position (612-3), a 1 base mismatch position (612-2) and a 2 base mismatch position (612-1).

The binding of any one probe is not sufficient to sequence the polynucleotide. In some embodiments, a complete repertoire of probes is needed to reconstruct the sequence of the polynucleotide. Information on the location of oligo binding sites, the temporally separated binding of probes to overlapping binding sites, the partial binding of mismatches between the oligos and the target nucleotide, the frequency of bindings, and the duration of bindings all contribute to deducing a sequence. In the case of elongated or stretched polynucleotides, the location of probe binding along the length of the polynucleotide contributes to building a robust sequence. In the case of double-stranded polynucleotides, a greater confidence sequence emerges from the sequencing of both strands of the duplex (e.g., both complementary strands) simultaneously.

In some embodiments a common reference probe sequence is added together with each of the oligonucleotide probes in the repertoire. For example, in FIGS. 7A, 7B, and 7C the common reference probe 704 binds to the same binding sites 708 on the target polynucleotide 702 regardless of the additional probes included in the probe set (e.g., 706, 712, and 716). The presence of reference probes 704 do not inhibit the binding of the other probes to their respective binding sites (e.g., 710, 714, 718, 720, and 722).

As depicted in FIG. 7C, binding sites 718, 720, and 722 illustrate how individual probes (716-1, 716-2, and 716-3) will bind all of the possible sites, even when those sites are overlapping. In FIGS. 7A, 7B, and 7C, the probe sequences are depicted by 3-mers. However, similar methods could equally well be performed with probes that are 4-mers, 5-mers, 6-mers, etc.

In some embodiments, the set of oligonucleotide probes is a complete repertoire of oligos (e.g., every oligo of a given length). For example, the entire set of the 1024 individual 5-mers is encoded and included in a particular repertoire in accordance with one embodiment of the present disclosure. In some embodiments, a repertoire of multiple lengths is provided. In some embodiments, the set of oligonucleotide probes is a tiling series of oligo probes. In some embodiments, the set of oligonucleotide probes is a panel of oligo probes. In the case of certain applications in synthetic biology (e.g., DNA data storage) the sequencing comprises finding the order of specific blocks of sequence, where the blocks are designed to encode the desired data.

Figure 8A:
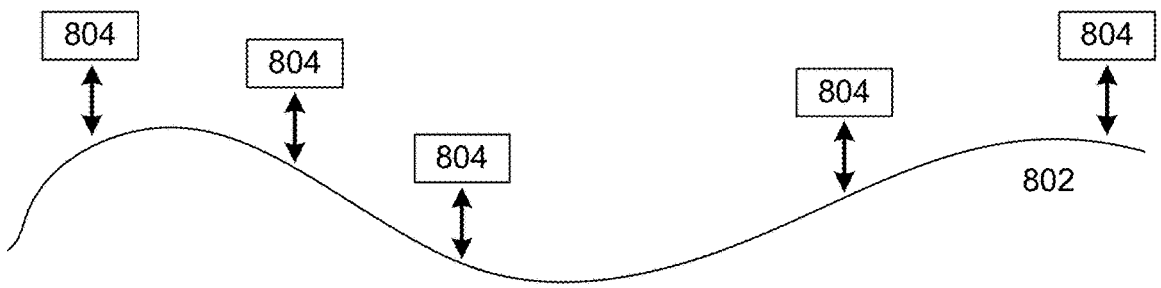
FIGS. 8A, 8B, and 8C collectively illustrate an example of applying distinct probe sets to a single reference molecule in accordance with various embodiments of the present disclosure.
Figure 8B:
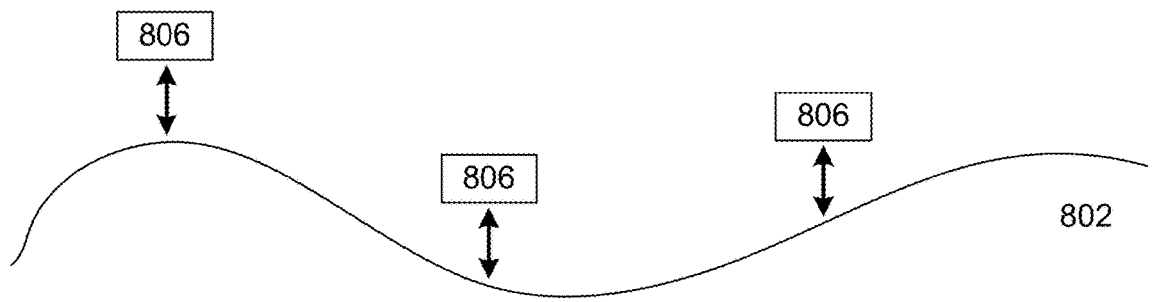
Figure 8C:
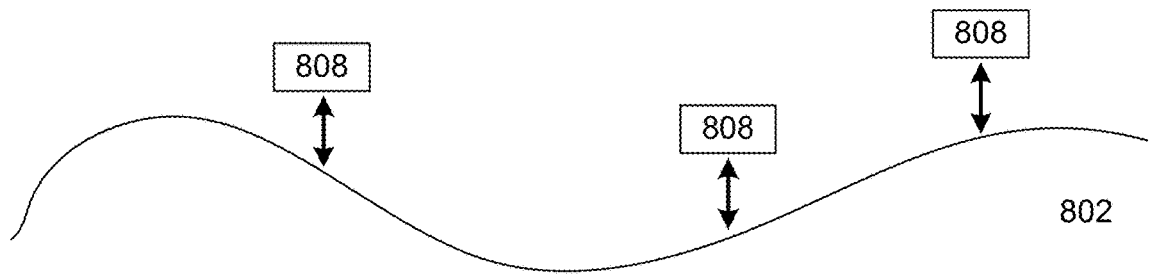

As illustrated by FIGS. 8A, 8B, and 8C, multiple probe sets (e.g., 804, 806, and 808), are applied to any target polymer 802 in some embodiments. Each probe type will bind preferentially to its complementary binding sites. In many embodiments, washing with a buffer in between each cycle aids removal of probes in the previous set.

Figure 9A:
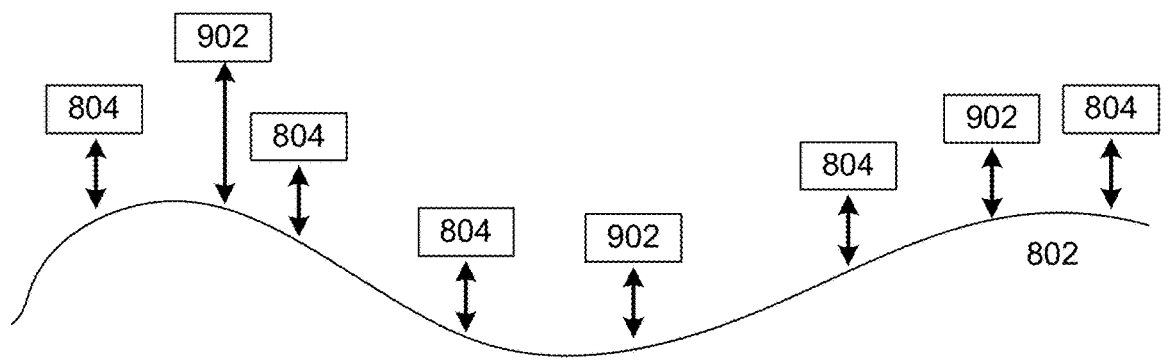
FIGS. 9A, 9B, and 9C collectively illustrate an example of transient binding in cases where multiple types of probes are used, in accordance with various embodiments of the present disclosure.
Figure 9B:
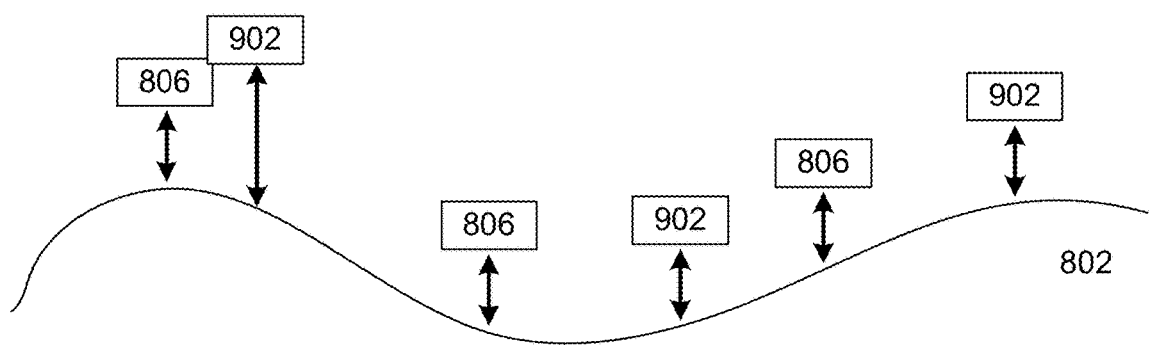
Figure 9C:
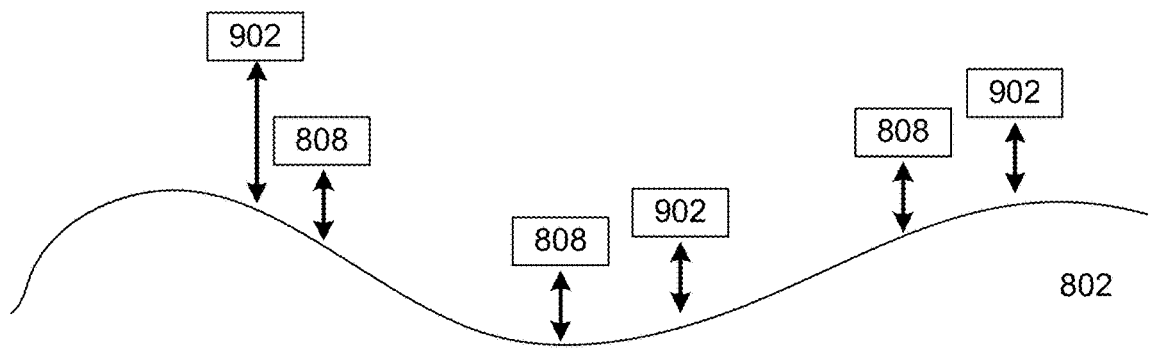

In some embodiments, the probes for nucleic acid sequencing are oligonucleotides and the probes for epi-modifications are modification-binding proteins or peptides (e.g., methyl binding proteins such as MBD1) or anti-modification antibody (e.g., anti-methyl C antibody). In some embodiments, oligo probes target specific sites in the genome (e.g., sites with known mutations). As illustrated in FIGS. 9A, 9B, and 9C, both oligonucleotides (e.g., 804, 806, and 808) and alternate probes (e.g., 902) are applied concurrently (and through multiple cycles) to a polynucleotide or polymer 802 in some embodiments. A method of determining target sites of interest is provided by Liu et al., BMC Genomics 9: 509 (2008), which is hereby incorporated by reference.

In some embodiments, each of the probes of the repertoire or a subset of the probes of the repertoire are applied one after the other (e.g., the binding of one or a subset is first detected and then it is removed, before the next added, detected and removed then the next, etc.). In some embodiments, all or a subset of binding probes in the repertoire are added simultaneously and each binding probe is tethered to a label that codes completely or partially for its identity and the code for each of the binding probes is decoded by detection.

As illustrated by FIGS. 11A and 11B, tiling series of probes is used to gain information on the binding sites of multiple probes in some embodiments. In FIG. 11A a first tiling set 1104 is applied to a target polynucleotide 1102. Each probe in a subset of probes in the first tiling set 1108 contains one base 1108, thereby resulting in 5X coverage of that one nucleotide in the target polynucleotide 1102. The coverage will be proportional to the k-mer length of the probes in the tiling series (e.g., a set of 3-mer oligos will result in 3X coverage of every base in the target polynucleotide).

In some embodiments, when the set of oligonucleotide probes tiles along the target nucleotide, there is a potential for a problem to arise when there is a break in the tiling path. For example, with an oligonucleotide set of 5-mers there is no oligo that is capable of binding to one or more stretches of sequence in the target molecule longer than 5 bases. In this case, one or more approaches is taken in some embodiments. First, if the target polynucleotide comprises a double-stranded nucleic acid, the one or more base assignments defer to the sequence(s) obtained from the complementary strand of the duplex. Second, when multiple copies of the target molecule are available, the one or more base assignments rely on other copies of the same sequences on the other copies of the target molecule. Third, in some embodiments, if a reference sequence is available, the one or more base assignments defer to a reference sequence, and the bases are annotated to indicate that they are artificially implanted from the reference sequence.

In some embodiments, certain probes are omitted from the repertoire for various reasons. For example, some probe sequences exhibit problematic interactions with themselves—such as self-complementarity or palindromic sequences, with other probes in the repertoire or with the polynucleotide (e.g., known stochastic promiscuous binding). In some embodiments, a minimal number of informative probes is determined for each type of polynucleotide. Within a complete repertoire of oligos, half of the oligos are completely complementary to other half of the oligos. In some embodiments, it is ensured that these complementary pairs (and others that are problematic due to substantial complementarity) are not added to the polynucleotide at the same time, but are rather assigned to different subsets of probes. In some embodiments, where both sense and antisense single-stranded DNA are present, sequencing is performed with just one member of each oligo complementary pair. Sequencing information obtained from both sense and antisense strands is combined to generate the overall sequence. However, this method is not preferred as it forgoes the advantage conferred by sequencing both strands of a double-stranded polynucleotide simultaneously.

In some embodiments, the oligos comprise a library made using custom microarray synthesis. In some embodiments, the microarray library comprises oligos that systematically bind to specific target parts of the genome. In some embodiments, the microarray library comprises oligos that systematically bind to locations a certain distance apart across the polynucleotide. For example, a library comprising one million oligos could comprise oligos that are designed to bind approximately every 3000 bases. Similarly, a library comprising ten million oligos could be designed to bind approximately every 300 bases, and a library comprising 30 million oligos could be designed to bind every 100 bases. In some embodiments, the sequence of the oligos is designed computationally based on a reference genome sequence.

In some embodiments, the parts of the genome that are targeted are specific genetic loci. In other embodiments, the parts of the genome that are targeted are a panel of loci (e.g., genes linked to cancer) or genes within a chromosomal interval identified by a genome-wide association study. In some embodiments, the targeted loci are also the dark matter of the genome, heterochromatic regions of the genome that are typically repetitive, as well the complex genetic loci that are in the vicinity of the repetitive regions. Such regions included the telomeres, the centromeres, the short arms of the acrocentric chromosomes as well as other low complexity regions of the genome. Traditional sequencing methods cannot address the repetitive parts of the genome, but when the nanometric precision is high the methods comprehensively address these regions.

In some embodiments, each respective oligonucleotide probe in the plurality of oligonucleotide probes comprises a unique N-mer sequence, where N is an integer in the set {1, 2, 3, 4, 5, 6, 7, 8, and 9} and where all unique N-mer sequences of length N are represented by the plurality of oligonucleotide probes.

The longer the oligo length used to make probes the more potential there is for palindromic or foldback sequences having an effect on the oligo to function as an efficient probe. In some embodiments, binding efficiency is substantially improved by reducing the length of such oligos by removing one or more degenerate bases. For this reason, the use of shorter interrogation sequences (e.g., 4-mers) are advantageous. However, shorter probe sequences also exhibit less stable binding (e.g., lower binding temperatures). In some embodiments, the binding stability of the oligo is enhanced using specific stabilizing base modifications or oligo conjugates (e.g., a stilbene cap). In some embodiments, 3-mer or 4-mers that are completely modified (e.g., locked nucleic acids (LNA)) are used.

In some embodiments, the unique N-mer sequence comprises one or more nucleotide positions occupied by one or more degenerate nucleotides. In some embodiments the degenerate position comprises one of the four nucleotides and versions with each of the four nucleotides are provided in the reaction mix. In some embodiments, each degenerate nucleotide position in the one or more nucleotide positions is occupied by a universal base. In some embodiments, the universal base is 2'-Deoxyinosine. In some embodiments, the unique N-mer sequence is flanked at the 5' end by a single degenerate nucleotide position and flanked at the 3' end by a single degenerate nucleotide position. In some embodiments, the 5' single degenerate nucleotide and the 3' single degenerate nucleotide are each 2'-Deoxyinosine.

In some embodiments, each oligonucleotide probe in the set of oligonucleotide probes is of the same length M. In some embodiments, M is a positive integer of 2 or greater. The determining (f) the sequence of at least a portion of the nucleic acid from the plurality of sets of positions on the test substrate further uses the overlapping sequences of the oligonucleotide probes represented by the plurality of sets of positions. In some embodiments, each oligonucleotide probe in the set of oligonucleotide probes shares M−1 sequence homology with another oligonucleotide probe in the set of oligonucleotide probes.

Probe Labels.

In some embodiments, each oligonucleotide probe in the set of oligonucleotide probes is bound with a label. FIGS. 14A-E illustrate different methods of labeling probes. In some embodiments, the label is a dye, a fluorescent nanoparticle, or a light-scattering particle. In some embodiments a probe 1402 is bound directly to a label 1406. In some embodiments, a probe 1402 is indirectly labeled via a flap sequence 1410 that includes a sequence 1408-B that is complementary to a sequence on the oligo 1408-A.

Many types of organic dyes with favorable characteristics are available for labeling, some with high photo stability and/or high quantum efficiency and/or minimal dark-states and/or high solubility, and/or low non-specific binding. Atto 542 is a favorable dye that possesses a number of favorable qualities. Cy3B is a very bright dye and Cy3 is also effective. Some dyes allow the avoidance of wavelengths where auto fluorescence from cells or cellular material is prevalent, such as the red dyes Atto 655 and Atto 647N. Many types of nanoparticles are available for labeling. Beyond fluorescently labeled latex particles, the present disclosure makes use of gold or silver particles, semiconductor nanocrystals, and nanodiamonds as nanoparticle labels. Nanodiamonds, in some embodiments, are particularly favorable as labels. Nanodiamonds emit light with high quantum efficiency (QE), have high photo stability, long fluorescent lifetimes (e.g., on the order of 20 ns, which can be used to reduce the background observed from light scattering and/or autofluorescence), and are small (e.g., around 40 nm in diameter). DNA nanostructures and nanoballs can be exceptionally bright labels, either by incorporating organic dyes into their structure or mopping up labels such as intercalating dyes.

In some embodiments, each indirect label specifies the identity of the base being coded in the sequence interrogation part of the probe. In some embodiments, the label comprises one or more molecules of a nucleic acid intercalating dye. In some embodiments, the label comprises one or more types of dye molecules, fluorescent nanoparticles, or light-scattering particles. In some embodiments, it is preferred that the label does not photobleach quickly, to permit longer imaging times.

Figure 12A:
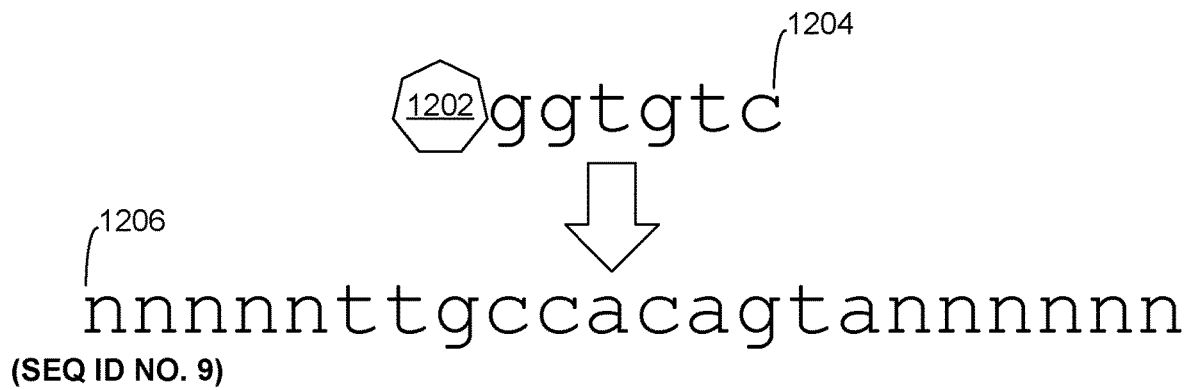
FIGS. 12A, 12B, and 12C collectively illustrate an example of transient binding of a directly labeled probe in accordance with various embodiments of the present disclosure.
Figure 12B:
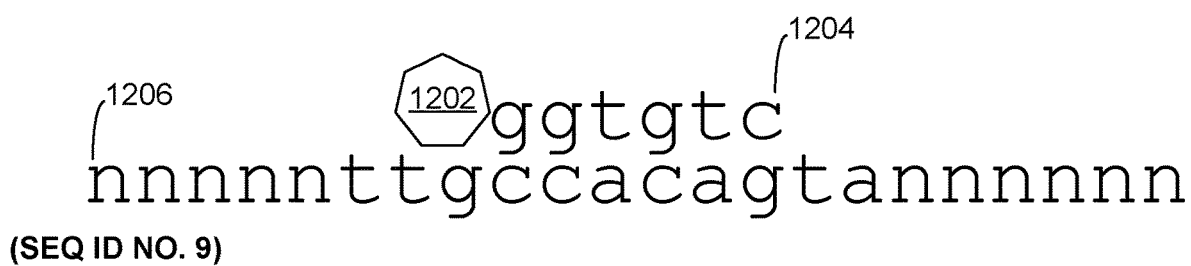
Figure 12C:
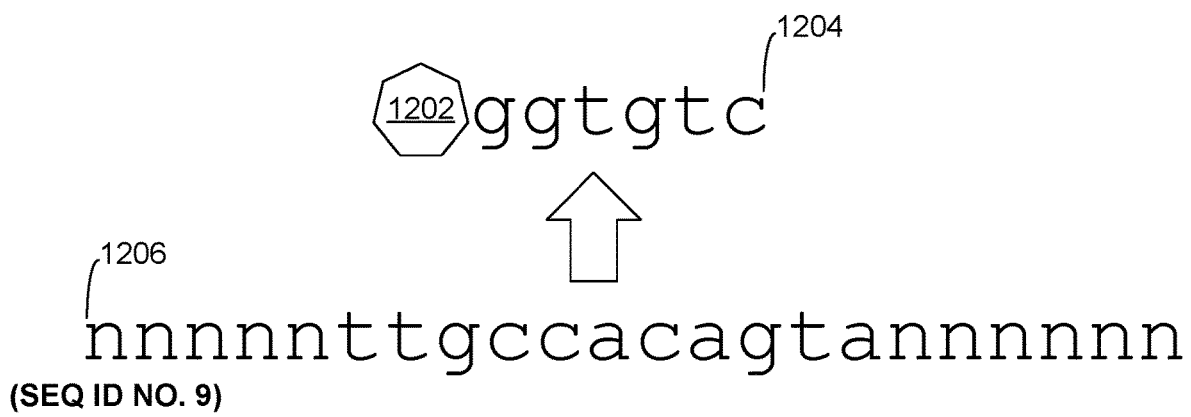
Figure 13A:
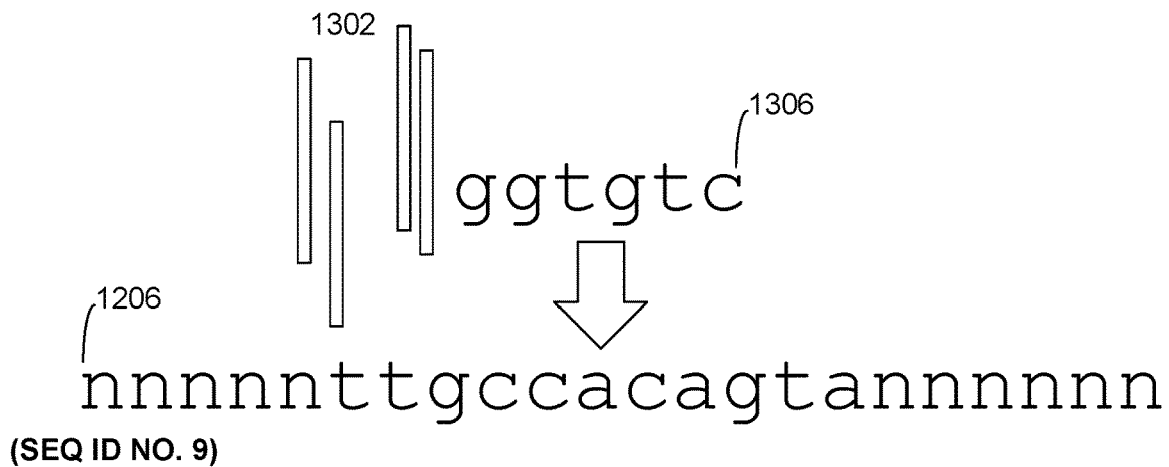
FIGS. 13A, 13B, and 13C collectively illustrate an example of transient probe binding in the presence of an intercalating dye in accordance with various embodiments of the present disclosure.
Figure 13B:
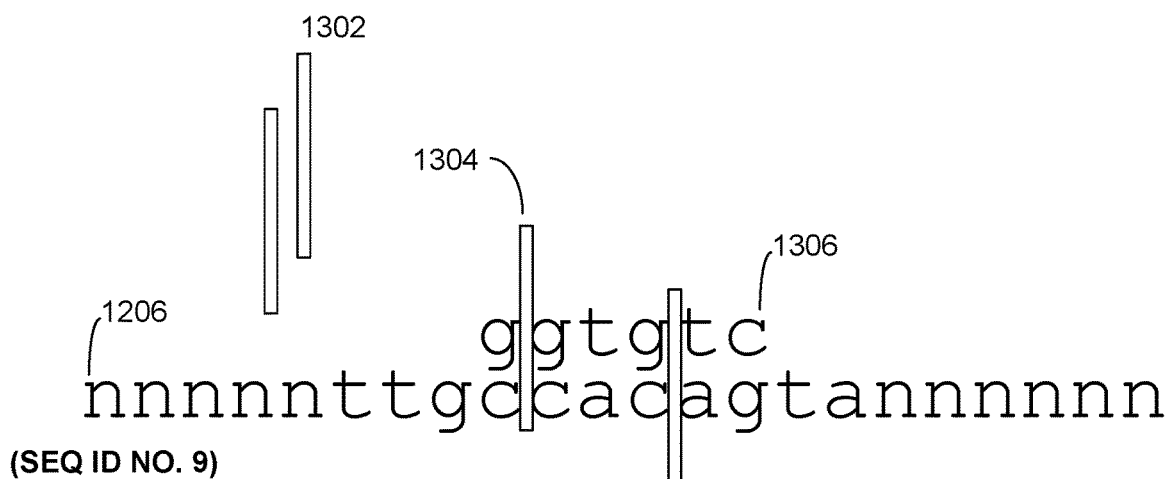
Figure 13C:
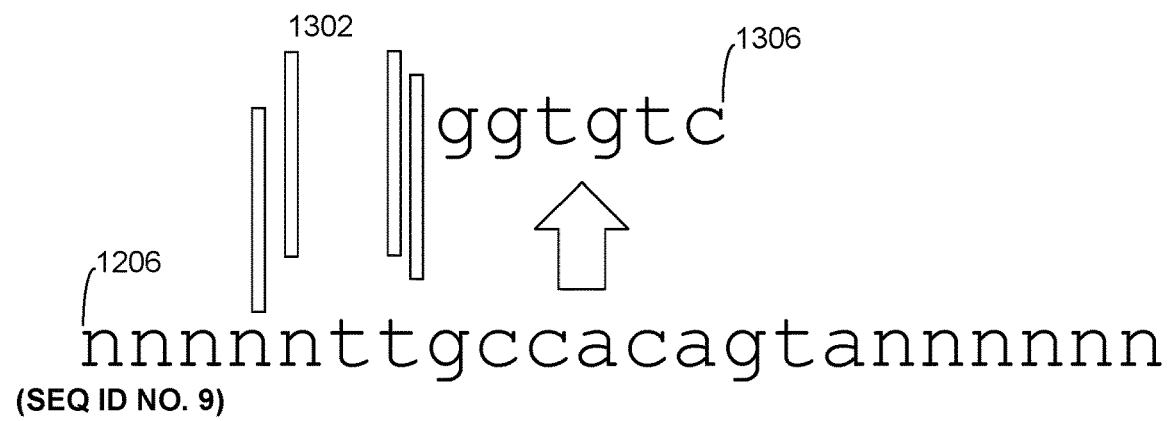

FIGS. 12A, 12B, and 12C, illustrate the transient on-off binding of an oligonucleotide 1204 with an attached fluorescent label 1202 to a target polynucleotide 1206. The label 1202 will fluoresce regardless of whether the probe 1204 binds to a binding site on the target polynucleotide 1206. Similarly, FIGS. 13A, 13B, and 13C illustrate the transient on-off binding of an unlabeled oligonucleotide probe 1306. The binding event is detected by intercalation of a dye (e.g., YOYO-1) from solution 1302 into the transiently forming duplex 1304. An intercalating dye exhibits a significant increase in fluorescence when bound into a double-stranded nucleic acid as compared to floating free in solution.

In some embodiments, the probe that binds the target is not directly labeled. In some such embodiments, the probe contains a flap. In some embodiments, building the oligonucleotides (e.g., encoding them) comprises coupling specific sequence units to one end (e.g., a flap sequence) of each k-mer in the set of oligonucleotides. Each unit of the encoding sequence of the flap acts as a docking site for a distinct fluorescently labelled probe. In order to encode a 5 base probe sequence, the flap on the probe contains 5 distinct binding locations, for example, each location is a different DNA base sequence linked tandemly to the next location. For example, the first position on the flap is adjacent to the probe sequence (the part that will bind to the polynucleotide target), the second is adjacent to the first, and so on. In advance of using the probe-flap in sequencing, each variety of probe-flap is coupled to a set of fluorescently labelled oligos to generate a unique identifier tag for the probe sequence. In some embodiments this is done by using four distinctly labelled oligo sequences that are complementary to each position on the flap (e.g., a total of sixteen distinct labels).

In some embodiments, probes where A, C, T and G are defined are coded in a manner that the label reports on just one defined nucleotide at a specific position in the oligonucleotide (and the rest of the positions are degenerate). This requires just a four color coding, one color per nucleotide.

In some embodiments, only one fluorophore color is used throughout the process. In such an embodiment, each cycle is split into 4-sub-cycles, in each of which one of the 4 bases at the specified position (e.g., position 1) is added individually before the next one is added. In each cycle, the probes carry the same label. In this implementation, the whole repertoire is exhausted in 20 cycles, a significant saving in time.

In some embodiments, the first base in the sequence is encoded by the first unit in the flap, the second base by the second unit, etc. The order of the units in the flap corresponds to the order of the base sequence in the oligo. Distinct fluorescent labels are then docked onto each of the units (through complementary base pairing). The first position, in one example, emits at wavelength 500 nm-530 nm, the second at wavelength 550 nm-580 nm, the third at 600 nm-630 nm, the fourth at 650 nm-680 nm and the fifth at 700 nm-730 nm. The identity of the base at each location is then, for example, encoded by the fluorescence lifetime of the label. In one such example, the label corresponding to A has a longer lifetime the C, which has a longer lifetime than G, which has a longer lifetime than T. In the example, above, base A at position 1 would emit at 500 nm-530 nm with the longest lifetime and base G at position 3 would emit at 600 nm-630 nm with the third longest lifetime, etc.

Figure 14A:
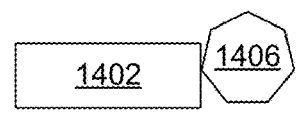
FIGS. 14A, 14B, 14C, 14D, and 14E collectively illustrate examples of different probe labeling techniques in accordance with various embodiments of the present disclosure.
Figure 14B:
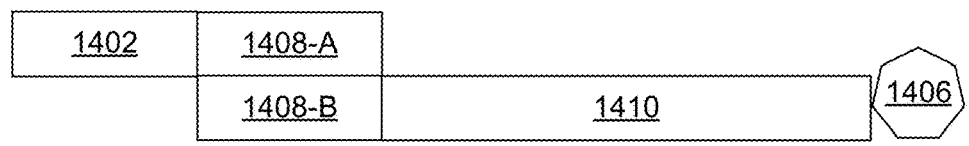
Figure 14C:
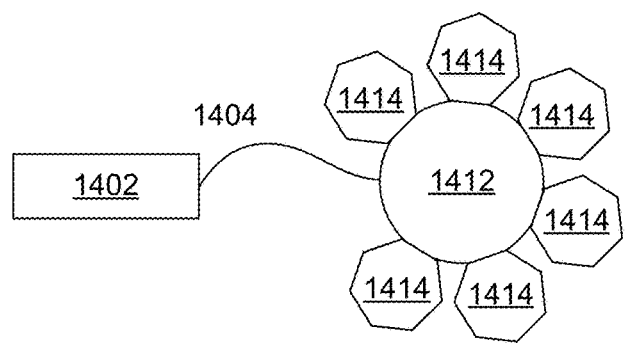
Figure 14D:
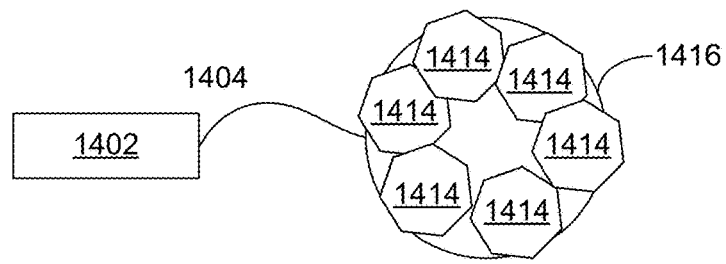
Figure 14E:
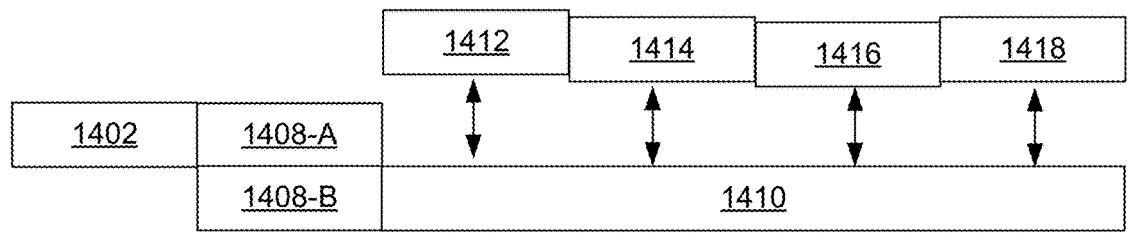

As illustrated in FIG. 14E, a probe 1402 will include a sequence 1408-A that corresponds to sequence 1408-B. Sequence 1408-B is attached to the flap region 1410. As an example of the possible sequences that could result in the FIG. 14E overall construct, each of the four positions in 1410 are defined by the sequences AAAA (e.g., the position complementary to 1412), CCCC (e.g., the position complementary to 1414), GGGG (e.g., the position complementary to 1416), and TTTT (e.g., the position complementary to 1418) respectively. Thus, the overall flap sequence would be (SEQ ID NO. 1) 5'-AAAACCCCGGGGTTTT-3'. Then each position is coded for by a specific emission wavelength, and the four different bases that could be at that position are coded for by four different fluorescence lifetime-labelled oligo, where the lifetime/brightness ratio corresponds to a particular position and base code in probe 1402 itself.

An example of suitable code is the following:
Position 1—A base code-TTTT-Emission peak 510, lifetime/brightness #1
Position 1—C base code-TTTT-Emission peak 510, lifetime/brightness #2
Position 1—G base code-TTTT-Emission peak 510, lifetime/brightness #3
Position 1—T base code-TTTT-Emission peak 510, lifetime/brightness #4
Position 2—A base code-GGGG-Emission peak 560, lifetime/brightness #1
Position 2—C base code-GGGG-Emission peak 560, lifetime/brightness #2
Position 2—G base code-GGGG-Emission peak 560, lifetime/brightness #3
Position 2—T base code-GGGG-Emission peak 560, lifetime/brightness #4
Position 3—A base code-CCCC-Emission peak 610, lifetime/brightness #1
Position 3—C base code-CCCC-Emission peak 610, lifetime/brightness #2
Position 3—G base code-CCCC-Emission peak 610, lifetime/brightness #3
Position 3—T base code-CCCC-Emission peak 610, lifetime/brightness #4
Position 4—A base code-AAAA-Emission peak 660, lifetime/brightness #1
Position 4—C base code-GGGG-Emission peak 660, lifetime/brightness #2
Position 4—G base code-GGGG-Emission peak 660, lifetime/brightness #3
Position 4—T base code-GGGG-Emission peak 660, lifetime/brightness #4

Alternatively, the four positions are coded by fluorescence lifetime and the bases are coded by fluorescence emission wavelength. In some embodiments, other measureable physical attributes are alternatively used for coding or if compatible can be combined with wavelength and lifetime. For example, the polarization or the brightness of the emission could also be measured to increase the repertoire of codes available for inclusion into a flap.

In some embodiments, toe-hold probes (e.g., as described by Levesque et al., Nature Methods 10:865-867, 2013) are used. These probes are partly double-stranded, and are competitively destabilized when bound to a mismatching target (e.g., a detailed in Chen et al., Nature Chemistry 5, 782-789, 2013). In some embodiments, the toe-hold probes are used alone. In some embodiments, the toe-hold probes are used to ensure correct hybridization. In some embodiments, the toe-hold probes are used to facilitate the off reaction of other probes bound to the target polynucleotide.

An example of a label that is excited by a common excitation line is a quantum dot. In some such embodiments in accordance with this example, Qdot 525, Qdot 565, Qdot 605, and Qdot 655 are chosen to be the four respective nucleotides. Alternatively, four distinct laser lines are used to excite four distinct organic fluorophores and their emission detected split by an image splitter. In some other embodiments, the emission wavelength is the same for two or more of the organic dyes and but the fluorescent lifetime is different. The skilled artisan will be able to envisage a number of different encoding and detection schemes, without undue effort and experimentation.

In some embodiments, the different oligos in the repertoire are not added individually but rather are encoded and pooled together. The simplest step up from one color and one oligo at a time, is two color and two oligos at a time. It is reasonable to expect to pool up to around 5 oligos at a time using direct detection of 5 distinguishable single dye flavors, one dye per each of the 5 oligos.

In more complex cases, the number of flavors or codes increases. For example, to individually code for each base in a complete repertoire of 3-mers, 64 distinct codes would be required. Also, by example, to individually code for each base in a complete repertoire of 5-mers 1024 distinct codes would be required. Such high number of codes is achieved by having a code per oligo composed of multiple dye flavors. In some embodiments, a smaller set of codes is used to encode subset of the repertoire (sub-repertoire) e.g., in some instance 64 codes is used to encode 16 subsets of the complete 1024 sequence repertoire of 5-mers.

In some embodiments, a large repertoire of oligo codes is obtained in a number of ways. For example, in some embodiments, beads are loaded with a code-specific dyes or DNA nanostructure-based codes comprise an optimal spacing of different fluorescent wavelength emitting dyes (e.g., Lin et al., Nature Chemistry 4: 832-839, 2012). For example, FIGS. 14C and 14D illustrate uses of a bead 1412 in carrying fluorescent labels 1414. In FIG. 14C, the labels 1414 are coated on bead 1412. In FIG. 14D, the labels 1414 are encapsulated in bead 1412. In some embodiments, each label 1414 is a different type of fluorescent molecule. In some embodiments, all labels 1414 are the same type of fluorescent molecule (e.g., Cy3).

In some embodiments, a coding scheme is used in which a modular code is used to describe the position of the base in the oligo and its identity. In some embodiments, this is implemented by adding a coding arm to the probe comprising a combination of labels that identify the probe. For example, where a library of every possible 5-mer oligonucleotide probe is to be encoded, the arm has five sites each site corresponding to each of the five nucleobases in a 5-mer, and each of the five sites is bound to five distinguishable species. In one such example, fluorophores with a specific peak emission wavelength correspond to each of the positions (e.g., 500 nm for position one, 550 nm for position two, 600 nm for position three, 650 nm for position four and 700 nm for position five), and four fluorophores with the same wavelength but different fluorescence lifetime code for each of the four bases at each position.

In some embodiments, the different labels on oligos or other binding reagents are coded by wavelength of emission. In some embodiments, the different labels are coded by fluorescence lifetime. In some embodiments, the different labels are coded by fluorescence polarization. In some embodiments, the different labels are coded by a combination of wavelength, fluorescence lifetime.

In some embodiments, the different labels are coded by repetitive on-off hybridization kinetics. Different binding probes with different association-dissociation constants are used. In some embodiments, the probes are coded by fluorescence intensity. In some embodiments, the probes are fluorescent intensity coded by having different number of non-self-quenching fluorophores attached. The individual fluorophores typically need to be well separated in order not to quench. In some embodiments this is accomplished using a rigid linker or a DNA nanostructure to hold the labels in place at a suitable distance from each other.

One alternative embodiment for coding by fluorescence intensity is to use dye variants that have similar emission spectra but differ in their quantum yield or other measureable optical character. For example, Cy3B, with an excitation/emission 558/572, is substantially brighter (e.g., a quantum yield of 0.67) than Cy3, with an excitation/emission 550/570 and a quantum yield of 0.15) but have similar absorption/emission spectra. In some such embodiments, a 532 nm laser is used to excite both dyes. Other suitable dyes include Cy3.5 (with an excitation/emission 591/604 nm) that has an up shifted excitation and emission spectra but will nonetheless be excited by the 532 nm laser. However, an excitation at that wavelength is sub-optimal for Cy3.5 and the emission of the dye will appear less bright in the bandpass filter for Cy3. Atto 532, with an excitation/emission 532/553, has a quantum yield of 0.9 and would be expected to be bright as the 532 nm laser hits it at its sweet spot.

Another approach to obtaining multiple codes using a single excitation wavelength is to measure the emission lifetimes of the dyes. In one example in accordance with such an embodiment, a set comprising Alexa Fluor 546, Cy3B, Alexa Fluor 555 and Alexa Fluor 555 is used. In some instances, other dyes sets are more useful. In some embodiments, the repertoire of codes is expanded by using FRET pairs and also by measuring the polarization of emitted light. Another method for increasing the number of labels is by coding with multiple colors.

Figure 15:
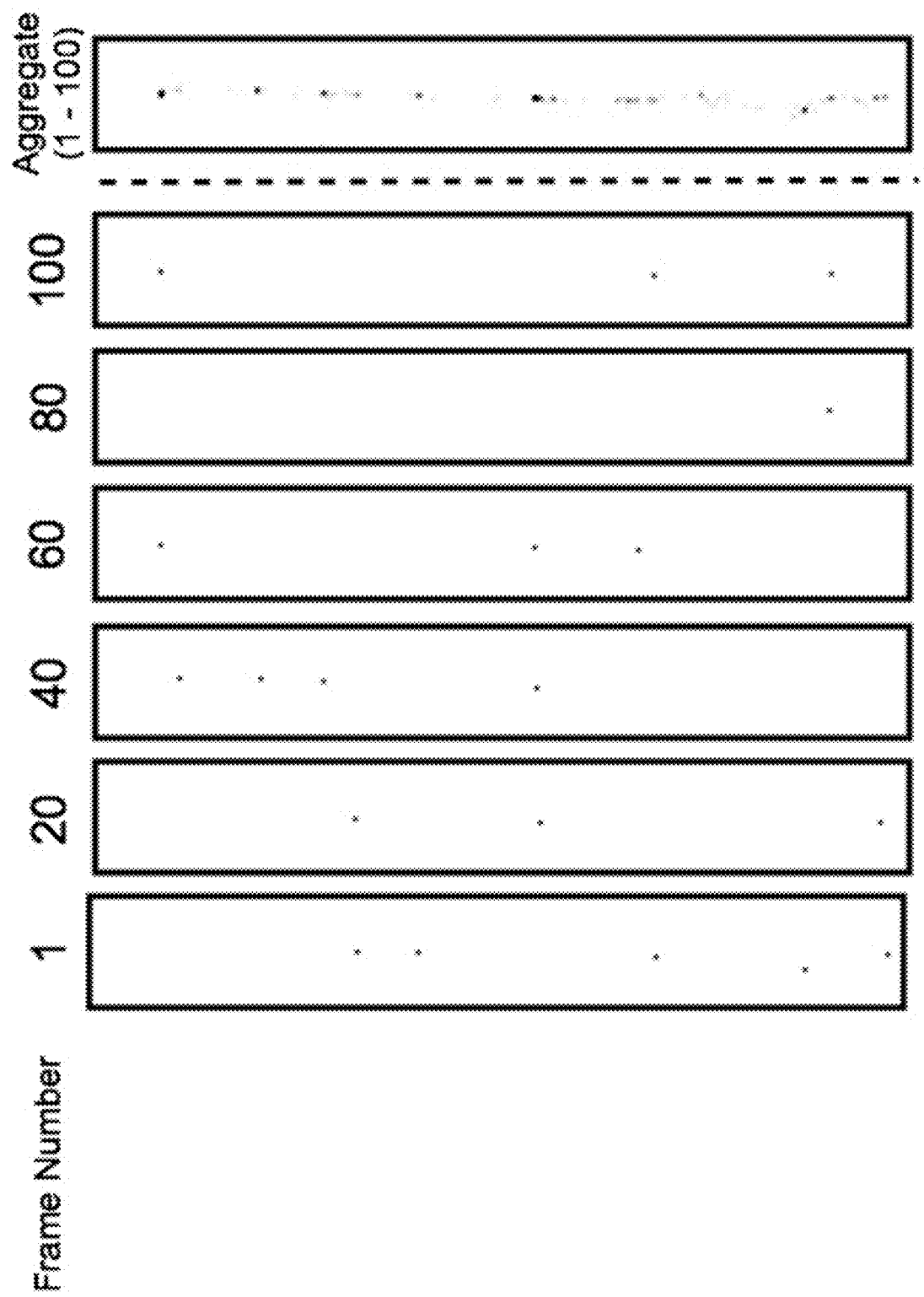
FIG. 15 illustrates an example of transient binding of probes on denatured, combed, double-stranded DNA in accordance with various embodiments of the present disclosure.

FIG. 15 illustrates an example of fluorescence from transient binding of oligonucleotide probes to a polynucleotide. The selected frames from the time series (e.g., Frame Numbers 1, 20, 40, 60, 80, 100) show the presence (e.g., dark spots) and absence of signal (e.g., white regions) at specific sites, indicative of on-off binding. Each respective frame shows the fluorescence of multiple bound probes along the polynucleotide. The Aggregate image shows the aggregation of the fluorescence of all the previous frames, indicating all sites where the oligonucleotide probes have bound.

Transient Binding of Probes to Target Polynucleotides.

Binding of probes is a dynamic process, and a probe that is bound constantly has some probability of coming unbound (e.g., as determined by various factors including temperature and salt concentration). Hence, there is always an opportunity for the displacement of one probe with another. For example, in one embodiment, probe complements are used that cause a continuous competition between annealing to the stretched target DNA on the surface and with the complement in solution. In another embodiment, the probe has three parts, the first part is complementary to the target, the second part is partially complementary to the target and partially complementary to an oligo in solution, and the third part is complementary to the oligo in solution. In some embodiments, collecting information on the precise spatial location of units of chemical structure aids in determining the structure and/or sequence of the macromolecule. In some embodiments, the locations of probe binding sites are determined with nanometric or even sub-nanometric precision (e.g., by using a single molecule localization algorithm). In some embodiments, a plurality of observed binding sites that are physically closer is resolvable by diffraction limited optical imaging methods are resolved because the binding events are temporally separated. The sequence of the nucleic acid is determined based on the identity of probes that bind to each location.

The exposing occurs under conditions that allow for individual probes of the respective pool of the respective oligonucleotide probe to transiently and reversibly bind and form the respective heteroduplex with each portion of the fixed first strand or the fixed second strand that is complementary to the individual probes thereby giving rise to an instance of optical activity. In some embodiments the dwell time (e.g., the duration and/or the persistence of binding by a particular probe), is used in determining whether a binding event is a perfect match, mismatch, or spurious.

In some embodiments, the exposing occurs under conditions that allow for individual probes of the respective pool of the respective oligonucleotide probe to repeatedly transiently and reversibly bind and form the respective heteroduplex with each portion of the fixed first strand or the fixed second strand that is complementary to the individual probes thereby repeatedly giving rise to the respective instance of optical activity.

In some embodiments, the sequencing comprises subjecting the elongated polynucleotide to transient interactions from each of a complete sequence repertoire of probes provided one after the next (the solution carrying one probe sequence is removed, and the solution carrying the next probe solution is added). In some embodiments, the binding of each probe is carried out under conditions that would allow the probe to bind transiently. So for example, the binding would be conducted at 25° C. for one probe and 30°

C. for the next. Also probes can be bound in sets, for example, all probes that would bind transiently, in much the same way, can be gathered into sets and used together. In some such embodiments, each probe sequence of the set is differentially labelled or differentially encoded.

In some embodiments, the transient binding is conducted in a buffer with a small amount of divalent cation but with no monovalent cation. In some embodiments, the buffer comprises 5 mM Tris-HCl, 10 mM magnesium chloride, mm EDTA, 0.05% Tween-20, and pH 8. In some embodiments, the buffer includes less than 1 nM, less than 5 nM, less than 10 nM, or less than 15 nM of magnesium chloride.

In some embodiments, multiple conditions that promote transient binding are used. In some embodiments, one condition is used for one probe species depending on its Tm and another condition is used for another probe species depending on its Tm and so on for a whole repertoire of probes species, for example, each 5-mer species from a repertoire of 1024 possible 5-mers. In some embodiments, only 512 non-complementary 5-mers are provided (e.g., because both target polynucleotide strands are present in the sample). In some embodiments, each probe addition comprises a mixture of probes comprising 5 specific bases and 2 degenerate bases, (hence 16 heptamers) all labeled with the same label that function as one pentamer in terms of capacity to interrogate sequence. The degenerate bases add stability without increasing the complexity of the probe set.

In some embodiments, the same conditions are provided for a plurality of probes that share the same or similar Tms. In some such embodiments, each probe in the repertoire comprise a different encoding label (or label according to which it is identified). In such instances, the temperature is held through several probe exchanges, before being raised for the next series of probes that share the same or similar Tms.

In some embodiments, during the course of a probe binding period, the temperature is altered so that the binding behavior of the probe at more than one temperature is determined. In some embodiments, an analogue of a melting curve is conducted, where the binding behavior or binding pattern to the target polymer is correlated with a step-wise set of temperatures through a selected range (e.g., from 10° C. to 65° C. or 1° C. to 35° C.).

In some embodiments, the Tms are calculated, for example, by nearest neighbor parameters. In other embodiments, the Tms are empirically derived. For example, the optimal melting temperature range is derived by carrying out a melting curve (measuring extent of melting by absorption for example, over a range of temperatures). In some embodiments, the composition of probe sets is designed according to their theoretically matching Tms that are validated by empirical testing. In some embodiments, the binding is done at a temperature that is substantially below Tm (e.g., up to 33° C. below the calculated Tm). In some embodiments, the empirically defined optimal temperature for each oligo is used for the binding of each oligo in sequencing.

In some embodiments, as an alternative or in addition to modifying the temperature for oligonucleotide probes with different Tms, the concentration of probes and/or salt is altered and/or the pH is altered. In some embodiments, an electrical bias on the surface is repeatedly switched between positive and negative to actively facilitate transient binding between probes and the one or more target molecules.

In some embodiments, the concentration of oligo used is adjusted according to the AT versus GC content of the oligo sequence. In some embodiments, a higher concentration of oligo is provided for oligos with a higher GC content. In some embodiments, buffers that equalize the effect of base composition (e.g., buffers containing, CTAB, Betaine or Chatoropic reagents such as Tetramethyl Ammonium Chloride (TMACl)) are used at concentrations between 2.5 M and 4 M.

In some embodiments, probes are distributed unevenly across the sample (e.g., the flow chamber, the slide, the length of the polynucleotide(s) and/or the ordered array of polynucleotides) due to stochastic effects or to aspects of the design of the sequencing chamber (e.g., eddies in a flow cell that trap probes in a corner or against the wall of a nanochannel). Local depletion of probes is addressed by ensuring there is efficient mixing or agitation of the probe solution. In some instances, this is done with acoustic waves, by including particles in solution that produce turbulence and/or by structuring the flow cell (e.g., herringbone pattern on one or more surfaces) to produce turbulent flows. In addition, due to laminar flow present in flow cells, there is typically little mixing and the solution close to the surfaces mixes very little with the bulk solution. This creates a problem in removing reagents/binding probes that are close to the surface and to bring fresh reagents/probes to the surfaces. The above turbulence creating approaches can be implemented to combat this, and/or extensive fluid flow/exchange over the surface can be conducted. In some embodiments, after the target molecules have been arrayed, non-fluorescent beads or spheres are attached to the surface, giving the surface landscape a rough texture. This creates the eddies and currents needed to more effectively mix and/or exchange fluids close to the surface.

In some embodiments, the entire repertoire or subsets are added together. In some such embodiments, a buffer that equalizes base composition effects (e.g., TMACl or Guanidinium thiocyanate and others, as described in U.S. Pat. Appl. No. 2004/0058349) is used. In some embodiments, probe species with the same or similar Tms are added together. In some embodiments, the probe species added together are not differentially labeled. In some embodiments, the probe species added together are differentially labeled. In some embodiments, the differential labels are labels with emissions that have different brightness, lifetime or wavelength, for example, and/or combinations of such physical properties.

In some embodiments, two or more oligos are used together, and their location of binding determined without provision to distinguish between the signals of the different oligos (e.g., the oligos are labeled with the same color). When both strands of a duplex are available, obtaining binding site data from both strands permits differentiation between the two or more oligonucleotides as part of an assembly algorithm. In some embodiments, one or more reference probes are added together with each probe of the repertoire the assembly algorithm can then use the binding locations of such reference probes to scaffold or anchor the sequence assembly.

In one alternative embodiment, the probes bind stably but an external trigger that switches the environment to off mode controls their transience. In non-limiting embodiments, the trigger is heat, pH, electric field or reagent exchange that cause the probes to unbind. Then the environment is switched back to on mode, allowing probes to bind again. In some embodiments, when the binding does not saturate all sites in the first round of binding, the oligos in the second cycle of binding bind to a different set of sites than the first. In some embodiments, these cycles are carried out multiple times at a controllable rate.

In some embodiments, the transient binding persists for less than or equal to 1 millisecond, less than or equal to 50 milliseconds, less than or equal to 500 milliseconds, less than or equal to 1 microsecond, less than or equal to 10 microseconds, less than or equal to 50 microseconds, less than or equal to 500 microseconds, less than or equal to 1 second, less than or equal to 2 seconds, less than or equal to 5 seconds, or less than or equal to 10 seconds.

With the transient binding approach ensuring a continuous supply of fresh probes, photo bleaching of fluorophores does not cause significant issues, and sophisticated field stops or Powell lenses are not needed to limit illumination. Therefore, the choice of fluorophore (or the provision of an antifade, redox system) is not that important, and in some such embodiments a relatively simple optical system is constructed (e.g., a f-stop, that prevents illumination of molecules that are not in the field of view of the camera, would not be a high requirement).

In some embodiments, another advantage of transient binding is that multiple measurements can be made at every binding site along a polynucleotide, thus increasing confidence in the accuracy of a detection. For example, in some cases, due to the typical stochastic nature of molecular processes, a probe binds to an incorrect location. With transiently bound probes, such an outlier, isolated binding event can be discarded, and only those binding events that are corroborated by multiple detected interactions are accepted as valid detection events for the purpose of sequence determination.

Detection of Transient Binding and Localization of Binding Sites.

Transient binding is an integral component enabling sub-diffraction levels of localization. There is a probability at any time that each probe in the set of transiently binding probes will either be bound to the target molecule or be present in solution. Thus, not all of the binding sites will be bound by a probe at any one time. This allows the detection of binding events at sites that are closer than the diffraction limit of light (e.g., two sites that are only 10 nm apart on the target molecule). For example, if the sequence AAGCTT is repeated after 60 bases, that means the repeated sequences will be approximately 20 nm apart (when the target is elongated and straightened to Watson-Crick base lengths of approximately 0.34 nm). Twenty nanometers would not normally be distinguishable by optical imaging. However, if probes bind to the two sites at different times during imaging, they are individually detected. This permits super-resolution imaging of the binding events. Nanometric precision is particularly important for resolving repeats and determining their number.

In some embodiments, the multiple binding events to a location in the target are not from a single probe sequence, but are determined by analyzing the data from the repertoire, and taking into account events that occur from partially overlapping sequences. In one example, the same (actually a sub-nanometically close) location is bound by probe ATTAAG and TTAAGC, which are 6-mers that share a common 5 base sequence and each would validate the other, as well as extending the sequence one base on either side of the 5 base. In some cases, the base on each side of the 5 base sequence is a mismatch (mismatches at the ends are typically expected to be tolerated more than mismatches that are internal) and only the 5 base sequence is that is present in both binding events is validated.

In some alternative embodiments, the transient single molecule binding is detected by non-optical method. In some embodiments, the non-optical method is an electrical method. In some embodiments, the transient single molecule binding is detected by non-fluorescence methods where there is no direct excitation method, rather a bioluminescence or chemiluminesence mechanism is used.

In some embodiments, each base in a target nucleic acid is interrogated by multiple oligos whose sequences overlap. This repeated sampling of each base permits the detection of rare single nucleotide variants or mutations in the target polynucleotide.

Some embodiments of the present disclosure consider the repertoire of binding interactions (above a threshold binding duration) that each oligonucleotide has had with the polynucleotide under analysis. In some embodiments, the sequencing does not only comprise stitching or reconstructing sequence from a perfect match but obtains the sequence by first analyzing the binding proclivities of each oligo. In some embodiments, the transient binding is recorded as a means of detection but is not used for improving the localization.

Imaging Techniques to Detect Optical Activity and Determine Localization of Binding Sites.

Block 214.

Locations on the test substrate and a duration of each respective instance of optical activity occurring during the exposing using a two-dimensional imager are measured.

Measuring the location on the test substrate comprises inputting a frame of data measured by the two-dimensional imager into a trained convolutional neural network. The frame of data comprises the respective instance of optical activity among a plurality of instances of optical activity. Each instance of optical activity in the plurality of instances of optical activity corresponds to an individual probe binding to a portion of the fixed first strand or the fixed second strand, and. Responsive to the inputting, the trained convolutional neural network identifies a position on the test substrate of each of one or more instances of optical activity in the plurality of instances of optical activity.

In some embodiments, the detector is a two-dimensional detector, and the binding events are localized to a nanometer accuracy (e.g., by using a single molecule localization algorithm). In some embodiments, the interaction characteristics comprise the duration of each binding event, which corresponds to the affinity of the probe(s) with the molecule. In some embodiments, the characteristic is the location on a surface or matrix, which corresponds to the location within an array of a particular molecule (e.g., a polynucleotide corresponding to a specific gene sequence).

In some embodiments, each respective instance of optical activity has an observation metric that satisfies a predetermined threshold. In some embodiments, the observation metric comprises a duration, a signal to noise, a photon count, or an intensity. In some embodiments, the predetermined threshold is satisfied when the respective instance of optical activity is observed for one frame. In some embodiments, the intensity of the respective instance of optical activity is comparatively low, and the predetermined threshold is satisfied when the respective instance of optical activity is observed for a tenth of one frame.

In some embodiments, the predetermined threshold distinguishes between (i) a first form of binding in which each residue of the unique N-mer sequence binds to a complementary base in the fixed first strand or the fixed second strand of the nucleic acid, and (ii) a second form of binding in which there is at least one mismatch between the unique N-mer sequence and a sequence in the fixed first strand or the fixed second strand of the nucleic acid that the respective oligonucleotide probe has bound to form the respective instance of optical activity.

In some embodiments, each respective oligonucleotide probe in the set of oligonucleotide probes has its own corresponding predetermined threshold.

In some embodiments, the predetermined threshold is determined based on observing 1 or more, 2 or more, 3 or more, 4 or more, 5 or more, or 6 or more binding events at a particular location along a polynucleotide.

In some embodiments, the predetermined threshold for each respective oligonucleotide probe in the set of oligonucleotide probes is derived from a training dataset (e.g., a dataset derived from information obtained by applying the method to sequencing lambda phage).

In some embodiments, the predetermined threshold for each respective oligonucleotide probe in the set of oligonucleotide probes is derived from a training dataset. The training set comprises, for each respective oligonucleotide probe in the set of oligonucleotide probes, a measure of the observation metric for the respective oligonucleotide probe upon binding to a reference sequence such that each residue of the unique N-mer sequence of the respective oligonucleotide probe binds to a complementary base in the reference sequence.

In some embodiments, the reference sequence is fixed on a reference substrate. In some embodiments, the reference sequence is included with the nucleic acid and fixed on the test substrate. In some embodiments, the reference sequence comprises all or a portion of the genome of, PhiX174, M13, lambda phage, T7 phage, *Escherichia coli*, *Saccharomyces cerevisiae*, or *Saccharomyces pombe*. In some embodiments, the reference sequence is a synthetic construct of known sequence. In some embodiments, the reference sequence comprises all or a portion of rabbit globin RNA (e.g., when the nucleic acid comprises RNA or when only one strand of a polynucleotide is sequenced).

In some embodiments, the exposing is in the presence of a first label in the form of an intercalating dye. Each oligonucleotide probe in the set of oligonucleotide probes is bound with a second label. The first label and the second label have overlapping donor emission and acceptor excitation spectra that causes one of the first label and the second label to fluoresce when the first label and the second label are in close proximity to each other. The respective instance of optical activity is from a proximity of the intercalating dye, intercalating the respective heteroduplex between the oligonucleotide and the fixed first strand or the fixed second strand, to the second label. In some embodiments, the exposing and the fluorescence comprise a Förster resonance energy transfer (FRET) method. In such embodiments, the intercalating dye comprises a FRET donor, and the second label comprises a FRET acceptor.

In some embodiments, the signal is detected by FRET from intercalating dye to a label on the probe or the target sequence. In some embodiments, after the target is immobilized the ends of all target molecules are labelled, for example, by terminal transferase incorporating fluorescently labelled nucleotides that act as FRET partners. In some such embodiments, the probe is labeled at one of its ends with a Cy3B or Atto 542 label.

In some embodiments, the FRET is replaced by photo activation. In such embodiments, the donor (e.g., a label on the template) comprises a photo activator, and the acceptor (e.g., the label on the oligonucleotide) becomes a fluorophore in an inactivated or darkened state (e.g. Cy5 label can be darkened by caging with 1 mg/mL NaBH4 in 20 mM Tris at pH 7.5, 2 mM EDTA, and 50 mM NaCl before the fluorescent imaging experiments). In such embodiments, the fluorescence of the darkened fluorophore is switched on when in close proximity to the activator.

In some embodiments, the exposing is in the presence of a first label in the form of an intercalating dye (e.g., a photo activator). Each oligonucleotide probe in the set of oligonucleotide probes is bound with a second label (e.g., a darkened fluorophore). The first label causes the second label to fluoresce when the first label and the second label are in close proximity to each other. The respective instance of optical activity is from a proximity of the intercalating dye, intercalating the respective heteroduplex between the oligonucleotide and the fixed first strand or the fixed second strand, to the second label.

In some embodiments, the exposing is in the presence of a first label in the form of an intercalating dye (e.g., a darkened fluorophore). Each oligonucleotide probe in the set of oligonucleotide probes is bound with a second label (e.g., a photo activator). The second label causes the first label to fluoresce when the first label and the second label are in close proximity to each other. The respective instance of optical activity is from a proximity of the intercalating dye, intercalating the respective heteroduplex between the oligonucleotide and the fixed first strand or the fixed second strand, to the second label.

In some embodiments, the exposing is in the presence of an intercalating dye. The respective instance of optical activity is from a fluorescence of the intercalating dye intercalating the respective heteroduplex between the oligonucleotide and the fixed first strand or the fixed second strand, where the respective instance of optical activity is greater than a fluorescence of the intercalating dye before it intercalates the respective heteroduplex. The increased fluorescence (100× or more) of the one or more dyes intercalating into the duplex, provides a point source-like signal for the single molecule localization algorithm and allow precise determination of the location of the binding site. The intercalating dyes intercalate into the duplex, producing a significant number of heteroduplex binding events for each binding site that are robustly detected and precisely localized.

In some embodiments, a respective oligonucleotide probe in the set of oligonucleotide probes yields a first instance of optical activity by binding to a complementary portion of the fixed first strand, and a second instance of optical activity by binding to a complementary portion of the fixed second strand. In some embodiments, a portion of the fixed first strand yields an instance of optical activity by binding of its complementary oligonucleotide probe, and a portion of the fixed second strand complementary to the portion of the fixed first strand yields another instance of optical activity by binding of its complementary oligonucleotide probe.

In some embodiments, a respective oligonucleotide probe in the set of oligonucleotide probes yields two or more first instances of optical activity by binding to two or more complementary portions of the fixed first strand and two or more second instances of optical activity by binding two or more complementary portions of the fixed second strand.

In some embodiments, the respective oligonucleotide probe binds to a portion of the fixed first strand or the fixed second strand that is complementary to the respective oligonucleotide probe three or more times during the exposing thereby resulting in three or more instances of optical activity, each instance of optical activity representing a binding event in the plurality of binding events.

In some embodiments, the respective oligonucleotide probe binds to a portion of the fixed first strand or the fixed second strand that is complementary to the respective oligonucleotide probe five or more times during the exposing, thereby resulting in five or more instances of optical activity. Each instance of optical activity represents a binding event in the plurality of binding events.

In some embodiments, the respective oligonucleotide probe binds to a portion of the fixed first strand or the fixed second strand that is complementary to the respective oligonucleotide probe ten or more times during the exposing, thereby resulting in ten or more instances of optical activity, each instance of optical activity representing a binding event in the plurality of binding events.

In some embodiments, the exposing occurs for five minutes or less, four minutes or less, three minutes or less, two minutes or less, or one minute or less.

In some embodiments, the exposing occurs across 1 or more frames of the two-dimensional imager. In some embodiments, the exposing occurs across 2 or more frames of the two-dimensional imager. In some embodiments, the exposing occurs across 500 or more frames of the two-dimensional imager. In some embodiments, the exposing occurs across 5,000 or more frames of the two-dimensional imager. In some embodiments, when the optical activity is sparse (e.g., there are few instances of probe binding), one frame of transient binding is sufficient to localize the signal.

In some embodiments, a length of time of an instance of the exposing is determined by an estimated melting temperature of a respective oligonucleotide probe in the set of oligonucleotide probes used in the instance of the exposing.

In some embodiments, the optical activity comprises fluorescence emissions from a label. A respective label is excited and the corresponding emission wavelengths detected separately using distinct filters in a filter wheel. In some embodiments, the emission lifetimes are measured using a fluorescence lifetime imaging (FLIM) system. Alternatively, the wavelengths are split and projected to different quadrants of a single sensor or onto four separate sensors. A method that uses a prism to split the spectrum over the pixels of a CCD has been described by Lundquit et al., Opt Lett., 33:1026-8, 2008. In some embodiments, a spectrograph is also used. Alternatively, in some embodiments, the emission wavelength is combined with brightness levels to provide information on a probe's dwell time in a binding site.

Several detection methods, such as scanning probe microscopy (including high speed atomic force microscopy) and electron microscopy, are capable of resolving nanometric distances when a polynucleotide molecule is elongated in the plane of detection. However, these methods do not provide information regarding optical activity of fluorophores. There are multiple optical imaging techniques to detect fluorescent molecules at super-resolution precision. These include stimulated emission depletion (STED), stochastic optical reconstruction microscopy (STORM), super-resolution optical fluctuation imaging (SOFI), single molecule localization microscopy (SMLM) and total internal reflection fluorescence (TIRF) microscopy. In some embodiments, a SMLM approach most similar to points accumulation in nanoscale topography (PAINT) is preferred. These methods typically require one or more lasers to excite fluorophores, a focus detection/hold mechanism, a CCD camera an appropriate objective, relay lenses and mirrors. In some embodiments, the detection step involves taking a number of image frames (e.g., a movie or video) to record the binding-on and -off of the probe.

SMLM methods rely on high photon counts. High photon counts improve the precision with which the centroid of the fluorophore-generated of Gaussian pattern is determined, but the need for high photon counts is also associated with long image acquisitions and dependence upon bright and photo stable fluorophores. High solution concentrations of probe is achieved without causing detrimental background by using quenched probes molecular beacons, or having two or more labels of the same type, e.g., one on each side of the oligo. In such embodiments, these labels are quenched in solution via-dye-dye interactions. However, when bound to their target the labels become separated and are able to fluoresce brightly (e.g., twice as brightly as a single dye) making them easier to detect.

In some embodiments, the on-rate of the probes is manipulated (e.g., increased) by increasing probe concentration, increasing temperature, or increasing molecular crowding (e.g., by including PEG 400, PEG 800, etc. in the solution). Decreasing thermal stability of the probe by engineering its chemical components, adding de-stabilizing appendages, or in the case of oligonucleotides, decreasing their lengths, can increase the off-rate. In some embodiments, the off-rate is also accelerated by increasing temperature, reducing salt concentration (e.g., increasing stringency), or altering pH.

In some embodiments, the concentration of probes that are used is increased by making the probes essentially non-fluorescent until they bind. One way to do this is that binding induces a photo activation event. Another is that the labels are quenched until binding occurs (e.g., Molecular Beacons). Another is that the signal is detected as a result of an energy transfer event (e.g., FRET, CRET, BRET). In one embodiment the biopolymer on the surface bears a donor and the probe bears the acceptor) or vice versa. In another embodiment an intercalating dye is provided in solution and upon binding of a labelled probe there is a FRET interaction between the intercalating dye and probe. An example of the intercalating dye is YOYO-1 and an example of the label on the probe is ATTO 655. In another embodiment, intercalating is dye is used without a FRET mechanism—both the single stranded target sequence on the surface and the probe sequence are unlabeled and signal is only detected when binding creates a double strand into which the intercalating dye intercalates. The intercalating dye, depending on its identity, is 100× or 1000× less bright when it is not intercalated into DNA and is free in solution. In some embodiments, either TIRF or highly inclined and laminated optical (HILO) (e.g., as described in Mertz et al., J. of Biomedical Optics, 15(1): 016027, 2010) microscopy is used to eliminate any background signals from the intercalating dye in solution.

However, in some embodiments, high concentrations of labeled probes cause high background fluorescence that obscures detection of the signals on the surface. In some embodiments, this is addressed with a DNA stain or intercalating dye to label the duplex that is formed on the surface. The dyes do not intercalate when the target is single stranded nor with the single stranded probe, but the dyes will intercalate when a duplex is formed between the probe and the target. In some embodiments, the probe is unlabeled, and the signal that is detected is due to the intercalating dye only. In some embodiments, the probe is labeled with a label that acts as a FRET partner to the intercalating dye or DNA stain. In some embodiments, the intercalating dye is the donor and couples with acceptors of different wavelengths, hence allowing the probe to be encoded with multiple fluorophores.

In some embodiments, the detection step involves detecting multiple binding events to each complementary site. In some embodiments, the multiple events are from the same probe molecule binding on or off, or being replaced by another molecule of the same specificity (e.g., it is specific to the same sequence or molecular structure), and this occurs multiple times. In some embodiments, the binding on- or off-rate is not affected by altering conditions. For example, both binding-on and binding-off occurs under the same conditions (e.g., salt concentration, temperature, etc.) and is due to the probe-target interaction being weak.

In some embodiments, sequencing is conducted by imaging multiple on-off binding events at multiple locations on a single target polynucleotide that is shorter, the same length or within an order of magnitude of the probe length. In such embodiments, a longer target polynucleotide is fragmented or a panel of fragments has been pre-selected and arrayed on a surface so that each polynucleotide molecule is individually resolvable. In these cases, the frequency or duration of probe binding to a specific location is used to determine whether a probe corresponds to the target sequence. The frequency or duration of the probe binding determines whether a probe corresponds to all or part of the target sequence (with the remaining bases mismatched).

Occurrence of side-by-side overlap between the target polynucleotide is detected in some embodiments by the increase fluorescence from the DNA stain. In some embodiments where stain is not used, overlap is detected by the increase in frequency of apparent binding sites along the segment. For example, in some instances where diffraction-limited molecules optically appear to be overlapping but are not actually physically overlapping, they are super-resolved using single molecule localization as described elsewhere in the present disclosure. Where end-on-end overlap does occur, in some embodiments, labels marking the ends of polynucleotides are used to distinguish juxtaposed polynucleotides from true contiguous lengths. In some embodiments, such optical chimeras are dismissed as artifacts if many copies of the genome are expected and only one occurrence of the apparent chimera is found. Again, in some embodiments where the ends of molecules (diffraction-limited) optically appear to overlap, but are not physically overlapping, they are resolved by the methods of the present disclosure. In some embodiments, the location determination is so precise that signals emanating from very close labels are resolved.

In some embodiments, sequencing is conducted by imaging multiple on-off binding events at multiple locations on a single target polynucleotide that is longer than the probe. In some embodiments, the location of probe binding events over the single polynucleotide are determined. In some embodiments, the location of probe binding events over the single polynucleotide is determined by elongating the target polynucleotide, so that different locations along its length are detected and resolved.

In some embodiments, differentiating optical activity of unbound probes from probes that have bound to the target molecule requires rejection or removal of signal from probes that have not bound. In some such embodiments, this is done using, for example, an evanescent field or waveguide for illumination or by utilizing FRET pair labels or by utilizing photo activation to detect probes in specific locations (e.g., as described in Hylkje et al., Biophys J. 2015; 108(4): 949-956).

In some embodiments, the probes are not labeled, but the interaction with the target is detected by a DNA stain such as an intercalating dye 1302, which intercalates into the duplex and begins fluorescing 1304 as binding occurs or has occurred (e.g., as illustrated in FIGS. 13A-13C). In some embodiments, one or more intercalating dyes intercalate into the duplex at any one time. In some embodiments, the fluorescence emitted by an intercalating dye once it is intercalated is orders of magnitude greater than the fluorescence due to intercalating dye floating free in solution. For example, the signal from intercalated YOYO-1 dyes is about 100× greater than the signal from YOYO-1 dye free in solution. In some embodiments, when a lightly stained (or partially photo bleached) double-stranded polynucleotide is imaged, individual signals along the polynucleotide that are observed likely correspond to single intercalating dye molecules. To facilitate exchange of YOYO-1 dye in a duplex and to obtain a bright signal Redox-Oxidation system (ROX) comprising Methyl Viologen and ascorbic acid are provided in the binding buffer in some embodiments.

In some embodiments, sequencing on single molecules by detecting the incorporation of nucleotides labeled with a single dye molecule (e.g., as is done in Helicos and PacBio sequencing) introduces errors when the dye is not detected. In some instances, this is because the dye has photo bleached, the cumulative signal detected is weak due to dye blinking, the dye emits too weakly or the dye enters into a long dark photophysical state. In some embodiments, this is overcome in a number of alternative ways. The first is to label the dye with robust individual dyes that have favorable photophysical properties (e.g., Cy3B). Another is to provide buffer conditions and additives that reduce photo bleaching and dark photophysical states (e.g., beta-mercaptoethanol, Trolox, Vitamin C and its derivatives, redox systems). Another is to minimize exposure to light (e.g., having more sensitive detectors requiring shorter exposures or providing stroboscopic illumination). The second is to label with nanoparticles such as quantum dots (e.g., Qdot 655), fluorospheres, nanodiamond, plasmon resonant particles, light scattering particles, etc., instead of single dyes. Another is to have many dyes per nucleotide rather than a single dye (e.g., as illustrated in FIGS. 14C and 14D). In this case the multiple dyes 1414 are organized in a way that minimizes their self-quenching (e.g., using rigid nanostructures 1412 such as DNA origami that spaces them far enough apart) or a linear spacing via rigid linker.

In some embodiments, the detection error rate is further reduced (and signal longevity increased) in the presence in the solution of one or more compound(s) selected from urea, ascorbic acid or salt thereof, and isoascorbic acid or salt thereof, beta-mercaptoethanol (BME), DTT, a redox system, or Trolox.

In some embodiments, the transient binding of the probes to the target molecules alone is sufficient to reduce errors due to dye photophysics. The information obtained during the imaging step is an aggregate of many on/off interactions of different label-bearing probes. Thus, even if one label is photo bleached or is in a dark state, the labels on other binding probes that land on the molecule are not photo bleached or in a dark state and will thus provide information on the location of their binding sites in some embodiments.

In some embodiments, the signal from the label in each transient binding event is projected through an optical path (typically, providing a magnification factor) to cover more than one pixel of the 2D detector. The point spread function (PSF) of the signal is plotted and the centroid of the PSF taken as the precise location of the signal. In some embodiments, this localization is done to sub-diffraction (e.g., super resolution) and even sub-nanometer accuracy. The localization accuracy is inversely proportional to the number of photons collected. Therefore, the more photons emitted per second by a fluorescent label or the longer the photons are collected, the higher the accuracy.

In one example, as illustrated in FIGS. 10A and 10B, both the number of binding events at each binding site and the number of photons collected is correlated with the degree of localization that is achieved. For a target polymer 1002, the smallest number of binding events 1004-1 and the fewest number of photons 1008-1 recorded for a binding site are correlated with the least precise localizations 1006-1 and 1010-1, respectively. As either the number of binding events 1004-2, 1004-3 or the number of photons recorded 1008-2, 1008-3 increase for a binding site, the degree of localization increases 1006-2, 1006-3 and 1010-2, 1010-3, respectively. In FIG. 10A, a differing number of detected stochastic binding events (e.g., 1004-1, 1004-2, 1004-4) of labeled probes onto a polynucleotide 1002 results in differing degrees of localization of the probes (1006-1, 1006-2, 1006-3), where a larger number of binding events (e.g., 1004-2) is correlated with a higher degree of localization (e.g., 1006-2), and a smaller number of binding events (e.g., 1004-1) is correlated with a lower degree of localization (e.g., 1006-1). In FIG. 10B, a differing number of photons (e.g., 1008-1, 1008-2, and 1008-3) that are detected similarly results in differing degrees of localization (1010-1, 1010-2, and 1010-3 respectively).

In an alternative embodiment, the signal from the label in each transient binding event is not projected through an optical magnification path. Instead, the substrate (typically an optically transparent surface upon which the target molecules reside) is directly coupled to the two-dimensional detector array. When the pixels of the detector array are small (e.g., one micron squared or less), then a one-to-one projection of the signals on the surface allows the binding signal to be localized with at least one-micron accuracy. In some embodiments where the nucleic acid has been stretched sufficiently (e.g., where two kilobases of the polynucleotide has been stretched to 1 micron in length), signals that are a mere two kilobases apart are resolved. For example, in the case of 6-mer probes where signals would be expected to occur every 4096 bases or every 2 microns, this resolution will be sufficient to unequivocally localize individual binding sites. A signal that falls partially between two pixels, provides intermediate locations (e.g., the resolution could be 500 nm for a pixel one micron squared if a signal falls between two pixels). In some embodiments, the substrate is physically translated in relation to the two-dimensional array detector (e.g., in increments of 100 nm) to provide higher resolution. In such embodiments, the device is smaller (or thinner), as it does not need lenses or space in between lenses. In some embodiments, translation of the substrate also provides a direct conversion of molecular storage readout into electronic readout more compatible with existing computers and databases.

In some embodiments, to capture high speed transient binding, the capture frame rate is increased and the data transfer rate is increased over standard microscopy techniques. In some embodiments, the speed of the process is increased by coupling high frame detection with an increased concentration of probes. However, individual exposures remain at a minimum threshold exposure to reduce electronic noise associated with each exposure. The accumulated electronic noise of a 200 millisecond exposure would be less than two 100 millisecond exposures.

Faster CMOS cameras are becoming available that will enable faster imaging. For example, the Andor Zyla Plus allows up to 398 frames per second over 512×1024 pixels squared with just a USB 3.0 connection and is even faster over restricted regions of interest (ROI) or a CameraLink connection.

An alternative approach for obtaining fast imaging is to use a galvo mirror or digital micromirror to send temporal incremented images to different sensors. The correct order of the frames of the movie is then reconstructed by interleaving frames from the different sensors according to their time of acquisition.

The transient binding process can be sped up by tuning various biochemical parameters, such as salt concentration. There are a number of cameras with high frame rates that can be used to match the speed of binding, often the field of view is restricted to obtain a faster readout from a subset of pixels. One alternative approach is to use a galvanometer mirror to temporally distribute consecutive signals to different regions of a single sensor or to separate sensors. The latter allows the utilization of the full field of view of a sensor but increases overall temporal resolution when the distributed signals are compiled Build a Dataset of Multiple Binding Events.

Block 218.

Repeat the exposing and measuring for respective oligonucleotide probes in the set of oligonucleotide probes, thereby obtaining a plurality of sets of positions on the test substrate, each respective set of positions on the test substrate corresponding to an oligonucleotide probe in the set of oligonucleotide probes.

In some embodiments, the set of oligonucleotide probes comprises a plurality of subsets of the oligonucleotide probes and the repeating the exposing and measuring is performed for each respective subset of oligonucleotide probes in the plurality of subsets of oligonucleotide probes.

In some embodiments, each respective subset of oligonucleotide probes comprises two or more different probes from the set of oligonucleotide probes. In some embodiments, each respective subset of oligonucleotide probes comprises four or more different probes from the set of oligonucleotide probes. In some embodiments, set of oligonucleotide probes consists of four subsets of oligonucleotide probes.

In some embodiments, the method further comprises dividing the set of oligonucleotide probes into the plurality of subsets of oligonucleotide probes based on a calculated or experimentally derived melting temperature of each oligonucleotide probe. Oligonucleotide probes with similar melting temperatures are placed in the same subset of oligonucleotide probes by the dividing. Further, a temperature or a duration of an instance of the exposing is determined by an average melting temperature of the oligonucleotide probes in the corresponding subset of oligonucleotide probes.

In some embodiments, the method further comprises dividing the set of oligonucleotide probes into the plurality of subsets of oligonucleotide probes based on a sequence of each oligonucleotide probe, where oligonucleotide probes with overlapping sequences are placed in different subsets.

In some embodiments, repeating the exposing and measuring is performed for each single oligonucleotide probe in the set of oligonucleotide probes.

In some embodiments, the exposing is done for a first oligonucleotide probe in the set of oligonucleotide probes at a first temperature and repeating the exposing and measuring includes performing the exposing and the measuring for the first oligonucleotide at a second temperature.

In some embodiments, the exposing is done for a first oligonucleotide probe in the set of oligonucleotide probes at a first temperature. Instances of the repeating the exposing and measuring include performing the exposing and the measuring for the first oligonucleotide at each of a plurality of different temperatures. The method further comprises constructing a melting curve for the first oligonucleotide probe using the measured locations and durations of optical activity recorded by the measuring for the first temperature and each temperature in the plurality of different temperatures.

In some embodiments, the test substrate is washed prior to repeating the exposing and measuring, thereby removing one or more respective oligonucleotide probes from the test substrate prior to exposing the test substrate to another set of oligonucleotide probes. Optionally, first the probes are replaced with one or more wash solutions, then the next set of probes are added.

In some embodiments, the measuring the location on the test substrate comprises identifying and fitting the respective instance of optical activity with a fitting function to identify and fit a center of the respective instance of optical activity in a frame of data obtained by the two-dimensional imager. The center of the respective instance of optical activity is deemed to be the position of the respective instance of optical activity on the test substrate.

In some embodiments, the fitting function is a Gaussian function, a first moment function, a gradient-based approach, or a Fourier transform. A Gaussian fit will only be an approximation of the PSF of microscope, but the addition of a spline (e.g., a cubic spline) or a Fourier transform approach, in some embodiments, serves to improve the accuracy of determining the center of mass of the PSF (e.g., as described in Babcock et al., Sci Rep. 7:552, 2017 and Zhang et al., 46:1819-1829, 2007).

After data processing, single molecule localization identifies (e.g., due to the color detected) which of the probes from set 1-5, have the same localization footprint on the polynucleotide (e.g., which bind to the same nanometric location). In one example, the nanometric location is defined with precision of 1 nm center (+/−0.5 nm), and all probes whose centroid of PSF falls within the same 1 nm, would thus be binned together. Each single defined oligo species must bind multiple times (e.g., depending on number of photons emitted and collected) to enable accurate localization to a nanometer (or sub-nanometer) centroid.

In some embodiments, the nanometric or sub-nanometric localization determines, for example, that the first base is A, the second G, the third T, the fourth C and the fifth T for an oligo sequence of 5'-AGTCG-3'. Such a pattern suggests a target sequence of 5'-CGACT-3'. Thus, all single-base defined 1024 5-mer oligo probes are applied or tested in just five cycles, where each cycle comprises both an oligo addition and washing step. In such implementations the concentration of each specific oligo in the set is lower than it would be when used alone. In this case, acquisition of data is taken for a longer time in order to reach a threshold number of binding events. Also, higher concentrations of the degenerate oligo are used in some embodiments than a specific oligo. In some embodiments, this coding scheme is carried out by direct labeling of the probe, for example, by synthesizing or conjugating the label at the 3' or 5' of the oligos. However, in some alterative embodiments, this is done by indirect labeling (e.g., by attaching a flap sequence to each labeled oligo).

In some embodiments, the location of each oligo is precisely defined by determining PSFs for multiple events for that location and then is corroborated by partial sequence overlap from offset events (and where, available, data from the complementary strand of the duplex). This embodiment is highly reliant on the single molecule localization of probe binding to one or a few nanometers.

In some embodiments, the respective instance of optical activity persists across a plurality of frames measured by the two-dimensional imager. The measuring the location on the test substrate comprises identifying and fitting the respective instance of optical activity with a fitting function across the plurality of frames to identify a center of the respective instance of optical activity across the plurality of frames. The center of the respective instance of optical activity is deemed to be the position of the respective instance of optical activity on the test substrate across the plurality of frames. In some embodiments, the fitting function finds the center on each frame in the plurality of frames individually. In other embodiments, the fitting function alternatively finds the center on each frame collectively across the plurality of frames.

In some embodiments, the fitting involves a tracking step where if a localization immediately adjacent (e.g., within half a pixel) in the next frame, it will average them together, weighted by how bright they are; it assumes this is the same binding event. However, if there are events separated by multiple frames (e.g., at least a 5 frame gap, at least a 10 frame gap, at least a 25 frame gap, at least a 50 frame gap, or at least a 100 frame gap between binding events), then the fitting function assumes they are distinct binding events. Tracking distinct binding events helps to increase the confidence in sequence assignment.

In some embodiments, the measuring resolves the center of the respective instance of optical activity to a position on the test substrate with a localization precision of at least 20 nm. In some embodiments, the measuring resolves the center of the respective instance of optical activity to a position on the test substrate with a localization precision of at least 2 nm, at least 60 nm, at least 6 nm. In some embodiments, the measuring resolves the center of the respective instance of optical activity to a position on the test substrate with a localization precision of between 2 nm and 100 nm. In some embodiments, the measuring resolves the center of the respective instance of optical activity to a position on the test substrate, where the position is a sub-diffraction limited position. In some embodiments, the resolution is more limiting than the precision.

In some embodiments, measuring the location on the test substrate and the duration of the respective instance of optical activity measures more than 5000 photons at the location. In some embodiments, measuring the location on the test substrate and the duration of the respective instance of optical activity measures more than 50,000 photons at the location or more than 200,000 photons at the location.

Each dye has a maximum rate at which it generates photons (e.g., 1 KHz-1 MHz). For example, for some dyes it is only possible to measure 200,000 photons in one second. A typical lifetime for a dye is 10 nanoseconds. In some embodiments, measuring the location on the test substrate and the duration of the respective instance of optical activity measures more than 1,000,000 photons at the location.

In some instances, certain outlier sequences bind in a non-Watson Crick manner or a short motif leads to inordinately high on-rate or low off-rate. For example, some purine-polypryrimidine interactions between RNA and DNA are very strong (e.g., RNA motifs such as AGG). These not only have lower off rates, but also higher on rates due to more stable nucleation sequence. In some cases, binding occurs from outliers that do not necessarily conform to certain known rules. In some embodiments, algorithms are used to identify such outliers or take the expectation of such outliers into account.

In some embodiments, the respective instance of optical activity is more than a predetermined number of standard deviations (e.g., more than 3, 4, 5, 6, 7, 8, 9, or 10 standard deviations) over a background observed for the test substrate.

In some embodiments, the exposing is done for a first oligonucleotide probe in the set of oligonucleotide probes for a first period of time. In some such embodiments, the repeating the exposing and measuring includes performing the exposing for a second oligonucleotide for a second period of time. The first period of time is greater than the second period of time.

In some embodiments, the exposing is done for a first oligonucleotide probe in the set of oligonucleotide probes for a first number of frames of the two-dimensional imager. In some such embodiments, the repeating the exposing and measuring includes performing the exposing for a second oligonucleotide for a second number of frames of the two-dimensional imager. The first number of frames is greater than the second number of frames.

In some embodiments, complementary probes in one or more tiling sets are used to bind to each of the strands of a denatured duplex. As illustrated by FIG. 11B, it is possible to determine the sequence of at least a portion of the nucleic acid from the plurality of sets of positions on the test substrate comprises determining a first tiling path 1114 corresponding to the fixed first strand 1110 and a second tiling path 1116 corresponding to the fixed second strand 1112.

In some embodiments, a break in the first tiling path is resolved using a corresponding portion of the second tiling path. In some embodiments, a break in the first tiling path or the second tiling path is resolved using a reference sequence. In some embodiments, a break in the first tiling path or the second tiling path is resolved using corresponding portions of a third tiling path or a fourth tiling path obtained from another instance of the nucleic acid.

In some embodiments, a confidence in sequence assignment of the sequence for each binding site is increased using corresponding portions of the first tiling path and the second tiling path. In some embodiments, a confidence in sequence assignment of the sequence is increased using corresponding portions of a third tiling path or a fourth tiling path obtained from another instance of the nucleic acid.

Alignment or Assembly of the Sequence.

Block 222.

The sequence of at least a portion of the nucleic acid is determined from the plurality of sets of positions on the test substrate by compiling the positions on the test substrate represented by the plurality of sets of positions.

Preferably the contiguous sequence is obtained via de novo assembly. However, in some embodiments a reference sequence is also used to facilitate assembly. This allows a de novo assembly to be constructed. When complete genome sequencing requires a synthesis of information from multiple molecules spanning the same segment of the genome (ideally molecules that are derived from the same parental chromosome), algorithms are need to process the information obtained from multiple molecules. One algorithm is of the kind that aligns molecules based on sequences that are common between multiple molecules, and fills in the gap in each molecule by imputing from co-aligned molecules where the region is covered (e.g., a gap in one molecule is covered by a read in another, co-aligned molecule).

In some embodiments, shotgun assembly methods (e.g., as described in Schuler et al., Science 274:540-546, 1996) are adapted to carry out the assembly using sequence assignments obtained as described herein. An advantage of the current method over shotgun sequencing is that a multitude of reads are pre-assembled as they were collected from full-length, intact target molecules (e.g., it is already known the location of reads with respect to each other, and the length of gaps between reads is known). In various embodiments, a reference genome is used to facilitate assembly, either of the long-range genome structure or the short-range polynucleotide sequence or both. In some embodiments, the reads are partially de-novo assembled and then aligned to the reference and then the reference-assisted assemblies is de novo assembled further. In some embodiments, various reference assemblies are used to provide some guidance for a genome assembly. However, in typical embodiments, information obtained from actual molecules (especially if it is corroborated by two or more molecules) is weighted greater than any information from reference sequences.

In some embodiments, the targets from which sequence bits are obtained are aligned based on segments of sequence overlap between the targets, and a longer in silico contig and ultimately the sequence of the entire chromosome is generated.

In some embodiments, the identity of a polynucleotide is determined by the pattern of probe binding along its length. In some embodiments, the identity is the identity of a RNA species or an RNA isoform. In some embodiments, the identity is the location in a reference to which the polynucleotide corresponds.

In some embodiments, the localization accuracy or precision is not sufficient to stitch sequence bits together. In some embodiments, a subset of probes is found to bind within a specific locality but strictly from the localization data their order is hard to determine with confidence in some embodiments. In some embodiments, the resolution is diffraction limited. In some embodiments, the short-range sequence within the locality or diffraction-limited spot is assembled by sequence overlap of the probes that locate within the locality or spot. The short-range sequence is thus assembled for example, by using information about how the individual sequences of the subset of oligos overlap. In some embodiments, short range sequences constructed in this way are then stitched together, based on their order on the polynucleotide, into a long-range sequence. The long-range-sequence is thus obtained by conjoining the short-range sequence obtained from adjacent or overlapping spots.

In some embodiments (e.g., for a target polynucleotide that is natively double-stranded), the reference sequence and sequence information obtained for the complementary strand are used to facilitate sequence assignment.

In some embodiments, the nucleic acid is at least 140 bases in length and the determining determines a coverage of the sequence of the nucleic acid sequence of greater than 70%. In some embodiments, the nucleic acid is at least 140 bases in length and the determining determines a coverage of the sequence of the nucleic acid sequence of greater than 90%. In some embodiments, the nucleic acid is at least 140 bases in length and the determining determines a coverage of the sequence of the nucleic acid sequence of greater than 99%. In some embodiments, the determining determines a coverage of the sequence of the nucleic acid sequence of greater than 99%.

Non-Specific or Mismatching Binding Events.

In general, sequencing assumes that the target polynucleotide contains nucleotides that are complementary to the ones bound. However, this is not always the case. A binding mismatch error is an example of a case where this assumption does not hold. Nevertheless, mismatching, when it occurs according to known rules or behavior, is useful in determining the sequence of the target. The use of short oligonucleotides (e.g., 5-mers) means that the effect of a single mismatch has a large effect on stability, as one base is 20% of the 5-mer length. Hence, at the appropriate conditions, exquisite specificity is obtained by short oligo probes. Even so, mismatches can occur and because of the stochastic nature of molecular interactions, their binding duration might in some cases, not be distinguishable from binding where all 5 bases are specific. However, algorithms that are used to perform base (or sequence) calling and assembly often take the occurrence of mismatches into account. Many types of mismatches are predictable and conform to certain rules. Some of these rules are derived by theoretical considerations while others are derived experimentally (e.g., as described by Maskos and Southern, Nucleic Acids Res 21(20): 4663-4669, 2013; Williams et al., Nucleic Acids Res 22:1365-1367, 1994).

The effects of non-specific binding to the surface are mitigated by such non-persistence of probe binding to non-specific sites is not persistent and once one imager has occupied a non-specific (e.g., not on the complementary target sequence) binding site it can get bleached but in some cases remains in place, blocking further binding to that location (e.g. an interaction due to a G-Quartet formation). Typically, the majority of the non-specific binding sites, which prevent resolution of the imager binding to the target polynucleotide, are occupied and bleached within the early phase of imaging, leaving the on/off binding of the imager to the polynucleotide site to be easily observed thereafter. Hence in one embodiment, high laser power is used to bleach probes that initially take up non-specific binding sites, optionally images are not taken during this phase, and then the laser power is optionally reduced and imaging is started to capture the on-off binding to the polynucleotide. After the initial non-specific binding, further non-specific binding is less frequent (because probes that have bleached often remain stuck to the non-specific binding sites) and, in some embodiments, are computationally filtered out by applying a threshold, for example, to be considered as specific binding to the docking site, the binding to the same location must be persistent, e.g. should occur at the same site at least 5 times or more preferably at least 10 times. Typically, around 20 specific binding events to the docking site are detected.

Another means to filter out binding that is non-specific, is that the fluorophore signals must correlate with the position of the linear strand of the target molecule that is stretched on the surface. In some embodiments, it is possible to determine the linear strand's position either by staining the linear strand directly or by interpolating a line through persistent binding sites. In general, signals that do not fall along a line, whether they are persistent or not, are discarded in some embodiments. Similarly, when a supramolecular lattice is used, binding events that do not correlate with the known structure of the lattice are discarded in some embodiments.

The multiple binding events also increase specificity. For instance, rather than establishing the identity of a moiety or sequence being detected on a single "call," a consensus is obtained from multiple calls. Also the multiple binding events to a target moiety or sequence allow binding to actual locations to be differentiated from non-specific binding events, where binding (of a threshold duration) is less likely to occur multiple times at the same location. Also it is observed that the measurement of multiple binding events over time allows the accumulation of non-specific binding events to the surface to be bleached out, after which little non-specific binding is detected again. This is likely to be because although the signals from the nonspecific binding is bleached out, the non-specific binding sites remain occupied or blocked.

In some embodiments, the sequencing is complicated by mismatch and non-specific binding on the polynucleotide. In order to circumvent the effects of non-specific binding or outlier events, in some embodiments, the method prioritizes signals based on their location and persistence. Priority due to location is predicated upon whether probes co-localize for example, on a stretched polymer or supramolecular lattice (e.g., a DNA origami grid), including location within the lattice structure. Priority due to persistence of binding concerns duration of binding and the frequency of binding and uses the priority list to determine the likelihood of a full match a partial match or non-specific binding. The priority that is established for each binding probe in a panel or repertoire is used to determine the correctness of a signal.

In some embodiments, priority is used to facilitate signal verification and base calling by determining whether the signal persistence duration greater than a predefined threshold, whether the signal repetition or frequency is greater than a predetermined threshold, whether the signal correlates with the location of the target molecule, and/or whether the number of photons collected is greater than a predefined threshold. In some embodiments, when the answer to any of these determination is true, the signal is accepted as real (e.g., as not a mismatch or a non-specific binding event).

In some embodiments, mismatches are distinguished by their temporal binding pattern and hence are considered as a secondary layer of sequence information. In such embodiments, when a binding signal is judged to be a mismatch due to its temporal binding characteristics, the sequence bit is bioinformatically trimmed to remove putative mismatching bases and the remaining sequence bit is added to the sequence reconstruction. As mismatches are most likely to occur at the end of hybridizing oligos, according to the temporal binding characteristics one or more bases are trimmed from the end in some embodiments. A determination as to which base is trimmed is informed by information from other oligos tiling over the same sequence space, in some embodiments.

In some embodiments, a signal that does not appear to be reversible is weighed against because it has a chance or degree of likelihood of corresponding to a non-specific signal (e.g., due to attachment of fluorescent contaminant to the surface).

Blocks 302-304.

Another method of sequencing a nucleic acid is provided that includes fixing the nucleic acid in a linearized stretched form on a test substrate, thereby forming a fixed stretched nucleic acid. The nucleic acid is affixed to the substrate according to any one of the methods described above.

Isolating Single Cells on a Surface and Extracting Both DNA and RNA.

Either or both RNA and DNA can be isolated from a single cell and sequenced. In some embodiments, when the goal is to sequence DNA, RNAse is applied to the sample before sequencing commences. In some embodiments, when the aim is to sequence RNA, DNAse is applied to the sample before sequencing commences. In some embodiments, where both cytoplasmic nucleic acids and nuclear nucleic acids are to be analyzed, they are extracted differentially or sequentially. In some embodiments, first the cell membrane (and not the nuclear membrane) is disrupted to release and collect the cytoplasmic nucleic acids. Then the nuclear membrane is disrupted to release the nuclear nucleic acids. In some embodiments, proteins and polypeptides are collected as part of the cytoplasmic fraction. In some embodiments, RNA is collected as part of the cytoplasmic fraction. In some embodiments, DNA is collected as part of the nuclear fraction. In some embodiments, the cytoplasmic and nuclear fractions are extracted together. In some embodiments, after extraction the mRNA and genomic DNA are differentially captured. For example, the mRNA is captured by oligo dT probes attached to the surface. This can occur in a first part of a flow cell and the DNA is captured in a second part of a flow cell that has a hydrophobic vinylsilane coating on which the ends of the DNA can be captured (e.g., presumably due to hydrophobic interactions).

Surfaces with positive charges such as poly(L)lysine (PLL) (e.g., as available from Microsurfaces Inc. or coated in house) are known to be able to bind to cell membranes. In some embodiments, a low height of flow channel (e.g., <30 microns) is used so that there is increased chance for the cells to collide with the surface. The number of collisions is increased in some embodiments by using a herringbone pattern in the flow cell ceiling to introduce turbulent flow. In some embodiments, the cell attachment does not need to be efficient as it is desirable for cells to be dispersed at low density onto the surface in such embodiments (e.g., to ensure that there is sufficient space between cells so that the RNA and DNA extracted from each individual cell will remain spatially separated). In some embodiments, the cells are burst using proteinase treatment so that both the cell and nuclear membrane are disrupted (e.g., so that the cellular contents are released into the medium and are captured at the surface in the vicinity of the isolated cell). Once immobilized, the DNA and RNA is stretched in some embodiments. In some embodiments, the stretching buffer is flowed unidirectionally across the coverglass surface (e.g., causing the DNA and RNA polynucleotides to stretch out and align in the direction of fluid flow). In some embodiments, modulations of the conditions (e.g., such as temperature, composition of the stretching buffer and the physical force of the flow) cause most of the RNA secondary/tertiary structure to denature so that RNA is available for binding to antibodies. Once the RNA is stretched, in a denatured form it is possible to switch from denaturation buffer to binding buffer.

Alternatively, the RNA is extracted and immobilized first by disrupting the cell membrane and inducing flow in one direction. The nuclear membrane is disrupted next by using proteinase and flow is induced in the opposite direction. In some embodiments, the DNA is fragmented before or after release, by using rare-cutting restriction enzymes for example, (e.g., NOT1, PMME1). This fragmentation aids in disentangling DNA and allows individual strands to be isolated and combed. It is ensured that the system is set-up so that the immobilized cells are far enough apart that the RNA and DNA extracted from each cell do not co-mingle. In some embodiments, this is aided by inducing a liquid to gel transition before, after or during bursting of the cell.

In some embodiments, the nucleic acid is double-stranded nucleic acid. In such embodiments, the method further comprises denaturing the fixed double-stranded nucleic acid to single stranded form on the test substrate. The nucleic acid must be in a single stranded form for sequencing to proceed. Once the fixed double-stranded nucleic acid has been denatured, both a fixed first strand and a fixed second strand of the nucleic acid are obtained. The fixed second strand is complementary to the fixed first strand.

In some embodiments, the nucleic acid is single stranded (e.g., mRNA, lncRNA microRNA). In some embodiments where the nucleic acid is single stranded RNA, no denaturing is required before the sequencing method proceeds.

In some embodiments, the sample comprises a single-stranded polynucleotide without a native complementary strand in close proximity. In some embodiments where the binding locations for each of the oligos of the repertoire along the polynucleotide are compiled, the sequence is reconstructed by aggregating all the sequence bits according to their location and stitching them together.

Stretching RNA.

The stretching of nucleic acids on a charged surface is affected by the solution cationic concentration. At low salt concentrations, RNA which is single stranded and bears negative charges along its backbone will bind to the surface randomly along its length.

There are multiple possible methods to denature and stretch RNA into a linear form. In some embodiments, the RNA is initially encouraged to enter a globular form (e.g., by using high salt concentrations). In some such embodiments, the ends of each RNA molecule (e.g., in particular, the poly A tail) become more accessible to interaction. Once the RNA has been bound in a globular form, a different buffer (e.g., a denaturing buffer) is applied into the flow cell in some embodiments.

In alternative embodiments, the surface is pre-coated with oligo d(T) to capture the poly A tails of mRNA (e.g., as described by Ozsolak et al., Cell 143:1018-1029, 2010). PolyA tails are typically regions that should be relatively free from secondary structure (e.g., as they are homopolymers). As poly A tails are relatively long (250-3000 nucleotides) in higher eukaryotes, in some embodiments, long oligo d(T) capture probes are designed so that hybridization is performed at a relatively high stringency (e.g., high temperature and/or salt conditions), sufficient to melt a significant fraction of intramolecular base pairing in the RNA. After binding, in some embodiments, transitioning the rest of the RNA structure from a globular to a linear state is done by using denaturing conditions that are not sufficient to abrogate the capture but disrupt intramolecular base-pairing in the RNA and by fluid flow or electrophoretic forces.

Block 310.

In some embodiments, the fixed stretched nucleic acid is exposed to a respective pool of a respective oligonucleotide probe in a set of oligonucleotide probes. Each oligonucleotide probe in the set of oligonucleotide probes is of a predetermined sequence and length, the exposing occurring under conditions that allow for individual probes of the respective pool of the respective oligonucleotide probe to transiently and reversibly to each portion of the fixed nucleic acid that is complementary to the respective oligonucleotide probe thereby giving rise to a respective instance of optical activity.

Block 312.

In some embodiments, a location on the test substrate and a duration of each respective instance of optical activity occurring during the exposing using a two-dimensional imager is measured.

Block 314.

In some embodiments, the exposing and measuring are repeated for respective oligonucleotide probes in the set of oligonucleotide probes, thereby obtaining a plurality of sets of positions on the test substrate, each respective set of positions on the test substrate corresponding to an oligonucleotide probe in the set of oligonucleotide probes.

Block 316.

In some embodiments, the sequence of at least a portion of the nucleic acid is determined from the plurality of sets of positions on the test substrate by compiling the positions on the test substrate represented by the plurality of sets of positions.

RNA Sequencing.

The lengths of RNA are typically shorter than genomic DNA but it is challenging to sequence RNA from one end to the other using current technologies. Nevertheless, because of alternative splicing it is vitally important to determine the full sequence organization of the mRNA. In some embodiments, mRNA is captured by binding of its Poly A tail by immobilized oligo d(T) and its secondary structure is removed by the stretching force applied (e.g. >400 pN) and denaturation conditions (e.g., comprising Formamide and or 7 M or 8 M Urea) so that it is elongated on the surface. This then allows binding reagents (e.g., exon-specific) to be transiently bound. Because of the short length of RNA, it is beneficial to employ the single molecule localization methods described in the present disclosure to resolve and differentiate exons. In some embodiments, just a few binding events scattered across the RNA is sufficient to determine the order and identity of exons in the mRNA for a particular mRNA isoform.

Double-Strand Consensus

A method for obtaining sequence information from a sample molecule follows:
i) Provide a first oligo with first color label. Provide a second oligo with a second color label where the second oligo is complementary in sequence to the first oligo
ii) Elongating, fixing and denaturing double-stranded nucleic acid molecules on a substrate
iii) Exposing both first and second oligo to the denatured nucleic acid of ii.
iv) Determining locations of binding of first and second oligo
v) Where the positions of binding co-localise, the locations are deemed as correct
vi) Multiple locations along the elongated nucleic acid are bound.

In some embodiments, the oligos bind transiently and reversibly. In some embodiment the first and second oligos are part of compete repertoire of first and second oligos of a given length and steps ii-iii are repeated for each first and second oligo pair of the repertoire to sequence the entire nucleic acid.

In some embodiments, a number of corrections need to be made to ensure that the two colors optically co-localize when they should. This includes correcting for chromic aberrations. In some such embodiments, the two oligos of the pair are added together but to prevent them from annealing to each other and thus their action being neutralized, modified oligonucleotide chemistry is used with non-self-pairing analogue bases where modified G cannot pair with modified C in the complementary oligonucleotides but can pair with unmodified C on the target nucleic acid, and modified A cannot pair with modified T in the complementary oligonucleotides but can pair with unmodified T etc. Thus in such embodiments the first and second oligo are modified such that the first oligo cannot form base pairs with the second oligo.

In some embodiments, the first and second oligos are not added together but one is added after the other.

In such embodiments, wherein one oligo is added after another, wash steps are conducted in between; in this case the two oligos of the complementary pair are abeled with the same color and there is no need to correct for chromic aberrations. Also, there is no possibility of the two oligos binding with each other.

In some embodiments, the nucleic acid is exposed to further first and second oligos until the entire repertoire of oligos has been exhausted.

In some embodiments, the second oligo is added as the next oligo after the first oligo, before other oligo pairs of the repertoire are added. In some embodiments the second oligo is not added as the next oligo before other oligo pairs of the repertoire are added.

An example of such an embodiment comprises a method for obtaining sequence information from a sample molecule follows:
i) Elongating, fixing and denaturing double-stranded nucleic acid molecules on a substrate
ii) Exposing a first labeled oligo to the denatured nucleic acid of i) and detecting and recording its location of binding
iii) Removing the first labeled oligo by washing
iv) Exposing a second labeled oligo to the denatured nucleic acid of i) and detecting and recording its location of binding
v) Optionally correcting for drift between the recordings in ii) and iv)
vi) Where the recorded positions of binding obtained in ii-iv co-localize, the sequence information thus obtained about the sequence of the location is deemed as correct In some embodiments, the first and second oligos are part of compete repertoire of first and second oligos of a given length and steps ii-iii are repeated for each first and second oligo pair of the repertoire to sequence the entire nucleic acid.

The co-localization tells us we are looking at the same sequence loci. Further, the probe targeting the sense strand could be looking to discriminate a central base using 4 differentially labeled oligos and the probe targeting the antisense strand could be looking to discriminate a central base using 4 differentially label oligos with complementary sequence to the probes for the sense strand. To obtain a validated base call for the central position, the data for the sense strand should corroborate the data for the second strand. So if the oligo with central A base binds to the sense strand, the oligo with central T base should bind to the antisense strand.

Obtaining such corroboration or consensus for the sense and antisense strand also helps to overcome the ambiguity due to binding due to a G:T or G:U wobble base pairing. Where this occurs on the sense strand, it is unlikely to yield signal on the antisense strand because C:A is less likely to form a base-pair.

In some embodiments, a modified G base or T/U can be used in the probe to prevent formation of the wobble base-pair. In some other embodiments the reconstruction algorithm takes account of the possibility of the formation of a wobble base-pair, especially when corroboration with a C:G base-pair is absent on the complementary strand and the location correlates with an oligo binding to the complementary strand that forms an A:T base pair. In some embodiments, 7-deazaguanisine with the ability to form only two hydrogen bonds rather than 3 is used as a G modification to reduce the stability of base pairs it forms and the occurrence of G-quadraplex and its (and hence its promiscuous binding).

Concurrent Duplex Consensus Assembly.

In some embodiments, both strands of a double helix are present and are exposed to oligonucleotides as described above while in close proximity. In some embodiments, it is not possible to distinguish, from the transient optical signals that are detected, which of the two complementary strands each oligo in a respective oligonucleotide set has bound. For example, when the binding locations along each polynucleotide for each of the oligos of the respective oligonucleotide set along the polynucleotide are compiled, it may appear as though two probes of different sequences have bound to the same location. These oligos should be complementary in sequence, and the difficulty then becomes determining which strand each of the two oligos bound, which is a prerequisite for accurately compiling a sequence for the polynucleotide.

To determine whether a single binding event is to one or the other strand, the complete set of obtained optical activity data must be considered. For example, if two tiling series of oligos cover the locality in question, which of two tiling series the signal belongs to will be assigned based on which series the oligo sequence generating the signal overlaps with. In some embodiments, the sequence is then reconstructed by first using location of binding and sequence overlap to construct each of the two tiling series. Then the two tiling series are aligned as reverse complements and the base assignment at each location is accepted only if the two strands are perfect reverse complements at each of those locations (e.g., thus providing duplex consensus sequence).

In some embodiments, a sequencing mismatch is flagged as being an ambiguous base call where one of the two possibilities needs to be corroborated by additional layers of information, such as that from independent mismatch binding events. In some embodiments, once the duplex consensus has been obtained, a conventional (multi-molecule) consensus is determined by comparing data from other polynucleotides that cover the same region of the genome (e.g., when binding site information from multiple cells are available). One issue with such an approach is the possibility of the polynucleotides containing haplotype sequences.

Alternatively, in some embodiments, individual strand consensus is obtained before the duplex consensus of the individual strand consensus is obtained. In such embodiments, the sequence of each of the strands of the duplex is obtained concurrently. This is done in some embodiments without requiring additional sample preparation steps, such differentially tagging the two strand of a duplex with molecular barcodes, unlike current NGS methods (e.g., as described by Salk et al., Proc. Natl. Acad. Sci. 109(36), 2012).

Simultaneous sequence acquisition of both sense and antisense strands compares favorably with 2D or $1D^2$ consensus sequencing that is available for nanopores. These alternate methods require sequence to be obtained for one strand of the duplex before the sequence of the second strand is obtained. In some embodiments, duplex consensus sequencing provides accuracy in the $10^6$ range e.g. one error in a million bases (compared to the $10^2$-$10^3$ raw accuracy of other NGS approaches). This makes the method highly compatible with the need to resolve rare variants that indicate a cancer condition (e.g., such as those present in cell-free DNA) or that are present at low frequency in a tumor cell population.

Single-Cell Resolved Sequencing.

In various embodiments, the method further comprises sequencing the genome of a single cell. In some embodiments, the single cells are free from attachment from other cells. In some embodiments, the single cells are attached to other cells in clusters or in tissue. In some embodiments, such cells are disaggregated into individual non-attached cells.

In some embodiments, the cells are disaggregated before they are fluidically transferred (e.g., by using a pipette) to the inlet of the structure (e.g., flow cell, or microwell) in which the polynucleotides are elongated. In some embodiments, disaggregation is done by pipetting the cells, by applying proteases, sonication or physical agitation. In some embodiments, the cells are disaggregated after they are fluidically transferred into the structure where they elongated.

In some embodiments, the single cell is isolated and the polynucleotide is released from single cell, such that all the polynucleotides originating from the same cell remain disposed close to one another and at a location that is distinct from the locations where the contents of other cells are disposed. In some embodiments, the trap structures are as described by Di Carlo et al., Lab Chip 6:1445-1449, 2006 are used.

In some embodiments, it is possible to use a microfluidic architecture that either captures and isolates multiple single cells (e.g., in a case where the traps are separate, such as that shown in FIGS. 16A and 16B) or an architecture that captures multiple non-isolated cells (e.g., in a case where the trap is continuous). In some embodiments, the traps are the dimension of single cells (e.g., from 2 µM-10 µM. In some embodiments, the flow cell is several hundreds of microns to millimeters in length, with a depth of ~30 microns.

Figure 17:
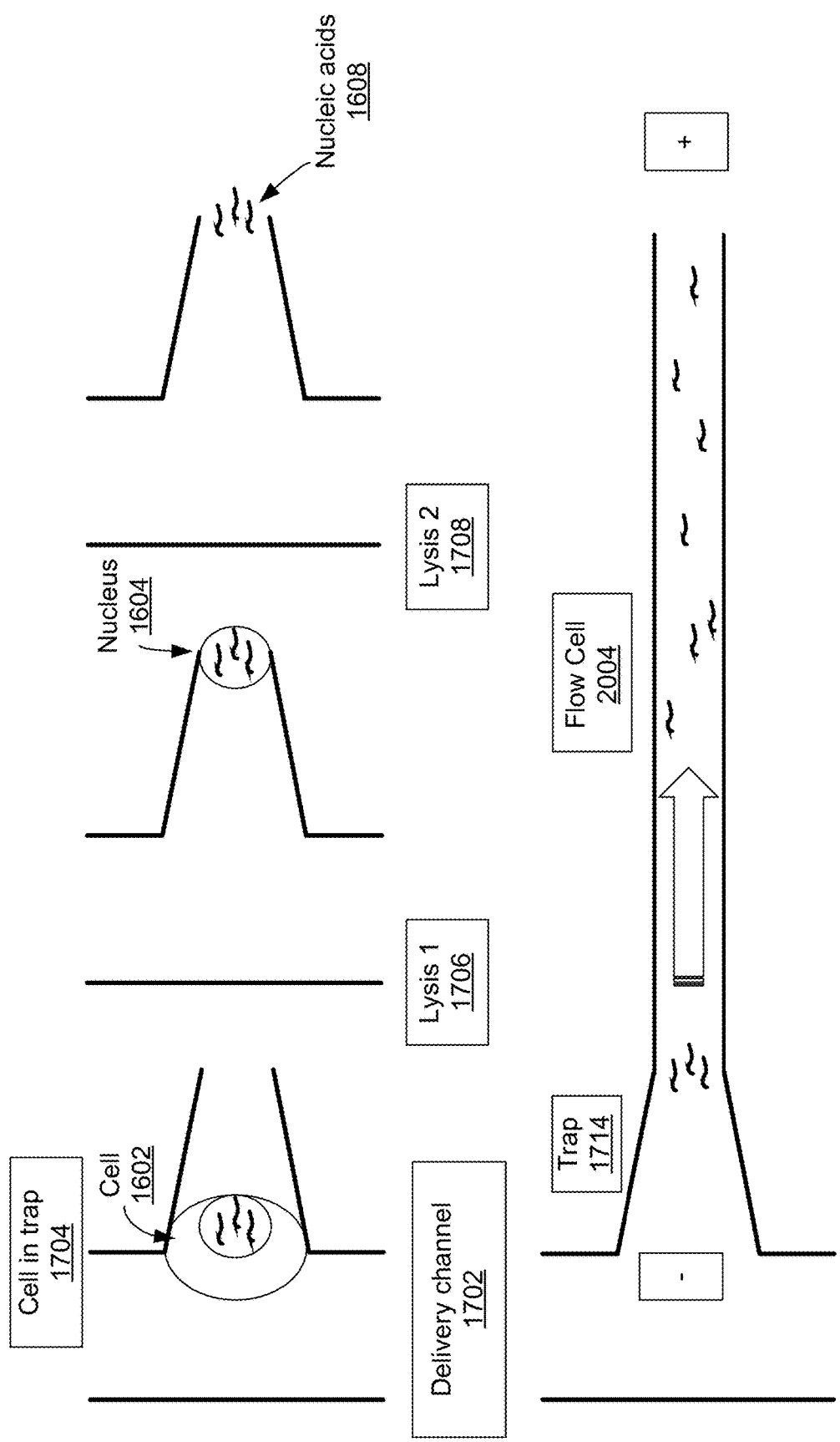
FIG. 17 illustrates an example microfluidic architecture which captures a single cell and optionally provides for extraction, elongation, and sequencing of the nucleic acids from the cell in accordance with various embodiments of the present disclosure.
Figure 18:
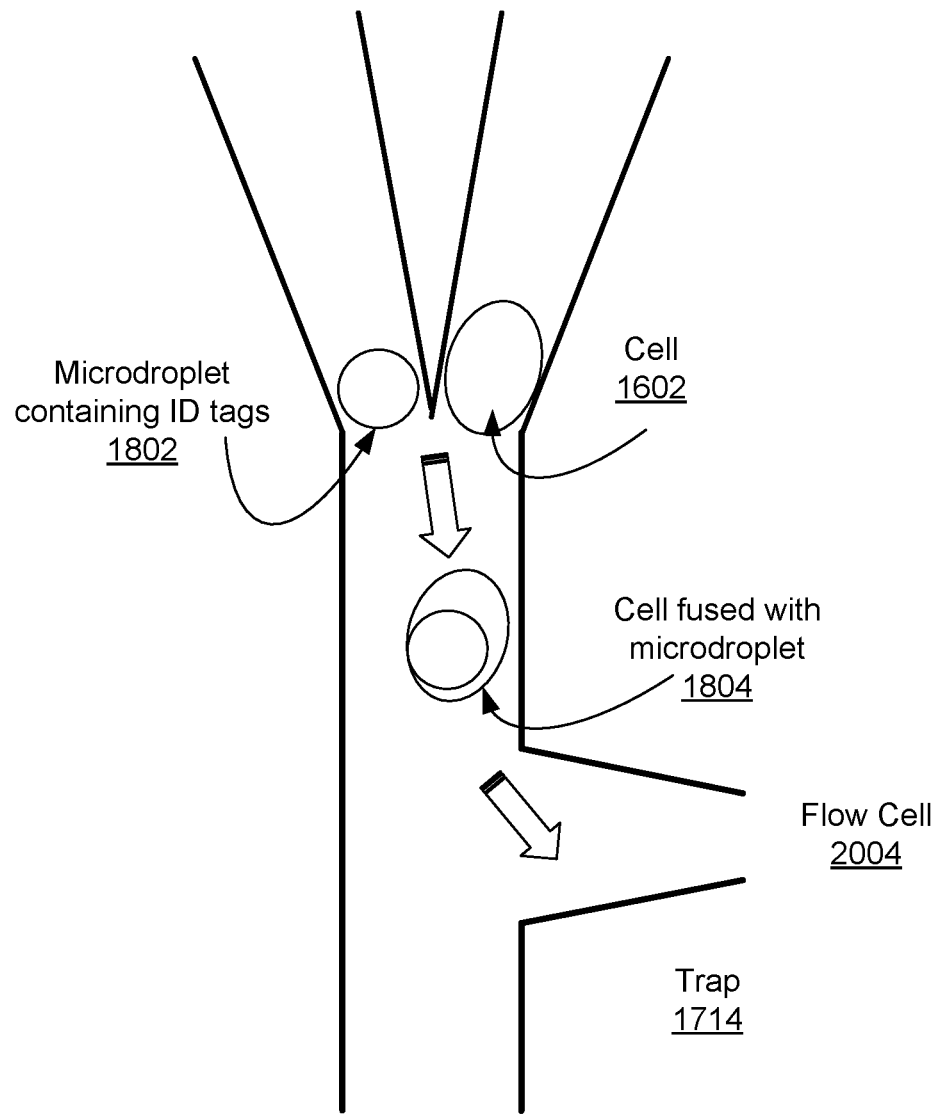
FIG. 18 illustrates an example microfluidic architecture that provides distinct ID tags to individual cells in accordance with various embodiments of the present disclosure.

In some embodiments, for example as shown in FIG. 17, the single cell is flowed into a delivery channel 1702, trapped 1704, and the nucleotides are released and then elongated. In some embodiments, the cell 1602 is lysed 1706, and then the cell nucleus is lysed through a second lysis step 1708, thus releasing the extracellular and intracellular polynucleotides 1608 sequentially. Optionally, both extra nuclear and intranuclear polynucleotides are released using a single lysis step. After release, the polynucleotides 1608 are immobilized along the length of a flow cell 2004 and elongated. In some embodiments, the traps are the dimension of single cells (e.g. 2 µM-10 µM wide). In one embodiment, the trap dimensions are 4.3 µM-wide at the bottom, 6 µm at middle depth and 8 µm at the top with a depth of 33 µm and the device is made from cyclic olefin (COC) using injection molding.

In some embodiments, the single cell is lysed into an individual channel and each individual cell is reacted with a unique tag sequence via transposase mediated integration, before the polynucleotides are combined and sequenced in the same mixture. In some embodiments, the transposase complex is transfected into cells or is in a droplet merged into a droplet containing the cells.

In some embodiments, the aggregates are small clusters of cells and in some embodiments, the entire cluster is tagged with the same sequencing tag. In some embodiments, the cells are not aggregating and are free floating cells such as circulating tumor cells (CTCs) or circulating fetal cells.

In single cell sequencing there is a problem of cytosine-to-thymine single nucleotide variants caused by spontaneous cytosine deamination after cell lysis. This is overcome by pretreating samples with uracil N-glycosylase (UNG) prior to sequencing (e.g., as described by Chen et al., Mol Diagn Ther. 18(5): 587-593, 2014)

Identifying Haplotypes.

In various embodiments, the methods described above are used for sequencing haplotypes. Sequencing haplotypes includes sequencing a first target polynucleotide spanning a haplotype of a diploid genome using the methods described herein. A second target polynucleotide that spans a second haplotype region of the diploid genome must also be sequenced. The first and second target polynucleotides will be from different copies of a homologous chromosome. The sequences of the first and second target polynucleotides are compared, thereby determining the haplotypes on the first and second target polynucleotides.

Hence, single molecule reads and assemblies that are obtained from the embodiments, are classed as being haplotype-specific. The only case where haplotype-specific information is not necessarily easily obtained over a long range is when assembly is intermittent. In such embodiments, the location of the reads is provided nonetheless. Even in such a situation, if multiple polynucleotides are analysed that cover the same segment of the genome, the haplotype is determined computationally.

In some embodiments, homologous molecules are separated, according to haplotype or parental chromosome specificity. The visual nature of the information obtained by the methods of the present disclosure, actually physically or visually, is capable of showing a particular haplotype. In some embodiments, the resolution of haplotypes enables improved genetic or ancestry studies to be conducted. In other embodiments, the resolution of haplotypes enables better tissue typing to be done. In some embodiments, the resolution of haplotypes or the detection of a particular haplotype enables a diagnosis to be made.

Sequencing Polynucleotides from Multiple Cells Concurrently.

In various embodiments, the methods described above are used to sequence polynucleotides from a plurality of cells (or nuclei) where each polynucleotide retains information of its cell of origin.

In certain embodiments, transposon mediated sequence insertion is mediated inside the cell, and each insertion comprises a unique ID sequence tag as a label for the cell of origin. In other embodiments, the transposon mediated insertion occurs inside a container in which a single cell has been isolated, such containers comprising, agarose beads, oil-water droplets etc. The unique tag indicates that all the polynucleotides bearing the tag must originate from the same cell. All of the genomic DNA and or RNA is then extracted, allowed to mix, and elongated. Then when sequencing according to the embodiments of the invention (or any other sequencing method) is conducted on a polynucleotide, the reading of the ID sequence tag indicates which cell the polynucleotide originates from. It is preferable to keep the cell identifying tag short. For 10,000 cells (e.g., from a tumor microbiopsy), ~65,000 unique sequences are provided by an identifier sequence of eight nucleotides in length and around a million unique sequences are provided by an identifier sequence of ten nucleotides in length.

Figure 19:
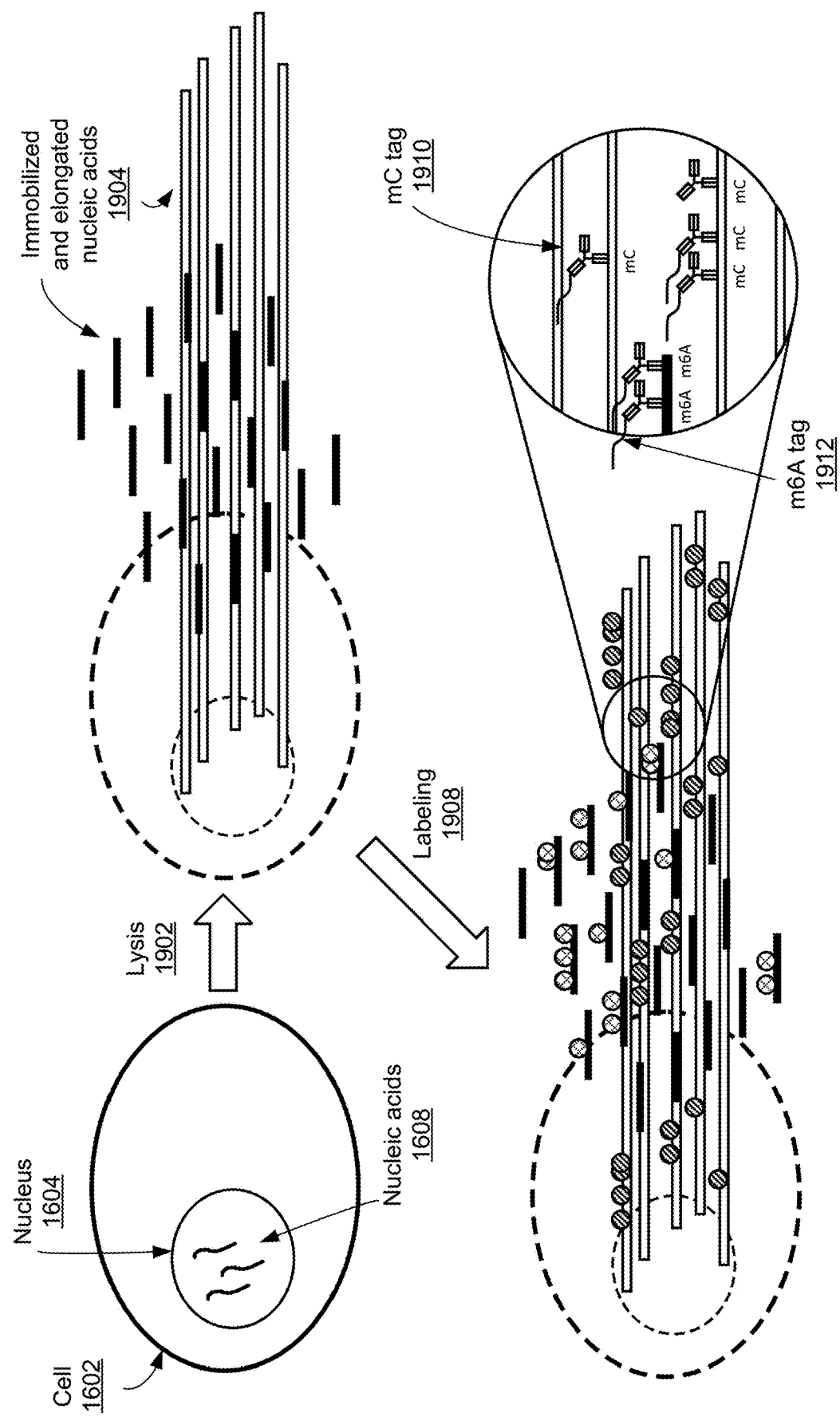
FIG. 19 illustrates an example of sequencing polynucleotides from an individual cell in accordance with various embodiments of the present disclosure.

In some embodiments, individual cells are tagged with identity (ID) tags. As shown in FIG. 19, in some embodiments the identity tags integrate into the polynucleotides by tagmentation, for which reagents are provided directly to the single cell or in a microdroplet that merges with or engulfs the cell 1802. Each cell receives a different ID tag (from a large repertoire e.g., greater than a million possible tags). After the microdroplet and the cell have fused 1804, the ID tags are integrated into the polynucleotides within individual cells. The contents of the individual cells are mixed within the flow cell 2004. Sequencing (e.g., by methods disclosed herein) then reveals which cell a particular polynucleotide originates from. In alternative embodiments, the microdroplet engulfs the cell and delivers the tagging reagents to the cell (e.g., by diffusing into the cell or bursting the cell contents into the microdroplet).

This same indexing principle is applied to samples other than cells (e.g., from different individuals) when the aim is to mix the samples, sequence them together, but to recover the sequence information pertaining to each individual sample.

Further, when multiple cells are sequenced, it is possible to determine the haplotype diversity and frequency in the cell population. In some embodiments, the heterogeneity of genomes in a population is analyzed without the need to keep the content of single cells together because, if molecules are long enough, the different chromosomes, long chromosomes segments or haplotypes that are present in the population of cells is determined. Although this does not indicate which two haplotypes are present in a cell together, it does report on the diversity of genomic structural types (or haplotypes) and their frequency and which aberrant structural variants are present.

In some embodiments, when the polynucleotide is RNA and a cDNA copy is sequenced, addition of the tag comprises cDNA synthesis with a primer containing the tag sequence. Where RNA is sequenced directly, a tag is added y ligation of the tag to the 3' RNA termini using T4 RNA Ligase. An alternative method of generating the tag is to extend the RNA or DNA with terminal transferase with more than one nucleotide of the four A, C, G and T bases, so that each individual polynucleotide, stochastically, gets a unique sequence of nucleotides tailed thereon.

In some embodiments, in order to keep the amount of sequence to be kept short, so that more of the sequence read is devoted to sequencing the polynucleotide sequence itself, the tag sequence is distributed over a number of sites. Here multiple short identifier sequences, say three, are introduced into each cell or container. Then the origin of the polynucleotide is determined from the bits of the tag that are distributed along the polynucleotide. So in this case the bit of the tag read from one location is not sufficient to determine the cell of origin, but multiple tag bits are sufficient to make the determination.

Detection of Structural Variants.

In some embodiments, the differences between the detected sequence and the reference genome comprise substitutions, indels and structural variations. In particular, when the reference sequence has not been assembled by the methods of the present disclosure, the repeats are compressed, and the reconstruction will decompress.

In some embodiments, the orientation of a series of sequence reads along the polynucleotide will report on whether an inversion event has occurred. One or more reads in the opposite orientation to other reads compared to the reference, indicates an inversion.

In some embodiments, the presence of one or more reads that is not expected in the context of other reads in its vicinity indicates a rearrangement or translocation compared to reference. The location of the read in the reference indicates which part of the genome has shifted to another. In some cases, the read in its new location is a duplication rather than a translocation.

In some embodiments, it is also possible to detect repetitive regions or copy number variations. The repeated occurrence of a read or related read carrying paralogous variation is observed as multiple or very similar reads occurring at multiple locations in the genome. These multiple locations are packed close together in some instances (e.g., as in satellite DNA) or they are dispersed across the genome in other cases (e.g., as in pseudogenes). The methods of the present disclosure are applied to the Short Tandem Repeats (STRS), variable number of tandem repeats (VNTR), trinucleotide repeats, etc. The absence or repetition of specific reads indicates that a deletion or amplification, respectively has occurred. In some embodiments, the methods are particularly applied in cases where there are multiple and/or complex rearrangements in a polynucleotide. Because the methods are based on analysing single polynucleotides, in some embodiments, the structural variants described above are resolved down to a rare occurrence in small numbers of cells for example, just 1% of cells from a population.

Similarly, in some embodiments, segmental duplications or duplicons are correctly localized in the genome. Segmental duplicons are typically long regions in a DNA sequence (e.g., greater than 1 kilobase in length) of nearly identical sequence. These segmental duplications cause a lot of the structural variation in individual genomes, including somatic mutations. Segmental duplicons may exist in distal parts of the genome. In current next generation sequencing, it is difficult to determine which segmental duplicon a read arises from (thus complicating assembly). In some embodiments of the present disclosure, sequence reads are obtained over long molecules (e.g., 0.1-10 Megabase length range), and it is usually possible to determine the genomic context of a duplicon by using the reads to determine which segments of the genome are flanking the particular segment of the genome corresponding to the duplicon.

Breakpoints of structural variants are localized precisely in some embodiments of the present disclosure. In some embodiments, it is possible to detect that two parts of the genome have fused, and the precise individual read at which the breakpoint has occurred is determined. Sequence reads, collected as described herein, comprise a chimera of the two fused regions, all the sequences on one side of the breakpoint will correspond to one of the fused segments and the other side is the other of the fused segments. This gives high confidence in determining a breakpoint, even in cases where the structure is complex around breakpoint. In some embodiments, the precise chromosomal breakpoint information is used in understanding a disease mechanism, in detecting the occurrence of a specific translocation, or in diagnosing a disease.

Localization of Epigenomic Modifications.

In some embodiments, the method further comprises exposing the fixed double strand or fixed first strand and the fixed second strand to an antibody, affimer, nanobody, aptamer, or methyl-binding protein to thereby determine a modification to the nucleic acid or to correlate with the sequence of the portion of the nucleic acid from the plurality of sets of positions on the test substrate. Some antibodies bind to double strand or single strand. Methyl binding proteins would be expected to bind double stranded polynucleotides.

In some embodiments, the native polynucleotides require no processing before they are displayed for sequencing. This allows the method to integrate epigenomic information with sequence information, as the chemical modifications of DNA will stay in place. Preferably the polynucleotides are directionally well aligned and therefore relatively easy to image, image process, base call and assemble; the sequence error rate is low and coverage is high. A number of embodiments for carrying out the present disclosure are described but each is done so that the burden of sample preparation is wholly or almost wholly eliminated.

Because these methods are performed on genomic DNA without amplification, in some embodiments, they do not suffer from amplification bias and error, and epigenomic marks are preserved and are detected (e.g., orthogonally to the acquisition of sequence). In some cases, it is useful to determine in a sequence-specific manner if the nucleic acid is methylated. For example, one way of differentiating fetal from maternal DNA is the former is methylated in loci of interest. This is useful for non-invasive prenatal testing (NIPT).

Multiple types of methylation are possible, such as alkylation of carbon-5 (C5), which yields several cytosine variants in mammals, C5-methylcytosine (5-mC), C5-hydroxymethylcytosine (5-hmC), C5-formylcytosine, and C5-carboxylcytosine. Eukaryotic and prokaryotic organisms also methylate adenine to N6-methyladenine (6-mA). In prokaryotes, N4-methylcytosine is also prevalent.

Antibodies are available or are raised against each of these modifications as well as any others that are construed as of interest. Affimers, Nanobodies or Aptamers that target the modifications are particularly relevant due to the possibility of a smaller footprint. Any reference to antibody in this invention should be construed as including Affimers, Nanobodies, Aptamers and any similar reagents. In addition, other, naturally occurring DNA binding proteins, e.g., methyl proteins (MBD1, MBD2, etc.) are used in some embodiments.

Methylation analysis is carried out orthogonally to the sequencing in some embodiments. In some embodiments, this is done before sequencing. As an example, anti-methyl C antibodies or methyl binding proteins (Methyl binding domain (MBD) protein family comprise MeCP2, MBD1, MBD2 and MBD4) or peptides (based on MBD1) are bound to the polynucleotides in some embodiments, and their location detected via labels before they are removed (e.g., by adding high salt buffer, chaotrophic reagents, SDS, protease, urea and/or Heparin). Preferably the reagents bind transiently, due to use of a transient binding buffer that promotes on-off binding or the reagents are engineered to bind transiently. Similar approaches are used for other polynucleotide modifications, such as hydroxymethylation or sites of DNA damage, for which antibodies are available or are raised. After the locations of the modifications have been detected and the modification binding reagents are removed, sequencing commences. In some embodiments, the anti-methyl and anti-hydroxymethyl antibodies etc. are added after the target polynucleotide is denatured to be single stranded. The method is highly sensitive and is capable of detecting a single modification on a long polynucleotide.

FIG. 19 illustrates the extraction and stretching of DNA and RNA from a single cell and differential labeling of DNA and RNA (e.g., with antibodies to mC and m6A, respectively). The cell 1602 is immobilized on a surface and then lysed 1902. The nucleic acids 1608, which are released from the nucleus 1604 by the lysis, are immobilized and elongated 1904. The nucleic acids are then exposed to and bound by antibodies with appended DNA tags 1910 and 1912. In some embodiments, the tags are fluorescent dyes or oligonucleotide docking sequences for DNA PAINT-based single molecule localization. In some embodiments, instead of using tags and DNA PAINT, the antibodies or other binding proteins are directly fluorescently labelled, either with a single fluorescent label or multiple fluorescent labels. In the case where the antibodies are encoded, one example of the labelling is as shown in FIGS. 14A, 14C and 14D. The epi-modification analysis of both DNA and RNA is coupled with their sequence using the sequencing methods described herein in some embodiments.

In some embodiments, in addition to detecting methylation by binding proteins, the presence of methylation in a binding site is detected by the differential oligonucleotide binding behavior when a modification is present in the target nucleic acid site compared to when it is not.

In some embodiments, bisulfite treatment is used to detect methylation. Here, after running through the repertoire, bisulfite treatment is used to convert unmethylated cytosine to uracil and then the repertoire is applied again. When a nucleotide position that before bisulfite treatment is read as a C, is read as a U after bisulfite treatment it can be deemed to be unmethylated.

There are no reference epigenomes for DNA modifications such as methylations. In order to be useful, the methylation map of an unknown polynucleotide needs to be linked to a sequence based map. Thus the epi-mapping methods are correlated to sequence bits obtained by oligo binding, in order to provide context to the epi-map, in some embodiments. In addition to sequence reads, other kinds of methylation information are also coupled in some embodiments. This includes, as non-limiting examples, nicking endonuclease based maps, oligo-binding based maps and denaturation and denaturation-renaturation maps. In some embodiments, transient binding of one or more oligos is used to map the polynucleotides. In addition to functional modifications to the genome, the same approach is applied to other features that map on to the genome, in some embodiments, such as sites of DNA damage and protein or ligand binding.

In the present disclosure, either the base sequencing or the epigenomic sequencing is performed first. In some embodiments, both are done at the same time. For example, antibodies against specific epi-modification are differentially coded from oligos in some embodiments. In such embodiment, conditions are used (e.g., low salt concentrations) that facilitate transitory binding of both types of probes.

In some embodiments, when the polynucleotide comprises chromosome or chromatin, antibodies are used on chromosomes or chromatin to detect modifications on DNA and also modifications on histones (e.g., histone acetylation and methylation). The location of these modifications is determined by the transient binding of the antibodies to locations on the chromosome or chromatin. In some embodiments, the antibodies are labeled with oligo tags and do not bind transiently but rather are fixed permanently or semi-permanently to their binding site. In such embodiments, the antibody will include an oligo tag, and the locations of these antibody binding sites are detected by using transient binding of complementary oligos to oligos on the antibody tags.

Isolation and Analysis of Cell-Free Nucleic Acid.

Some of the most accessible DNA or RNA for diagnostics is found outside of cells in body fluids or stool. Such nucleic acids have often been shed by cells in the body. Cell-free DNA circulating in blood is used for pre-natal testing for trisomy 21 and other chromosomal and genomic disorders. It is also a means to detect tumor-derived DNA and other DNA or RNA that are markers for certain pathological conditions. However, the molecules are typically present in small segments (e.g., in the ~200 base pair length range in blood and even shorter in urine). The copy number of a genomic region are determined by comparison to the number of reads that align to particular regions of the reference compared to other parts of the genome.

In some embodiments, the methods of the present disclosure are applied to the enumeration or analysis of cell free DNA sequences by two approaches. The first involves immobilizing the short nucleic acid before or after denaturation. The transiently binding reagents are used to interrogate the nucleic acid in order to determine the identity of the nucleic acid, its copy number, whether mutations or certain SNP alleles are present, and whether the sequence detected is methylated or bears other modifications (biomarkers).

The second approach involves concatenating the small nucleic acid fragments (e.g., after the cell-free nucleic acid has been isolated from a biological sample. Concatenation enables stretching out the combined nucleic acid. Catenation is done by polishing the ends of the DNA and performing blunt end-ligation. Alternatively, the blood or the cell free DNA is split into two aliquots and one aliquot is tailed with poly A (using Terminal Transferase) and the other aliquot is tailed by poly T.

The resulting concatamers are then subjected to sequencing. The resulting "super" sequence read is then compared to reference to extract individual reads. The individual reads are computationally extracted and then processed in the same manner as other short reads.

In some embodiments, the biological sample comprises stool, a medium that contains a high number of exonucleases that degrade nucleic acids. In such embodiments, high concentrations of chelators of divalent cations (e.g., EDTA), which are needed by exonucleases to function, is employed to keep the DNA sufficiently intact and enable sequencing. In some embodiments, the cell-free nucleic acid is shed from cells via encapsulation in exosomes. Exosomes are isolated by ultracentrifugation or by using spin columns (Qiagen), and the DNA or RNA contained therein is collected and sequenced.

In some embodiments, methylation information is obtained from cell-free nucleic acid, according to methods described above.

Combining Sequencing Technologies.

In some embodiments, the methods described herein are combined with other sequencing techniques. In some embodiments, following sequencing by transient binding, sequencing by a second method is initiated on the same molecules. For example, longer more stable oligonucleotides are bound to initiate sequencing by synthesis. In some embodiments, the methods stop short of being a complete genome sequencing and are used to provide a scaffold for short read sequencing such as that from Illumina. In this case it is advantageous to conduct Illumina library prep by excluding the PCR amplification step to obtain a more even coverage of the genome. One advantage of some of these embodiments, that fold coverage of sequencing required is halved from about 40× to 20× for example. In some embodiments, this is due to the addition of sequencing done by the methods and the locational information that methods provide. In some embodiments, longer more stable oligos, which are optionally optically labelled, can be bound to the target to mark out specific regions of interest in the genome (e.g. the BRCA1 loci) before or concurrently (preferably differently labelled) with the short sequencing oligos through part or whole of the sequencing process.

Machine Learning Methods.

In some embodiments, artificial intelligence or machine learning is used to learn the behavior of the members of the repertoire when tested against polymers (e.g., polynucleotides) of known sequence and/or when the sequence of the polynucleotide is cross-validated with data from another method. In some embodiments, the learning algorithm takes into account the full behavior of a particular probe against one or more polynucleotide targets containing binding sites for the probe in one or more conditions or contexts. As more sequencing is done on the same or different samples, the more robust the knowledge from machine learning becomes. What is learned from machine learning is applied to various other assays, in particularly those involving interactions of oligos with oligos/polynucleotides (e.g., sequencing by hybridization), in addition to the transient binding-based emergent sequencing.

In some embodiments, artificial intelligence or machine learning is trained by providing data of the binding patterns experimentally obtained for binding of a complete repertoire of short oligos (e.g., 3-mer, 4-mer, 5-mer, or 6-mer) to one or more polynucleotides of known sequence. The training data for each oligo comprises, binding locations, duration of binding and the number of binding events over given period. After this training, the machine learning algorithm is applied to a polynucleotide of sequence to be determined and based on its learning can assemble the sequence of the polynucleotide. In some embodiments, the machine learning algorithm is also provided a reference sequence.

In some embodiments, the sequence assembly algorithm comprises both a machine learning element and a non-machine learning element.

In some embodiments, instead of the computer algorithm learning from the experimentally obtained binding patterns, the binding patterns are obtained via simulations. For example, in some embodiments, simulations are done of the transient binding of oligos of the repertoire to the polynucleotide of known sequence. The simulations are based on a model of the behavior of each oligo obtained from experimental or published data. For example, the prediction of binding stability is available according to the nearest neighbor method (e.g., as described in SantaLucia et al., Biochemistry 35, 3555-3562 (1996) and Breslauer et al., Proc. Natl. Acad. Sci. 83: 3746-3750, 1986). In some embodiments, the mismatching behavior is known (e.g., G mismatch binding to A can be as strong or stronger interaction than T to A) or experimentally derived. Further, in some embodiments, the inordinately high binding strength of some short sub-sequence of oligos (e.g., GGA or ACC) are known. In some embodiments, the machine learning algorithm is trained on the simulated data and then used to determine the sequence of an unknown sequence when it is interrogated by a complete repertoire of short oligos.

In some embodiments, the data (location, binding duration, signal intensity, etc.) of oligos of the repertoire or panel are plugged into a machine learning algorithm, that has been trained on one or more preferably (tens, hundreds or thousands) of known sequences. The machine learning algorithm is then applied to a generate a data-set from a sequence in question and the machine learning algorithm generates the sequence of the unknown sequence in question. The training of the algorithm for sequencing of organisms will relatively smaller or less complex genomes (e.g., for bacteria, bacteriophage etc.) should be performed on organisms of that type. For organisms with larger or more complex genomes (e.g., *S. pombe* or humans), particularly those with repetitive DNA regions, the training should be performed on organisms of that type. For long-range assembly of megabase fragments to whole chromosome lengths, the training is performed on similar organisms in some embodiments, so that particular aspects of the genomes are represented during the training. For example, human genomes are diploid and exhibit large sequence regions with segmental duplication. Other genomes of interest, in particular many agriculturally important plant species have highly complex genomes. For example, wheat and other grains have highly polyploid genomes.

In some embodiments, a machine learning based sequence reconstruction approach comprises: (a) providing information on the binding behavior of each oligo in the repertoire gleaned from one or more training data-sets and (b) providing for physical binding each oligo of the repertoire to the polynucleotide whose sequence is to be determined and (c) providing information on binding location, and/or binding duration and/or the number of times binding occurs at each location for each oligo (e.g., persistence of binding repetition).

In some embodiments, the sequence of a particular experiment is first processed by a non-machine learning algorithm. Then the output sequence of the first algorithm is used to train the machine learning algorithm, so that the training occurs on actual experimentally derived sequence of the same exact molecules. In some embodiments, the sequence assembly algorithm comprises a Bayesian approach. In some embodiments, data derived from the methods of the present disclosure are furnished to an algorithm of the type described in WO2010075570 and are optionally combined with other types of genomic or sequencing data.

In some embodiments, the sequence is extracted from the data in a number of ways. At one end of the spectrum of sequence reconstruction methods the localization of a monomer or a string of monomers is so precise (nanometric or sub-nanometric) that the sequence is obtained by just ordering the monomers or strings. At the other end of the spectrum the data is used to rule out various hypotheses about the sequence. For example, one hypothesis is that the sequence corresponds to a known individual genome sequence. The algorithm determines where the data diverges from the individual genome. In another case the hypothesis is that the sequence corresponds to a known genome sequence for a "normal" somatic cell. The algorithm determines where the data from a putative tumor cell diverges from the sequence of the "normal" somatic cell.

In one embodiment of the present disclosure, a training set comprising one or more known target polynucleotide(s) (e.g., lambda phage DNA or a synthetic construct comprising a super sequence comprising complements to each oligo in the repertoire) are used for tested iterative binding of each oligonucleotide from the repertoire. Machine learning algorithms are used in some embodiments to determine the binding and mismatching characteristics of the oligo probes. Thus counter-intuitively, mismatch binding is seen as a way of providing further data that is used to assemble and/or add confidence to the sequence.

Sequencing Instrumentation and Device.

The sequencing methods have common instrumentation requirements. Basically the instrument must be capable of imaging and exchanging reagents. The imaging requirement includes, one or more from the group: objective lens, relay lens, beam-splitter, mirror, filters and a camera or point detector. The camera includes a CCD or array CMOS detector. The point detector includes a Photomultiplier Tube (PMT) or Avalanche Photodiode (APD). In some cases, a high speed camera is used. Other optional aspects are adjusted depending on the format of the method. For example, the illumination source (e.g., lamp, LED or laser), the coupling of the illumination on to the substrate (e.g., a prism, grating, sol-gel, lens, translatable stage or translatable objective), the mechanism for moving the sample in relation to the imager, sample mixing/agitation, temperature control and electrical controls are each independently adjusted for different embodiments disclosed herein.

For the single molecule implementations, the illumination is preferably via the creation of an evanescent wave, via e.g., prism-based total internal reflection, objective-based total internal reflection, grating-based waveguide, hydrogel based waveguide or an evanescent waveguide created by bringing laser light into the edge of the substrate at a suitable angle. In some embodiments, the waveguide includes a core layer and a first cladding layer. The illumination alternatively comprises HILO illumination or a light sheet. In some single molecule instruments, the effects of light scatter are mitigated by using synchronization of pulsed illumination and time-gated detection; here light scattering is gated out. In some embodiments, dark field illumination is used. Some instruments are set up for fluorescence lifetime measurements.

In some embodiments, the instrument also contains means for extraction of the polynucleotide from cells, nuclei, organelles, chromosome etc.

A suitable instrument for most embodiments is the Genome Analyzer IIx from Illumina. This instruments comprises Prism-based TIR, a 20× Dry Objective, a light scrambler, a 532 nm and 660 nm laser, an infrared laser based focusing system, an emission filter wheel, a Photometrix CoolSnap CCD camera, temperature control and a syringe pump-based system for reagent exchange. Modification of this instrument with an alternative camera combination enables better single molecule sequencing in some embodiments. For example, the sensor preferably has low electron noise, <2 e. Also the sensor has a large number of pixels. The syringe-pump based reagent exchange system is replaced by one based on pressure-driven flow in some embodiments. The system is used with a compatible Illumina flow cell or with a custom-flow cell adapted to fit the actual or modified plumbing of the instrument in some embodiments.

Alternatively, a motorized Nikon Ti-E microscope coupled with a laser bed (lasers dependent on choice of labels) or the laser system and light scrambler from the genome analyzer, a EM CCD camera (e.g., Hamamatsu ImageEM) or a scientific CMOS (e.g., Hamamatsu Orca FLASH) and optionally temperature control is used. In some embodiments, a consumer rather than scientific sensor is used. This has the potential to reduce the cost of sequencing dramatically. This is coupled with a pressure driven or syringe pump system and a specifically designed flow cell. In some embodiments, the flow cell is fabricated in glass or plastic, each having advantages and disadvantages. In some embodiments, the flow cell is fabricated using cyclic olefin copolymer (COC), e.g., TOPAS, other plastics, or PDMS or in silicon or glass using microfabrication methods. In some embodiments, injection molding of thermoplastics provides a low-cost router to industrial scale manufacture. In some optical configurations, the thermoplastic needs to have good optical properties with minimal intrinsic fluorescence. Polymers excluding containing aromatic or conjugated systems should ideally be excluded since they are expected to have a significant intrinsic fluorescence. Zeonor 1060R, Topas 5013, and PMMA-VSUVT (e.g., as described in U.S. Pat. No. 8,057,852) have been reported to have reasonable optical properties in the green and red wavelength range (e.g., for Cy3 and Cy5), with Zeonar 1060R having the most favorable properties. In some embodiments, it's possible to bond thermoplastics over a large area in a microfluidic device (e.g., as reported by Sun et al., Microfluidics and Nanofluidics, 19(4), 913-922, 2015). In some embodiments, the glass cover glass onto which the biopolymers are attached is bonded to a thermoplastic fluidic architecture.

Alternatively, a manually operated flow cell is used atop the microscope. This is constructed in some embodiments by making a flow cell using a double-sided sticky sheet, laser cut to have channels of the appropriate dimensions and sandwiched between a coverslip and a glass slide. From one reagent exchange cycle to another the flow cell can remain on the instrument/microscope, to registration from frames to frame. A motorized stage with linear encoders is used to ensure when the stage is translated during imaging of a large area, in some embodiments. The same locations are correctly revisited. Fiduciary markers are used to endure correct registration. In this case, it is preferable to have fiduciary markings such as etchings in the flow cell or surface immobilized beads within the flow cell that are optically detected. If the polynucleotide backbone is stained (for example, by YOYO-1) those fixed, known positions are used to align images from one frame to the next.

In one embodiment, the illumination mechanism (e.g., such as that described in U.S. Pat. No. 7,175,811 and by Ramachandran et al., Scientific Reports 3:2133, 2013) that uses laser or LED illumination is coupled with an optional heating mechanism and reagent exchange system to carry out the methods described herein. In some embodiments, a smartphone based imaging set up (ACS Nano 7:9147) is coupled with an optional temperature control module and a reagent exchange system. In such embodiments, it is principally the camera on the phone that is used, but other aspects such as illumination and vibration capabilities of an iPhone or other smartphone device can also be used.

Figure 20A:
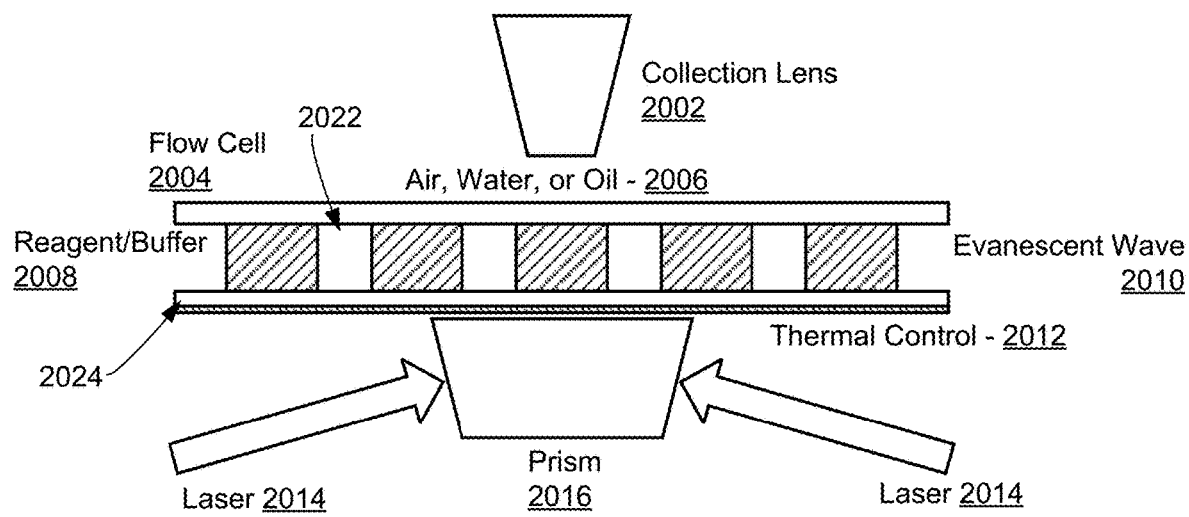
FIGS. 20A and 20B collectively illustrate example device layouts for performing imaging of transient probe binding in accordance with various embodiments of the present disclosure.
Figure 20B:
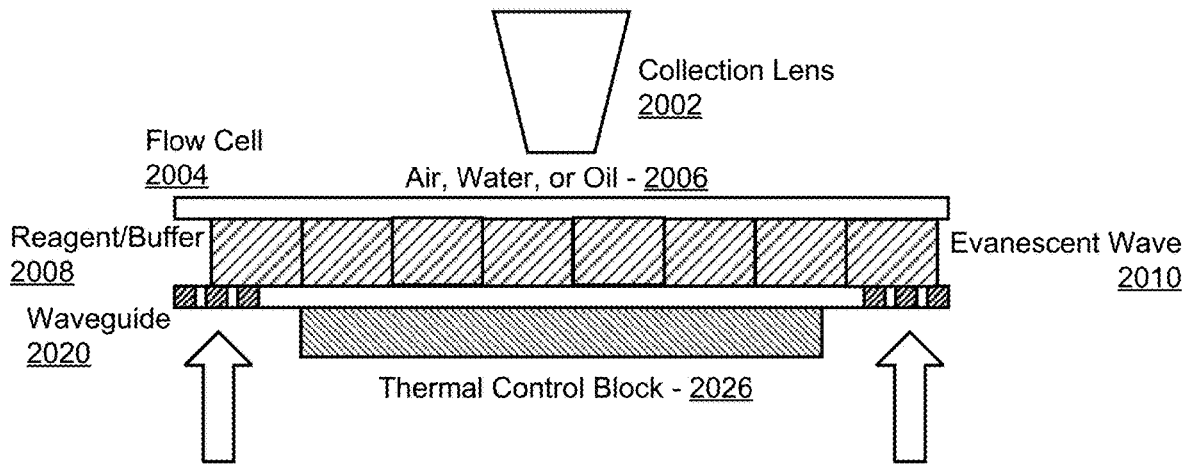

FIGS. 20A and 20B illustrate a possible device for performing imaging of transient probe binding as described herein, using a flow cell 2004 and an integrated optical layout. Reagents are delivered as packets of reagents/buffers 2008 separated by air gaps 2022. FIG. 20A illustrates an example layout where an evanescent wave 2010 is created via coupling laser light 2014 that is transmitted through a prism 2016 (e.g., a TIRF setup). In some embodiments, the temperature of the reaction is controlled by an integrated thermal control 2012 (e.g., in one example the transparent substrate 2024 comprises indium tin oxide electrically coupled and thus altering the temperature of the overall substrate 2024). Reagents are delivered as a continuous flow of reagents/buffers 2008. A grating, waveguide 2020 or photonic structure is used to couple laser light 2014 to create an evanescent field 2010. In some embodiments, thermal control is from a block 2026 that covers the space.

Figure 21:
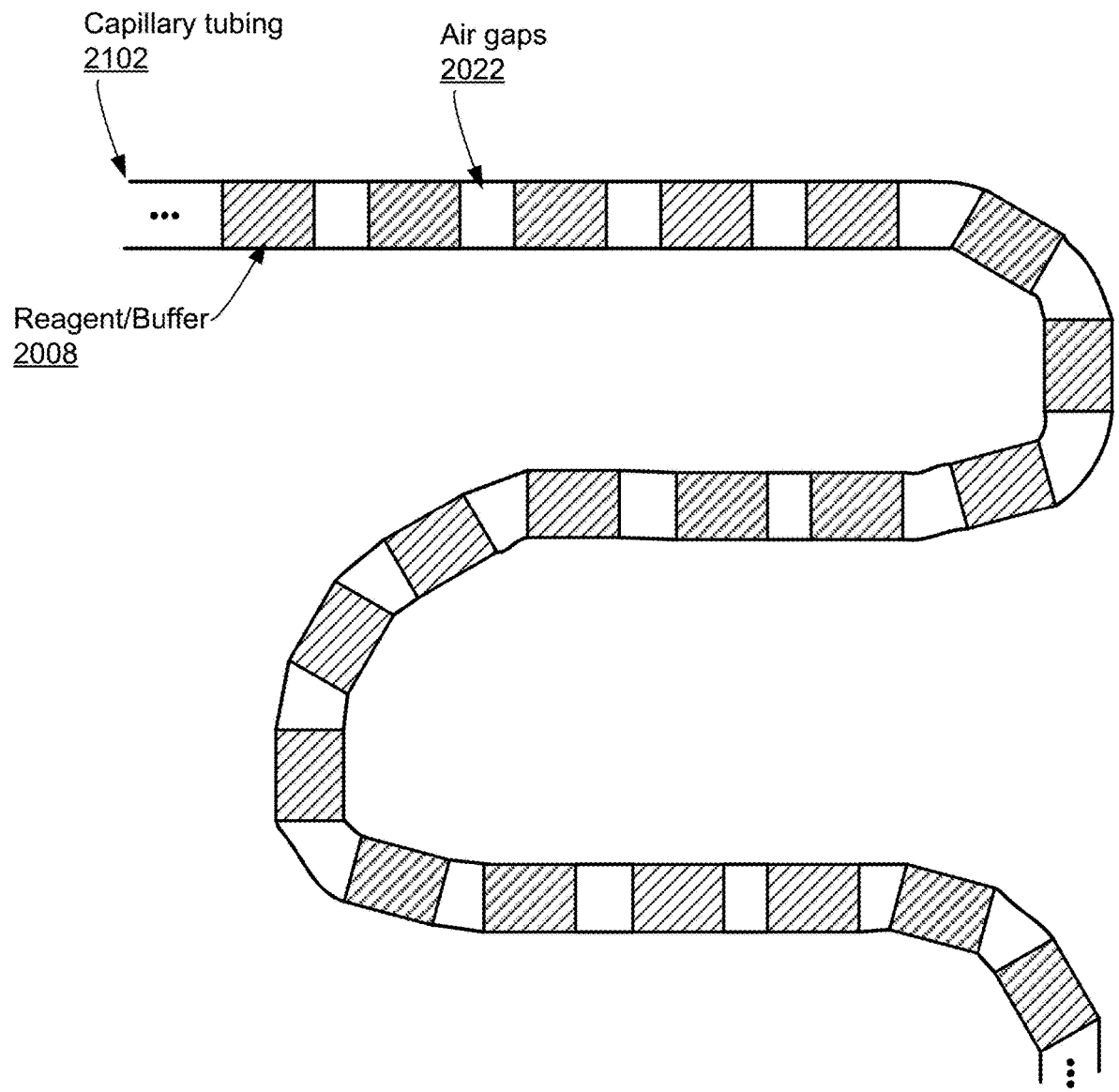
FIG. 21 illustrates an example capillary tubing containing reagents separated by air gaps in accordance with various embodiments of the present disclosure.

Aspects of the layout described in FIG. 20A are interchangeable with aspects of the layout described in FIG. 20B. For example, objective style TIRF, light guide TIRF, condenser TIRF can alternatively be used. The continuous or air-gapped reagent delivery is controlled by a syringe pump or a pressure driven flow in some embodiments. The air-gapped method allows all the reagents 2008 to be pre-loaded in capillary/tubing 2102 (e.g., as illustrated in FIG. 21) or channels and delivered by a push or pull from syringe pump or pressure control system. The air-gapped method allows all the reagents to be pre-loaded in capillary/tubing or channels and delivered by a push or pull from syringe pump or pressure control system. The air gap 2022 comprises air or a gas such as nitrogen or a liquid that is immiscible with the aqueous solution. The air gaps 2022 can also be used to conduct molecular combing as well as reagent delivery. A fluidic device (e.g., a fluidic vessel, cartridge, or chip) comprises the flow cell area where polynucleotide immobilization and optionally elongation is conducted, reagent storing, inlet, outlets and polynucleotide extraction as well as optional structures to shape the evanescent field. In some embodiments, the device is made of glass, plastic or a hybrid of glass and plastic. In some embodiments, thermal and electrical conductivity elements (e.g., metallic) are integrated into the glass and/or plastic components. In some embodiments, the fluidic vessel is a well. In some embodiments, the fluidic vessel is a flow cell. In some embodiments, the surface is coated with one or more chemical layers, biochemical layers (e.g., BSA-biotin, streptavidin), a lipid layer, a hydrogel, or a gel layer. Then a 22×22 mm cover glass coated in vinylsilane (BioTechniques 45:649-658, 2008 or available from Genomic Vision) or cover glass spin-coated with 1.5% Zeonex in chlorobenzene solution. The substrate can also be coated with 2% 3-aminopropyl-triethoxysilane (APTES) or Poly Lysine, and stretching occurs via electorstatic interactions at pH 7.5-8 in HEPES buffer. Alternatively, silanated coverglass spin- or dip-coated in 1-8% polyacrylamide solution containing bis-acrylamide and temed. For this as well as using vinylsilane coated coverglass, cove glass can be coated with 10% 3-methacry-loxypropyltrimethoxysilane (Bind Silane; Pharmacia Biotech) in acetone (v/v) for 1 h. Polyacrylamide coating can also be obtained as described (Liu Q et al. Biomacromolecules, 2012, 13 (4), pp 1086-1092). A number of hydrogel coatings that can be used are described and referenced in Mateescu et al. Membranes 2012, 2, 40-69.

The nucleic acid can also be elongated in an agarose gel by applying alternating current (AC) electric fields. The DNA molecules can be electrophoresed into the gel or the DNA can be mixed with molten agarose and then allowed to set with the agarose. Then an AC field with a frequency of approximately 10 Hz is applied and a field strength of 200 to 400 V/cm is used. Stretching can be done at a range of agarose gel concentrations from 0.5 to 3%. In some case the surface is coated with BSA-Biotin in flow channel or well, then streptavidin or neutravidin is added. This coated coverglass can be used to stretch double strand genomic DNA by first binding the DNA at pH 7.5 buffer and then stretching the DNA in pH 8.5 buffer. In some cases, the streptavidin coated coverglass is used to capture and immobilize the nucleic acid strands, but no stretching is carried out. Hence, the nucleic acid attached at one end, while the other end is dangling in solution.

Rather than using the various microscope-like components of an optical sequencing system such as the GAIIx, in some embodiments, a more integrated, monolithic device is constructed for sequencing. In such embodiments, the polynucleotide is attached and optionally elongated directly on the sensor array or on a substrate that is adjacent to the sensor array. Direct detection on a sensor array has been demonstrated for DNA hybridization to an array (e.g., as described by Lamture et al., Nucleic Acid Research 22:2121-2125, 1994). In some embodiments, the sensor is time gated to reduce background fluorescence due to Rayleigh scattering which is short lived compared to the emissions from fluorescent dyes.

In one embodiment, the sensor is a CMOS detector. In some embodiments, multiple colors are detected (e.g., as described in U.S. Pat. Appl. No. 2009/0194799). In some embodiments, the detector is a Foveon detector (e.g., as described in U.S. Pat. No. 6,727,521). In some embodiments, the sensor array is an array of triple-junction diodes (e.g., as described in U.S. Pat. No. 9,105,537).

In some embodiments, the reagents/buffer are delivered to the flow cell in single dosages (e.g., via a blister pack). Each blister in the pack contains a different oligo from the repertoire of oligonucleotides. Without any mixing or contamination between oligos, a first blister is pierced, and the nucleic acid is exposed to its contents. In some embodiments, wash steps are applied before moving to the next blister in the series. This serves to physically separate the different sets of oligonucleotides, and thus decrease background noise where oligos from a previous set remain in the imaging view.

In some embodiments, the sequencing occurs in the same device or monolithic structure in which the cells were disposed and/or the polynucleotides were extracted. In some embodiments, all reagents needed for conducting the method are pre-loaded on the fluidic device before analysis commences. In some embodiments, the reagents (e.g., probes) are and present in a dry state in the device and are wetted and dissolved before reaction proceeds.

EXAMPLES

Example 1: Preparing Samples for Sequencing

Step 1: Extracting Long Lengths of Genomic DNA.

NA12878 or NA18507 cells (Coriell Biorepository) are grown in culture and harvested. Cells are mixed with low-melting temperature agarose heated to 60° C. The mixture is poured into a gel mold (e.g., purchased from Bio-Rad) and allowed to set into a gel plug, resulting in approximately $4 \times 10^7$ cells (this number is higher or lower depending on the desired density of the polynucleotides). The cells in the gel plug are lysed by bathing the plug in a solution containing Proteinase K. The gel plugs are gently washed in TE buffer (e.g., in a 15 mL falcon tube filled with wash buffer but leaving a small bubble to aid in the mixing, and placing on a tube rotator). The plug is placed in a trough with around 1.6 mL volume and DNA is extracted by using agarase enzyme to digest the DNA. 0.5M MES pH 5.5 solution is applied to the digested DNA. The FiberPrep kit (Genomic Vision, France) and associated protocols are used to carry out this step to give 300 Kb average length of the resulting DNA molecules. Alternatively, genomic DNA extracted from these cell lines is itself available from Corriel and is directly pipetted into the 0.5M MES pH 5.5 solution using a wide bore pipette (~10 uL in 1.2 mL to give <1 μM average spacing).

Step 2: Stretching Molecules on a Surface.

The final part of step 1 renders the extracted polynucleotides in a trough in a 0.5M MES pH 5.5 solution. The substrate cover glass, coated with vinylsilane (e.g., CombiSlips from Genomic Vision) is dipped into the trough and allowed to incubate for 1-10 minutes (depending on the density of polynucleotides required). The cover glass is then slowly pulled out, using a mechanical puller, such as a syringe pump with a clip attached to grasp the cover glass (alternatively, the FiberComb system from Genomic Vision is used). The DNA on the coverglass is cross-linked to the surface using an energy of 10,000 micro Joules using a crosslinker (Stratagene, USA). If the process is carried out carefully, it results in High Molecular Weight (HMW) polynucleotides with an average length of 200-300 Kb elongated on the surface, with molecules greater than 1 Mb, or even around 10 Mb, in length present amongst the population of polynucleotides. With greater care and optimization, the average length is shifted to the megabase range (see Mega-base range combing section above).

As an alternative, as mentioned above, pre-extracted DNA (e.g., Human Male Genomic DNA from Novagen cat.

No. 70572-3 or Promega) is used, and comprises a good proportion of genomic molecules of greater than 50 Kb. Here, a concentration of approximately 0.2-0.5 ng/μL, with dipping for approximately 5 minutes is sufficient to provide a density of molecules where a high fraction is individually resolved using diffraction limited imaging.

Step 3: Making a Flow Cell.

The coverslip is pressed onto a flow cell gasket fashioned from double-sided sticky 3M sheet that has already been attached to a glass slide. The gasket (with both sides of the protective layer on the double-sided sticky sheet on) is fashioned, using a laser cutter, to produce one or more flow channels. The length of the flow channel is longer than the length of the coverglass, so that when the coverglass is placed at the center of the flow channel, the portions of the channel one at each end that are not covered by the coverglass is used, respectively, as inlets and outlets for dispensing fluids into and out of the flow channel. Fluids pass above the elongated polynucleotides that are adhered on the vinyl-silane surface. The fluids are flowed through the channel by using safety swab sticks (Johnsons, USA) at one end to create suction as fluid is pipetted in at the other end. The channel is pre-wetted with Phosphate Buffered Saline-Tween and Phosphate Buffered Saline (PBS-washes).

Step 4: Denaturation of Double Stranded DNA.

Before the next oligo can be added the previous oligo needs to be efficiently washed away; this can be done by exchanging with buffer up to 4 times and optionally using denaturing agents such as DMSO or an alkali solution to remove persistent binding) The double-stranded DNA is denatured by flushing alkali (0.5M NaOH) through the flow cell and incubating for approximately 20-60 minutes at room temperature. This is followed by PBS/PBST washes. Alternatively, incubation is also done with 1 M HCL for 1 hour followed by PBS/PBST washes.

Step 5: Passivation.

Optionally, a blocking buffer such as BlockAid (Invitrogen, USA) is flowed in and incubated for ~5-15 minutes. This is followed by the PBS/PBST washes.

Example 2: Sequencing by Transient Binding of Oligonucleotides to a Denatured Polynucleotide Step 1: Adding Oligos Under Transiently Binding Conditions.

The flow cell is pre-conditioned with PBST and optionally Buffer A (10 mM Tris-HCl, 100 mM NaCl, 0.05% Tween-20, pH 7.5). ~1-10 nM of each of the oligos are applied to the elongated denatured polynucleotides in Buffer B (5 mM Tris-HCl, 10 mM $MgCl_2$, 1 mM EDTA, 0.05% Tween-20, pH 8) or Buffer B+5 mM Tris-HCl, 10 mM $MgCl_2$, 1 mM EDTA, 0.05% Tween-20, pH 8, 1 mM PCA, 1 mM PCD, 1 mM Trolox). The length of the oligo typically ranges from 5 to 7 nucleotides and the reaction temperature depends on the Tm of the oligo. One probe type that we have used is of the general formula 5'-Cy3-NXXXXXN-3' (X are specified bases, N are degenerate positions), with LNA nucleotides at positions 1, 2, 4, 6 and 7; DNA nucleotides at positions 3 and 5 and were purchased from Sigma Proligo and as previously used by Pihlak et al. Binding of temperature was linked to the Tm of each oligo sequence.

After washing with A+ and B+ solution transient binding of oligonucleotides is carried out with between 0.5 and 100 nM of oligo (typically between 3 nm and 10 nm) in B+ solution at room temperature for an LNA DNA chimera oligo 3004 NTgGcGN (where upper case letters are LNA and lowercase are DNA nucleotides). Different temperatures and/or salt conditions (as well as concentrations) are used for different oligo sequences, according to their Tm and binding behavior. If a FRET mechanism is used for detection, a much higher concentration of oligo, up to 1 uM can be used. In some embodiments, the FRET is between an intercalating dye molecules (1 in 1000 to 1 in 10,000 diluted form neat depending on which intercalating dye is used from YOYO-1, Sytox Green, Sytox Orange, Sybr Gold etc; Life Technologies) which intercalate into the transiently formed duplexes and and a label on the oligo. In some embodiments, intercalating dye is directly used as label, without FRET. In this case, the oligos are not labeled. As well as being cheaper, unlabeled oligos can be used at higher concentrations than labelled oligos, because the background from intercalated dye upon heteroduplex formation is 100-1000 brighter (e.g., depending on which intercalant is used) than un-intercalated dye.

Step 2: Imaging—Taking Multiple Frames.

The flow channel is placed on an inverted microscope (e.g., Nikon Ti-E) equipped with Perfect Focus, TIRF attachment, and TIRF Objective lasers and a Hamamatsu 512×512 Back-thinned EMCCD camera. The probes are added in Buffer B+ and optionally supplemented with imaging.

The probes binding to the polynucleotides disposed on the surface are illuminated by an evanescent wave generated by total internal reflection of 75-400 mW laser light (e.g., green light at 532 nm) conditioned via fiber optic scrambler (Point Source) at a TIRF angle of ~1500 through a 1.49 NA 100× Nikon oil immersion objective on a Nikon Ti-E with TIRF attachment. The images are collected through the same lens with 1.5× further magnification and projected via the dichroic mirror and an emission filter to a Hamamatsu ImageEM camera. 5000-30,000 frames of 50-200 milliseconds are taken with an EM gain of 100-140 using Perfect Focus. Preferably high laser power (e.g., 400 mW) is used in the early seconds to bleach out initial non-specific binding, which reduces the almost a blanket of signal from the surface to a lower density where individual binding events are resolved. Thereafter the laser power is optionally lowered.

FIGS. 22A-22E illustrate examples of illumination of probes transiently binding to target polynucleotides. In these figures, the target polynucleotides are from human DNA. Dark spots indicate regions of probe fluorescence, with darker spots indicating more regions that were bound more often by probes (e.g., more photons were collected). FIGS. 22A-22E are images from a time series (e.g., a video) captured during sequencing of one target polynucleotide. Points 2202, 2204, 2206, 2208 are indicated throughout the time series as examples of regions in the polynucleotide that were bound with more or less intensity over time (e.g., as different sets of oligonucleotides were exposed to the target polynucleotide).

Imaging Buffer is Added.

The imaging buffer is supplemented or replaced by a buffer containing beta-mercaptoethanol, enzymatic redox system, and/or ascorbate and gallic acid in some embodiments. Fluorophores are detected along lines, indicating that binding has occurred. Optionally, if the flow cell is made with more than one channel, one of the channels are stained with YOYO-1 intercalating dye for checking the density of polynucleotides and quality of the polynucleotide elongation (e.g., using Intensilight or 488 nm laser illumination).

Step 3: Imaging—Moving to Other Locations (Optional Step).

The cover glass, which has been mounted onto the slide holder of the Nikon Ti-e (via attachment to glass slide as part of the flow cell) is translated with respect to the objective lens (hence the CCD) so that separate locations are imaged. The imaging is done at a multiple of other locations so that probes binding to polynucleotides or parts of polynucleotides rendered at different locations (outside the field of view of the CCD at its first position) is imaged. The image data from each location is stored in computer memory.

Step 4: Adding the Next Set of Oligos.

The next set of oligos is added and steps 1-3 are repeated until the whole of the polynucleotide has been sequenced.

Step 5: Determining the Location and Identity of Binding.

The location of each fluorescent point signal is detected, recording the pixel locations whereupon the fluorescence from the bound labels is projected. The identity of the bound oligonucleotide is determined by determining which labeled oligonucleotides have been bound e.g., using wavelength selection by optical filters—the fluorophores, are detected across multiple filters and in this case the emission signature of each fluorophore across the filter set is used to determine the identity of the fluorophore and hence the oligonucleotide. Optionally, if the flow cell is made with more than one channel, one of the channels is stained with YOYO-1 intercalating dye, for checking the density of polynucleotides and quality of the polynucleotide elongation (e.g., by using Intensilight or 488 nm laser illumination). One or more images or movies are taken, one for each of the fluorescence wavelengths used to label the oligonucleotides.

Step 6: Data Processing.

When both strand of the duplex remain attached to the surface, binding of oligos occurs to their complementary locations on both strands of the double-strand simultaneously. Then the total data-set is analyzed to find sets of oligos that give closely localizing signals to a particular position on the nucleic acid, their locations are confirmed by overlapping the oligo sequences that correspond to a chosen point in the polynucleotide; this then reveals two overlapping tiling series of oligos each. Which tiling series the next signal in the locality fits, indicates which strand it is binding to.

As the strands remain fixed on the surface, the binding locations recorded for each oligo can be overlaid using a software script running an algorithm. This results in the signals showing that the oligo binding locations fall within the framework of two oligonucleotide sequence tiling paths, a separate (but which should be complementary) path for each strand of the denatured duplex. Each tiling path, if complete, spans the entire length of the strand. The tiled sequence for each strand is then compared to provide a double-strand (also known as 2D) consensus sequence. If there are gaps in one of the tiling paths, the sequence of the complementary tiling path is taken. In some embodiments, the sequence is compared with multiple copies of the same sequence or to the reference, to aid base assignment and to close gaps.

Example 3: Detecting the Location of Epi-Marks on the Polynucleotide

Optionally before (or sometimes after or during) the oligo binding process, transient binding of epigenomic binding reagents is carried out. Depending on which binding reagent is used, binding is done before or after denaturation. For anti-methyl C antibodies binding is done on denatured DNA whereas for methyl binding proteins, binding is done on double-stranded DNA before any denaturation step.

Step 1—Transient Binding of Methyl-Binding Reagents.

After denaturation, the flow cell is flushed with PBS-washes and a Cy3B labelled anti-methyl antibody 3D3 clone (Diagenode) is added in PBS.

Alternatively, before denaturation, the flow cell is flushed with PBS and Cy3B-labeled MBD1 is added.

Imaging is conducted as described above for transient oligo binding.

Step 2: Stripping Away Methyl-Binding Reagents.

Typically, the epi-analysis is done before sequencing. Therefore, optionally the methyl-binding reagents are flushed out before the polynucleotide before sequencing commences. This is done by flowing through multiple cycles of PBS/PBST and/or a high salt buffer and SDS and then checking by imaging that removal has occurred. If it is evident that more than a negligible amount of binding reagent remains, harsher treatments such as the chaotrophic salt, GuCL is flowed through to remove the remaining reagents.

Step 3: Data Correlation.

After sequencing epi-genomics data has been obtained correlations are made between the location of the sequencing binding locations and epi-binding location is correlated to provide the sequence context of the methylation.

Example 4: Fluorescence Collected from Transient Binding in Lambda Phage DNA

FIGS. 23A, 23B, and 23C illustrate examples of transient binding events. They collectively illustrate transient binding of Oligo I.D. Lin2621, Cy3 labeled 5' NAgCgGN 3' at 1.5 nM concentration in Buffer B+ at room temperature. The target polynucleotide is lambda phage genome that has been combed manually onto a vinylsilane surface (Genomic Vision) in MES pH 5.5 buffer+0.1 M NaCl. Laser 532 nm at 400 mW through Point Source Fiber Optic scrambler. The fluorescence has been collected with a TIRF attachment and multi-chroic, including a 532 nm excitation band, a TIRF Objective 100×, 1.49NA, and with extra 1.5× magnification. No vibration isolation was implemented. The images were captured with perfect focus onto Hamamatsu ImageEM 512×512 with 100 EM Gain setting. 10000 frames were collected over 100 ms. The concentration of Cy3 in the oligonucleotide probe sets was approximately 250 nM-300 nM. FIG. 23A displays the fluorescence that was collected before cross-correlation drift correction in ThunderSTORM. FIG. 23B displays fluorescence that was collected after cross-correlation drift correction with scale bar. FIG. 23C displays fluorescence in a magnified region of FIG. 23B. FIG. 23C show long polynucleotide strands traced out by the persistent binding of the Lin2621 to multiple locations. From the image, it is clear that the target polynucleotide strands were immobilized and elongated on the imaging surface at distances closer than the diffraction limit of Cy3 emission.

Example 5: Fluorescence Collected from Transient Binding in Synthetic DNA

FIG. 24 illustrates an example of fluorescence data collected from three different polynucleotide strands. Multiple probing and washing steps are shown on synthetic 3 kilobase denatured double-stranded DNA. Synthetic DNA was combed in MES pH 5.5 on a vinylsilane surface and denatured. A series of binding and washing steps were carried out, and a video was recorded and processed in ImageJ using ThunderSTORM. Three example strands (1, 2, 3) were excised from the super-resolution image for the following experimental series carried out with 10 nM oligo in Buffer B+ at ambient temperature: Oligo 3004 binding, washing, oligo 2879 binding, washing, oligo 3006 binding, washing and oligo 3004 binding (again). This shows that a binding map can be derived from transient binding, the binding pattern can be erased by washing, a different binding pattern is then obtained with a different oligo on the same first and second strands of the synthetic DNA. The return to oligo 3004 on the last of the series and its resemblance to the pattern when it is used as the first in the series points to the robustness of the process even without any attempt at optimization.

The experimentally determined binding locations correspond to the expected, with duplex strands 1 and 3 showing 3 of 4 possible perfect match binding sites, and duplex strand 2 showing all 4 binding locations and one prominent mismatch location. It is observed that the second probing with oligo 3004 appears to show cleaner signals, perhaps due to less mismatch. This is consistent with the likelihood that the temperature is slightly raised due to heating from pro-longed exposure to laser light.

The oligo sequences used in this experiment are as follows (Capitalized bases are Locked Nucleic Acid (LNA)):

```
Olio 3004: 5' cy3 NTgGcGN

Oligo 2879: 5' cy3 NGgCgAN

Oligo 3006: 5' cy3 NTgGgCN:
```

The Sequence Listing (at bottom of document) for sequence of 3 kbp synthetic template is as follows:

```
                                        (SEQ ID NO. 2)
AAAAAAAAACCGGCCCAGCTTTCTTCATTAGGTTATACATCTACCGCTCGC

CAGGGCGGCGACCTCGCGGGTTTTCGCTATTTATGAAAATTTTCCGGTTTA

AGGCGTTTCCGTTCTTCTTCGTCATAACTTAATGTTTTTATTTAAAATACC

CTCTGAAAAGATAGGATAGCACACGTGCTGAAAGCGAGGCTTTTTGGCCTC

TGTCGTTTCCTTTCTCTGTTTTTGTCCGTGGAATGAACAATGGAAGTCAAC

AAAAAGCAGCTGGCTGACATTTTCGGTGCGAGTATCCGTACCATTCAGAAC

TGGCAGGAACAGGGAATGCCCGTTCTGCGAGGCGGTGGCAAGGGTAATGAG

GTGCTTTATGACTCTGCCGCCGTCATAAAATGGTATGCCGAAAGGGATGCT

GAAATTGAGAACGAAAAGCTGCGCCGGGAGGTTGAAGAACTGCGGTTCTTA

TACATCTAATAGTGATTATCTACATACATTATGAATCTACATTTTAGGTAA

AGATTAATTGAGTACCAGGTTTCAGATTTGCTTCAATAAATTCTGACTGTA

GCTGCTGAAACGTTGCGGTTGAACTATATTTCCTTATAACTTTTACGAAAG

AGTTTCTTTGAGTAATCACTTCACTCAAGTGCTTCCCTGCCTCCAAACGAT

ACCTGTTAGCAATATTTAATAGCTTGAAATGATGAAGAGCTCTGTGTTTGT

CTTCCTGCCTCCAGTTCGCCGGGCATTCAACATAAAAACTGATAGCACCCG

GAGTTCCGGAAACGAAATTTGCATATACCCATTGCTCACGAAAAAAAATGT
```

-continued
```
CCTTGTCGATATAGGGATGAATCGCTTGGTGTACCTCATCTACTGCGAAAA

CTTGACCTTTCTCTCCCATATTGCAGTCGCGGCACGATGGAACTAAATTAA

TAGGCATCACCGAAAATTCAGGATAATGTGCAATAGGAAGAAAATGATCTA

TATTTTTTGTCTGTCCTATATCACCACAAAACCTGAAACTGGCGCGTGAGA

TGGGGCGACCGTCATCGTAATATGTTCTAGCGGGTTTGTTTTTATCTCGGA

GATTATTTTCATAAAGCTTTTCTAATTTAACCTTTGTCAGGTTACCAACTA

CTAAGGTTGTAGGCTCAAGAGGGTGTGTCCTGTCGTAGGTAAATAACTGAC

CTGTCGAGCTTAATATTCTATATTGTTGTTCTTTCTGCAAAAAAGTGGGGA

AGTGAGTAATGAAATTATTTCTAACATTTATCTGCATCATACCTTCCGAGC

ATTTATTAAGCATTTCGCTATAAGTTCTCGCTGGAAGAGGTAGTTTTTTCA

TTGTACTTTACCTTCATCTCTGTTCATTATCATCGCTTTTAAAACGGTTCG

ACCTTCTAATCCTATCTGACCATTATAATTTTTTAGAATGCGGCGTTTTCC

GGAACTGGAAAACCGACATGTTGATTTCCTGAAACGGGATATCATCAAAGC

CATGAACAAAGCAGCCGCGCTGGATGAACTGATACCGGGGTTGCTGAGTGA

ATATATCGAACAGTCAGGTTAACAGGCTGCGGCATTTTGTCCGCGCCGGGC

TTCGCTCACTGTTCAGGCCGGAGCCACAGACCGCCGTTGAATGGGCGGATG

CTAATTACTATCTCCCGAAAGAATCCGCATACCAGGAAGGGCGCTGGGAAA

CACTGCCCTTTCAGCGGGCCATCATGAATGCGATGGGCAGCGACTACATCC

GTGAGGTGAATGTGGTGAAGTCTGCCCGTGTCGGTTATTCCAAAATGCTGC

TGGGTGTTTATGCCTACTTTATAGAGCATAAGCAGCGCAACACCCTTATCT

GGTTGCCGACGGATGGTGATGCCGAGAACTTTATGAAAACCCACGTTGAGC

CGACTATTCGTGATATTCCGTCGCTGCTGTTAATTGAGTTTATAGTGATTT

TATGAATCTATTTTGATGATATTATCTACATACGACTGGCGTGCCATGCTT

GCCGGGATGTCAAATTTAATAAGGTGATAGTAAATAAAACAATTGCATGTC

CAGAGCTCATTCGAAGCAGATATTTCTGGATATTGTCATAAAACAATTTAG

TGAATTTATCATCGTCCACTTGAATCTGTGGTTCATTACGTCTTAACTCTT

CATATTTAGAAATGAGGCTGATGAGTTCCATATTTGAAAAGTTTTCATCAC

TACTTAGTTTTTTGATAGCTTCAAGCCAGAGTTGTCTTTTTCTATCTACTC

TCATACAACCAATAAATGCTGAAATGAATTCTAAGCGGAGATCGCCTAGTG

ATTTTAAACTATTGCTGGCAGCATTCTTGAGTCCAATATAAAAGTATTGTG

TACCTTTTGCTGGGTCAGGTTGTTCTTTAGGAGGAGTAAAAGGATCAAATG

CACTAAACGAAACTGAAACAAGCGATCGAAAATATCCCTTTGGGATTCTTG

ACTCGATAAGTCTATTATTTTCAGAGAAAAAATATTCATTGTTTTCTGGGT

TGGTGATTGCACCAATCATTCCATTCAAAATTGTTGTTTTACCACACCCAT

TCCGCCCGATAAAAGCATGAATGTTCGTGCTGGGCATAGAATTAACCGTCA

CCTCAAAAGGTATAGTTAAATCACTGAATCCGGGAGCACTTTTTCTATTAA

ATGAAAAGTGGAAATCTGACAATTCTGGCAAACCATTTAACACACGTGCGA

ACTGTCCATGAATTTCTGAAAGAGTTACCCCTCTAAGTAATGAGGTGTTAA

GGACGCTTTCATTTTCAATGTCGGCTAATCGATTTGGCCATACTACTAAAT

CCTGAATAGCTTTAAGAAGGTTATGTTTAAAACCATCGCTTAATTTGCTGA

GATTAACATAGTAGTCAATGCTTTCACCTAAGGAAAAAAACATTTCAGGGA
```

-continued

GTTGACTGAATTTTTTATCTATTAATGAATAAGTGCTTGACCTATTTCTTC

ATTACGCCATTATACATCTAGCCCACCGCTGCCAAAAAAAAA

Example 6: Integrated Isolation of Single Cells, Extracting Nucleic Acids and Sequencing Step 1: Design and Fabricate Microfluidic Architecture Microchannels are designed to accommodate cells from a human cancer cell line with a typical diameter of 15 um, so the microfluidic network has minimal depths and widths of 33 um. The device comprises an inlet for cells and an inlet for buffer that merge into a single channel to feed the single-cell trap (illustrated in FIG. 17). At the intersection between the cell and buffer inlets, cells get aligned along the side wall of the feeding channel where one or more traps are located. Each trap is a simple constriction dimensioned to capture a cell from a human cancer cell line. The constriction for cell trapping has a trapezoidal cross section: It is 4.3 um wide at the bottom, 6 um at middle depth, and 8 um at the top with a depth of 33 um. Each cell trap connects the feeding channel to a bifurcation, one side of which is a waste channel (not shown in FIG. 17) and the other a channel comprising the flow-stretch section (for nucleic acid elongation and sequencing), one for each cell. The flow-stretch section consists of a 20 um (or up to 2 mm) wide, 450 um-long, 100 nm (or up to 2 um-deep) channel. In some embodiments the flow-stretch channel is narrower to start and widens to the stated dimensions.

Step 2: Device Fabrication

The device is fabricated by replicating a nickel shim using injection molding of TOPAS 5013 (TOPAS). Briefly, a silicon master is produced by UV lithography and reactive ion etching. A 100-nm NiV seeding layer is deposited and nickel is electroplated to a final thickness of 330 um. The Si master is chemically etched away in KOH. Injection molding is performed using a melt temperature of 250° C., a mould temperature of 120° C., a maximum holding pressure of 1,500 bar for 2 s, and an injection rate varying between 20 cm3/s and 45 cm3/s. Finally, either coverglass (1.5) is bonded to the device or a 150 um TOPAS foil is used to seal the device by a combined UV and thermal treatment under a maximum pressure of 0.51 MPa. The surface roughness of the foil is reduced by pressing the foil at 140° C. and 5.1 MPa for 20 min between two flat nickel plates electroplated from silicon wafers before sealing the device. This ensures that the lid of the device is optically flat, allowing for high-NA optical microscopy. The device is mounted on an inverted fluorescence microscope (Nikon Ti-E) equipped with an oil TIRF objective (100×/NA 1.49), and an EMCCD camera Hamamatsu ImageEM 512). Fluids are driven through the device using a pressure controller (MFCS, Fluigent) at pressures in the 0 to 10 mbar range. The device is primed with ethanol, and then degassed, FACSFlow Sheath Fluid (BD Biosciences) is loaded in all microchannels except the microchannel connecting the flow-stretch device The selective loading is effected by putting a negative pressure or suction at the outlet of the waste channel, while putting a positive pressure at the outlet of the flow stretch channel, while maintaining a positive pressure at the inlet of feeding channel from where the solutions are introduced. A buffer suitable for single-molecule imaging and electrophoresis (0.5×TBE+0.5% v/v Triton-X100+1% v/v beta-mercaptoethanol, BME) is loaded in the channels of the flow-stretch device. This buffer prevents DNA sticking in the flow-stretch section and suppresses electroosmotic flow that can counteract the introduction of the extracted DNA when the height of the flow-stretch section is low.

Step 3: Cell Preparation

LS174T colorectal cancer cells are cultured in Dulbecco's modified Eagle's medium (DMEM; Gibco) with 10% fetal bovine serum (FBS; Autogen-Bioclear UK Ltd.) and 1% penicillin/streptomycin (Lonza) before freezing at a concentration of 1.7 106 cells per milliliter in 10% DMSO in FBS. After thawing, cell suspension is mixed 1:1 with FACSFlow buffer, centrifuged at 28.8×g (A-4-44, Eppendorf) for 5 min, and resuspended in FACSFlow buffer. Finally, the cells are stained with 1 uM Calcein AM (Invitrogen) and loaded in the chip at 0.35 $10^6$ cells per milliliter. Approximately 5-10,000 cells are loaded and the first cell trapped in each trap is analyzed.

Step 4: Operation

Cells and buffer are introduced simultaneously, aligning the cells along the side wall of the microchannel where the trap is located. A single cell is captured and kept in the trap for a buffer flow through the trap up to 30 nL/min. The lysis buffer composed of 0.5×TBE+0.5% v/v Triton-X100+0.1 uM YOYO-1 (Invitrogen) is loaded in one of the inlets and injected at 10 nL/min through the trap for 10 min. Then, the solution is exchanged to a buffer without YOYO-1 in all wells to stop the staining. Next, the cell nucleus is exposed to blue excitation light at a dose of 1 $nW/(um)^2$ for up to 300 s, causing a partial photonicking of the DNA (see SI Appendix of www.pnas.org/cgi/doi/10.1073/pnas.1804194115). Then, the buffer is changed to a solution containing BME (0.5×TBE+0.5% v/v triton-X100+1% v/v BME), and the intensity of the fluorescence lamp is lowered to the minimum intensity that still allows fluorescence imaging. Next, the temperature is raised to 60° C., and a proteolysis solution (Proteinase K>200 µg $mL^{-1}$ (Qiagen), 0.5×TBE+0.5% v/v Triton-X100+1% v/v BME+200 g/mL) is introduced, pushing the lysate through the trap. DNA travels through to the adjacent flow stretch section, and an oil immersion objective is moved into place for single molecule imaging (100×, NA 1.49, with an additional 1.5× magnification giving a 120-nm pixel size). DNA fragments are introduced from the microchannel to the the flow-stretch device using electrophoresis by applying a voltage of 5 to 10 V across the flow-stretch section. When a DNA fragment has both ends in opposite microchannels, voltage is turned off. The 450 um portion of the molecule stretched at 100-150% corresponds to >1 Megabase lengths of the extracted genomic DNA from the single cell. In some embodiments, after proteolysis the DNA content is pushed through the device by substituting 0.5×TBE for a capture buffer; in such embodiments the flow stretch section dimensions are optionally larger, so that thousands of megabase fragments can concurrently be captured (by hydrophobic or electrostatic interactions) and stretched inside the channel. This is done either by using a pH buffer 8 (e.g. HEPES) and here the coverglass that is bonded bears positive charges such as APTES or poly-lysine or a vinylsilane cover glass is bonded and 0.5M MES Buffer at pH 5.5-5.7 is used to flow in the DNA which is then combed by following the MES buffer with air. If the or foil comprises Zeonex, then molecular combing can be done with 0.6M MES buffer at pH 5.7.

Once double-stranded nucleic acid is immobilized, denaturation solution, 0.5M NaOH and or 6% DMSO is flowed through. Then the single cell sample is ready for the sequencing methods of this invention, where a repertoire of oligos is flowed through and oligo binding is imaged.

In some embodiments, the cell lysis is two step, so that RNA does not contaminate and cause fluorescence within the flow stretch section. Here, the first lysis buffer (e.g., 0.5×TBE containing 0.5% (v/v) Triton X-100, to which the DNA intercalating YOYO-1 dye is added) is applied. This buffer lyses the cell membrane, releasing the cytosol contents into the trap outlets filled with 10-20 μl nuclease-free H2O, leaving the nucleus with the DNA in the trap (e.g., as described by van Strijp et al. Sci Rep. 7:11030 (2017). The cytosol content of each cell is lysed and either shunted into the waste outlet or the device is designed to have a flow-stretch section for RNA that is separate from the flow stretch section for DNA. In some embodiments, RNA is sent to a separate flow stretch section, that has been coated with oligo dT, which captures polyA RNA. In some embodiments the flow stretch section for RNA comprises nanowells or nanopits (Marie et al, Nanoscale DOI: 10.1039/c7nr06016e) 2017), in which the RNA is trapped and enzymatic reagents are used to add capture sequence, using for example polyA polymerase. The nuclear lysis is performed with a second buffer (0.5×TBE containing 0.5% (v/v) Triton X-100 and Proteinase K) and the DNA is shunted to the flow-stretch section for DNA.

To minimize loss of the nucleic acids, the distance from the traps and flow stretch section is short, and the device wall are well passivated including by coating with lipid (e.g., as described by Persson et al, Nanoletters 12:2260-5 (2012)).

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope unless otherwise claimed. No language in the specification should be construed as indicating any non-claimed element as essential to the practice of the invention.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

The citation and incorporation of patent documents herein is done for convenience only and does not reflect any view of the validity, patentability, and/or enforceability of such patent documents.

The present invention can be implemented as a computer program product that comprises a computer program mechanism embedded in a non-transitory computer readable storage medium. For instance, the computer program product could contain the program modules shown in any combination of FIG. 1. These program modules can be stored on a CD-ROM, DVD, magnetic disk storage product, USB key, or any other non-transitory computer readable data or program storage product.

The invention is most thoroughly understood in light of the teachings of the specification and the references cited within. Many modifications and variations can be made without departing from its spirit and scope, as will be apparent to those skilled in the art. The specific embodiments described herein are offered by way of example, only. The embodiments were chosen and described in order to best explain the principles and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed:

1. A method of determining a sequence of at least a portion of a nucleic acid molecule, comprising:

fixing the nucleic acid molecule in a double stranded linearized stretched form on a test substrate, thereby forming a fixed stretched double stranded nucleic acid on the test substrate;

denaturing the fixed stretched double stranded nucleic acid to a single stranded form on the test substrate, thereby obtaining a fixed first strand and a fixed second strand of the nucleic acid on the test substrate, wherein respective bases on the fixed second strand are adjacent to their complementary bases on the fixed first strand;

exposing the fixed first strand and the fixed second strand to a respective oligonucleotide probe species in a set of oligonucleotide probe species, wherein each respective oligonucleotide probe species of the set of oligonucleotide probe species is capable of hybridizing to its complementary portion located at a plurality of locations on the fixed first strand or the fixed second strand and comprises (i) a unique respective predetermined sequence, (ii) a predetermined length, and (iii) a respective label selected from the group consisting of a dye, a fluorescent nanoparticle, a plasmon resonant particle, a light-scattering particle, and a fluorescence resonance energy transfer (FRET) partner, wherein the exposing step occurs under conditions such that:

i) oligonucleotide probes of the respective oligonucleotide probe species of the set of oligonucleotide probe species repetitively transiently and reversibly bind to the plurality of locations on the fixed first strand or the fixed second strand on the test substrate, thereby forming a respective transient heteroduplex on each of the plurality of locations on the fixed first strand or the fixed second strand on the test substrate, and ii) respective instances of optical activity from the respective label are generated by repetitively transiently and reversibly binding the oligonucleotide probes of the respective oligonucleotide probe species of the set of oligonucleotide probe species to the plurality of locations on the fixed first strand or the fixed second strand on the test substrate and are detected on each of the plurality of locations on the fixed first strand or the fixed second strand on the test substrate;

determining which portions on the fixed first strand or the fixed second strand are complementary to the respective oligonucleotide probe species of the set of oligonucleotide probe species by measuring the respective instances of optical activity on each of the plurality of locations on the fixed first strand or the fixed second strand on the test substrate occurring during the exposing step using a two-dimensional imager capable of detecting the respective instances of optical activity generated from the respective label, thereby obtaining a first set of positions on the fixed first strand or the fixed second strand which are complementary to the respective oligonucleotide probe species of the set of oligonucleotide probe species;

washing the test substrate to remove the respective oligonucleotide probe species of the set of oligonucleotide probe species from the test substrate;

repeating the exposing step, measuring step, and washing step by exposing the fixed first strand and the fixed second strand on the test substrate to another respective oligonucleotide probe species in the set of oligonucleotide probe species, thereby obtaining a second set of positions on the fixed first strand or the fixed second strand which are complementary to the another respective oligonucleotide probe species of the set of oligonucleotide probe species; and determining the sequence of at least the portion of the nucleic acid molecule based on the first set of positions on the fixed first strand or the fixed second strand which are complementary to the respective oligonucleotide probe species of the set of oligonucleotide probe species and the second set of positions on the fixed first strand or the fixed second strand which are complementary to the another respective oligonucleotide probe species of the set of oligonucleotide probe species.

2. The method of claim 1, wherein each duration of said repetitively transiently and reversibly binding the individual oligonucleotide probes of the respective oligonucleotide probe species of the set of oligonucleotide probe species to the plurality of locations of the fixed first strand or the fixed second strand on the test substrate persists for less than 10 seconds.

3. The method of claim 1, wherein
more than one different oligonucleotide probe species in the set of oligonucleotide probe species are exposed to the fixed first strand and the fixed second strand during the exposing step.

4. The method of claim 3, wherein
said more than one different oligonucleotide probe species in the set of oligonucleotide probe species that are exposed to the fixed first strand and the fixed second strand during the exposing step have different labels.

5. The method of claim 1, wherein:
the exposing step and the measuring step for the respective oligonucleotide probe species in the set of oligonucleotide probe species are performed at a first temperature; and
the exposing step and the measuring step for the another respective oligonucleotide probe species in the set of oligonucleotide probe species in the repeating step are performed at a second temperature.

6. The method of claim 1, wherein the measuring step measures more than 5000 photons generated from the respective label from the transient heteroduplex located on each of the plurality of locations on the fixed first strand or the fixed second strand on the test substrate.

7. The method of claim 1, wherein said unique respective predetermined sequence comprises a unique N-mer sequence, wherein N is an integer.

8. The method of claim 1, wherein the nucleic acid molecule is at least 140 bases in length.

9. The method of claim 1, wherein the nucleic acid molecule is at least 10,000 bases in length.

10. The method of claim 1, wherein the fixing step comprises applying the nucleic acid molecule to the test substrate by molecular combing, flow stretching nanoconfinement, or electro-stretching.

11. The method of claim 1, wherein, for the respective oligonucleotide probe species of the set of oligonucleotide probe species, the respective instances of optical activity from the respective label are generated by repetitively transiently and reversibly binding the oligonucleotide probes of the respective oligonucleotide probe species of the set of oligonucleotide probe species to their complementary portions located at the plurality of locations of the fixed first strand on the test substrate, and for the another respective oligonucleotide probe species of the set of oligonucleotide probe species, the respective instances of optical activity from the respective label are generated by repetitive transiently and reversibly binding the oligonucleotide probes of the another respective oligonucleotide probe species of the set of oligonucleotide probe species to their complementary portions located at the plurality of locations of the fixed second strand on the test substrate at different times.

12. The method of claim 1, wherein
each respective probe species in the set of oligonucleotide probe species has an oligonucleotide probe sequence of length N, wherein N is a 3, 4, 5, or 6 oligonucleotides,
the set of oligonucleotide probe species includes a complete repertoire of probe sequences of length N oligonucleotides, and
the repeating step is performed for a plurality of times by exposing the fixed first strand and the fixed second strand to a different respective oligonucleotide probe species in the set of oligonucleotide probe species.

13. The method of claim 12, wherein each respective probe species in the set of oligonucleotide probe species comprises one or more degenerate nucleotides.

14. The method of claim 1, wherein each of the instances of optical activity comprises fluorescence generated from the respective label.

15. The method of claim 1, wherein the dye is a fluorescent dye, the respective label is a fluorescent nanoparticle or a FRET partner or the fluorescent dye and a fluorescence generated from the fluorescent nanoparticle or the FRET partner or the fluorescent dye is measured using light sheet microscopy, spinning disk confocal microscopy, three-dimensional super resolution microscopy, three-dimensional single molecule localization microscopy, laser scanning disk confocal microscopy, stimulated emission depletion microscopy, stochastic optical reconstruction microscopy, super-resolution optical fluctuation imaging microscopy, single molecule localization microscopy or total internal reflection fluorescence microscopy.

16. A method of determining a sequence of a least a portion of a nucleic acid molecule, comprising:
- fixing the nucleic acid molecule in a single stranded linearized stretched form on a test substrate, thereby forming a fixed stretched nucleic acid on the test substrate;
- exposing the fixed stretched nucleic acid to a respective oligonucleotide probe species in a set of oligonucleotide probe species, wherein each respective oligonucleotide probe species of the set of oligonucleotide probe species is capable of hybridizing to its complementary portion located at a plurality of locations on the fixed stretched nucleic acid and comprises (i) a unique respective predetermined sequence, (ii) a predetermined length, and (iii) a respective label selected from the group consisting of a dye, a fluorescent nanoparticle, a plasmon resonant particle, a light-scattering particle, and a FRET partner, wherein the exposing step occurs under conditions such that oligonucleotide probes of the respective oligonucleotide probe species of the set of oligonucleotide probe species repetitively transiently and reversibly bind to a plurality of locations on the fixed stretched nucleic acid, thereby forming a respective transient heteroduplex on each of the plurality of locations on the fixed stretched nucleic acid, and respective instances of optical activity from the respective label are generated by repetitively transiently and reversibly binding the oligonucleotide probes of the respective oligonucleotide probe species of the set of oligonucleotide probe species to the plurality of locations on the fixed stretched nucleic acid on the test substrate and are detected on each of the plurality of locations on the fixed stretched nucleic acid on the test substrate;
- determining which portions of the fixed stretched nucleic acid are complementary to the respective oligonucleotide probe species of the set of oligonucleotide probe species by measuring the respective instances of optical activity on each of the plurality of locations on the fixed stretched nucleic acid on the test substrate occurring during the exposing step using a two-dimensional imager capable of detecting the respective instances of optical activity generated from the respective label, thereby obtaining a first set of positions on the fixed stretched nucleic acid which are complementary to the respective oligonucleotide probe species of the set of oligonucleotide probe species;
- washing the test substrate to remove the respective oligonucleotide probe species of the set of oligonucleotide probe species from the test substrate;
- repeating the exposing step, the measuring step, and the washing step by exposing the fixed stretched nucleic acid to another respective oligonucleotide probe species in the set of oligonucleotide probe species, thereby obtaining a second set of positions on the fixed stretched nucleic acid which are complementary to the another respective oligonucleotide probe species of the set of oligonucleotide probe species; and
- determining the sequence of at least the portion of the nucleic acid molecule based on the first set of positions on the fixed stretched nucleic acid which are complementary to the respective oligonucleotide probe species of the set of oligonucleotide probe species and the second set of positions on the fixed stretched nucleic acid which are complementary to the another respective oligonucleotide probe species of the set of oligonucleotide probe species.

* * * * *

SEQUENCE LISTING

```
<160> NUMBER OF SEQ ID NOS: 9

<210> SEQ ID NO 1
<211> LENGTH: 16
<212> TYPE: DNA
<213> ORGANISM: Artificial Sequence
<220> FEATURE:
<223> OTHER INFORMATION: Synthetic

<400> SEQUENCE: 1 aaaacccccgg ggttttt                                                  16
```

<210> SEQ ID NO 2
<211> LENGTH: 3000
<212> TYPE: DNA
<213> ORGANISM: Artificial Sequence
<220> FEATURE:
<223> OTHER INFORMATION: synthetic

<400> SEQUENCE: 2

| | |
|---|---|
| aaaaaaaaac cggcccagct ttcttcatta ggttatacat ctaccgctcg ccagggcggc | 60 |
| gacctcgcgg gttttcgcta tttatgaaaa ttttccggtt taaggcgttt ccgttcttct | 120 |
| tcgtcataac ttaatgtttt tatttaaaat accctctgaa aagataggat agcacacgtg | 180 |
| ctgaaagcga ggcttttggg cctctgtcgt ttcctttctc tgttttttgtc cgtggaatga | 240 |
| acaatggaag tcaacaaaaa gcagctggct gacattttcg gtgcgagtat ccgtaccatt | 300 |
| cagaactggc aggaacaggg aatgcccgtt ctgcgaggcg gtggcaaggg taatgaggtg | 360 |
| ctttatgact ctgccgccgt cataaaatgg tatgccgaaa gggatgctga aattgagaac | 420 |
| gaaaagctgc gccgggaggt tgaagaactg cggttcttat acatctaata gtgattatct | 480 |
| acatacatta tgaatctaca ttttaggtaa agattaattg agtaccaggt ttcagatttg | 540 |
| cttcaataaa ttctgactgt agctgctgaa acgttgcggt tgaactatat ttccttataa | 600 |
| cttttacgaa agagtttctt tgagtaatca cttcactcaa gtgcttccct gcctccaaac | 660 |
| gatacctgtt agcaatattt aatagcttga atgatgaag agctctgtgt ttgtcttcct | 720 |
| gcctccagtt cgccgggcat tcaacataaa aactgatagc accggagtt ccggaaacga | 780 |
| aatttgcata tacccattgc tcacgaaaaa aaatgtcctt gtcgatatag ggatgaatcg | 840 |
| cttggtgtac ctcatctact gcgaaaactt gacctttctc tcccatattg cagtcgcggc | 900 |
| acgatggaac taaattaata ggcatcaccg aaaattcagg ataatgtgca ataggaagaa | 960 |
| aatgatctat atttttttgtc tgtcctatat caccacaaaa cctgaaactg gcgcgtgaga | 1020 |
| tggggcgacc gtcatcgtaa tatgttctag cgggtttgtt tttatctcgg agattatttt | 1080 |
| cataaagctt ttctaattta accttttgtca ggttaccaac tactaaggtt gtaggctcaa | 1140 |
| gagggtgtgt cctgtcgtag gtaaataact gacctgtcga gcttaatatt ctatattgtt | 1200 |
| gttctttctg caaaaaagtg gggaagtgag taatgaaatt atttctaaca tttatctgca | 1260 |
| tcataccttc cgagcattta ttaagcattt cgctataagt tctcgctgga agaggtagtt | 1320 |
| ttttcattgt actttacctt catctctgtt cattatcatc gcttttaaaa cggttcgacc | 1380 |
| ttctaatcct atctgaccat tataatttt tagaatgcgg cgttttccgg aactggaaaa | 1440 |
| ccgacatgtt gatttcctga acgggatat catcaaagcc atgaacaaag cagccgcgct | 1500 |
| ggatgaactg ataccggggt tgctgagtga atatatcgaa cagtcaggtt aacaggctgc | 1560 |
| ggcattttgt ccgcgccggg cttcgctcac tgttcaggcc ggagccacag accgccgttg | 1620 |
| aatgggcgga tgctaattac tatctcccga agaatccgc ataccaggaa gggcgctggg | 1680 |
| aaacactgcc ctttcagcgg gccatcatga atgcgatggg cagcgactac atccgtgagg | 1740 |
| tgaatgtggt gaagtctgcc cgtgtcggtt attccaaaat gctgctgggt gtttatgcct | 1800 |
| acttatagaa gcataagcag cgcaacaccc ttatctggtt gccgacggat ggtgatgccg | 1860 |
| agaactttat gaaacccac gttgagccga ctattcgtga tattccgtcg ctgctgttaa | 1920 |
| ttgagtttat agtgatttta tgaatctatt ttgatgatat tatctacata cgactggcgt | 1980 |
| gccatgcttg ccgggatgtc aaatttaata aggtgatagt aaataaaaca attgcatgtc | 2040 |

```
cagagctcat tcgaagcaga tatttctgga tattgtcata aaacaattta gtgaatttat    2100
catcgtccac ttgaatctgt ggttcattac gtcttaactc ttcatattta gaaatgaggc    2160
tgatgagttc catatttgaa aagttttcat cactacttag ttttttgata gcttcaagcc    2220
agagttgtct ttttctatct actctcatac aaccaataaa tgctgaaatg aattctaagc    2280
ggagatcgcc tagtgatttt aaactattgc tggcagcatt cttgagtcca atataaaagt    2340
attgtgtacc ttttgctggg tcaggttgtt ctttaggagg agtaaaagga tcaaatgcac    2400
taaacgaaac tgaaacaagc gatcgaaaat atccctttgg gattcttgac tcgataagtc    2460
tattattttc agagaaaaaa tattcattgt tttctgggtt ggtgattgca ccaatcattc    2520
cattcaaaat tgttgtttta ccacacccat tccgcccgat aaaagcatga atgttcgtgc    2580
tgggcataga attaaccgtc acctcaaaag gtatagttaa atcactgaat ccggagcac    2640 ttttctatt aaatgaaaag tggaaatctg acaattctgg caaaccatt aacacacgtg      2700 cgaactgtcc atgaatttct gaaagagtta cccctctaag taatgaggtg ttaaggacgc    2760
tttcattttc aatgtcggct aatcgatttg gccatactac taaatcctga atagctttaa    2820
gaaggttatg tttaaaacca tcgcttaatt tgctgagatt aacatagtag tcaatgcttt    2880
cacctaagga aaaaaacatt tcagggagtt gactgaattt tttatctatt aatgaataag    2940
tgcttgacct atttcttcat tacgccatta tacatctagc ccaccgctgc caaaaaaaa     3000
```

<210> SEQ ID NO 3
<211> LENGTH: 68
<212> TYPE: DNA
<213> ORGANISM: Artificial Sequence
<220> FEATURE:
<223> OTHER INFORMATION: synthetic

<400> SEQUENCE: 3

```
accggttgta ctagaggatt cggatagcta aaatcgtaaa aatgcggatt ataatgtccc    60
cccctcag                                                            68
```

<210> SEQ ID NO 4
<211> LENGTH: 68
<212> TYPE: DNA
<213> ORGANISM: Artificial Sequence
<220> FEATURE:
<223> OTHER INFORMATION: synthetic

<400> SEQUENCE: 4

```
accggttgta ctagaggacc ccaatagctg gatgcgtaaa aatgcggatt ataatgtccc    60
cccctcag                                                            68
```

<210> SEQ ID NO 5
<211> LENGTH: 68
<212> TYPE: DNA
<213> ORGANISM: Artificial Sequence
<220> FEATURE:
<223> OTHER INFORMATION: synthetic

<400> SEQUENCE: 5

```
acaaattgta ctagaggatt cggatagcta aaatcgtaaa aatgcggatt ataatgtccc    60
cccctcag                                                            68
```

<210> SEQ ID NO 6
<211> LENGTH: 17
<212> TYPE: DNA
<213> ORGANISM: Artificial Sequence

```
<220> FEATURE:
<223> OTHER INFORMATION: synthetic

<400> SEQUENCE: 6
acggtgttgc cacagtt                                                        17

<210> SEQ ID NO 7
<211> LENGTH: 11
<212> TYPE: DNA
<213> ORGANISM: Artificial Sequence
<220> FEATURE:
<223> OTHER INFORMATION: synthetic

<400> SEQUENCE: 7
aacggtgtca t                                                              11

<210> SEQ ID NO 8
<211> LENGTH: 11
<212> TYPE: DNA
<213> ORGANISM: Artificial Sequence
<220> FEATURE:
<223> OTHER INFORMATION: synthetic

<400> SEQUENCE: 8
ttgccacagt a                                                              11

<210> SEQ ID NO 9
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (17)..(22)
<223> OTHER INFORMATION: n is a, c, g, or t

<400> SEQUENCE: 9
nnnnnttgcc acagtannnn nn                                                  22
```